(12) United States Patent
Chen et al.

(10) Patent No.: US 7,132,258 B1
(45) Date of Patent: Nov. 7, 2006

(54) NUCLEIC ACID ENCODING VITAMIN D RECEPTOR RELATED POLYPEPTIDE

(75) Inventors: J. Don Chen, Westborough, MA (US); Hui Li, Westborough, MA (US)

(73) Assignee: University of Massachusetts, Worcester, MA (US)

( * ) Notice: Subject to any disclaimer, the term of this patent is extended or adjusted under 35 U.S.C. 154(b) by 0 days.

(21) Appl. No.: 09/041,994

(22) Filed: Mar. 13, 1998

Related U.S. Application Data

(60) Provisional application No. 60/073,674, filed on Feb. 4, 1998.

(51) Int. Cl.
  *C12N 15/11* (2006.01)
  *C12N 5/10* (2006.01)
  *C12N 15/63* (2006.01)

(52) U.S. Cl. .................. 435/69.1; 435/320.1; 435/325; 536/23.5

(58) Field of Classification Search ............... 435/69.1, 435/320.1, 325; 536/23.4
See application file for complete search history.

(56) References Cited

FOREIGN PATENT DOCUMENTS

WO  WO 98/56806   12/1998
WO  WO 98/57982   12/1998

OTHER PUBLICATIONS

George et al. (1988) Macro Molecular Sequences and Synthesis (Ed. by D. H. Schlesinger) Alan R. Uss, Inc., New York, pp. 127-149.*
Hardy et al. (1996) J. Clinical Endocrinology and Metabolism 81:4400-4405.*
Anzick, Sarah L. et al. "AIB1, A Steroid Receptor Coactivator Amplified in Breast and Ovarian Cancer" *Science,* 277:965-968 (Aug. 15, 1997).
Chen, Hongwu et al. "Nuclear Receptor Coactivator ACTR Is A Novel Histone Acetyltransferase And Forms A Multimeric Activation Complex With P/CAF and CBP/p300" *Cell,* 90:569-580 (Aug. 8, 1997).
Li, Hui et al. "RAC3, A Steroid/Nuclear Receptor-Associated Coactivator That Is Related To SRC-1 and TIF2" *Proc. Natl. Acad. Sci. USA* 94:8479-8484 (Aug. 5, 1997).
Torchia, Joseph et al. "The Transcriptional Co-Activator p/CIP Binds CBP And Mediates Nuclear-Receptor Function" *Nature* 387:677-684 (Jun. 12, 1997).
Genbank™ Accession No. AF010227 for *Homo sapiens* receptor-associated coactivator 3 (RAC3) mRNA, complete cds (Aug. 13, 1997).
Genbank™ Accession No. AF012108 for *Homo sapiens* Amplified in Breast Cancer (AIB1) mRNA, complete cds (Aug. 21, 1997).
Genbank™ Accession No. AF016031 for *Homo sapiens* Thyroid Hormone Receptor Activator Molecule (TRAM-1) mRNA, complete cds. (Nov. 5, 1997).
Genbank™ Accession No. AF036892 for *Homo sapiens* Nuclear Receptor Coactivator (ACTR) mRNA, complete cds. (Dec. 22, 1997).
Genbank™ Accession No. AF044080 for Xenopus Laevis Retinoid X Receptor-Interacting Coactivator XICO mRNA, complete cds. (Feb. 8, 1998).
Genbank™ Accession No. AF000581 for Mus Musculus p300/CBP/Co-Integrator Protein mRNA, complete cods. (Jun. 25, 1997).
Genbank™ Accession No. HSU80737 for *Homo sapiens* CAGH16 mRNA, complete cds. Dec. 18, 1997).
Genbank™ Accession No. W84822 for Soares fetal liver spleen 1NFLS S1 *Homo sapiens* cDNA clone 415808 5' (Jun. 27, 1996).
Genbank™ Accession No. AA114092 for Stratagene HeLa Cell s3 937216 *Homo sapiens* cDNA clone 563178 5' similar to TR:G726034 G726034 (Nov, 13, 1996).
Genbank™ Accession No. AA065268 for Testis 5 *Homo sapiens* cDNA clone f05502 3' (Dec. 31, 1996).
Genbank™ Accession No. AA150333 for Soares pregnant uterus NbHPU *Homo sapiens* cDNA clone 491268 5' (May 14, 1997).
Genbank™ Accession No. AA488485 for Stratagene HeLa cell s3 937216 *Homo sapiens* cDNA clone 843158 5' (Aug. 11, 1997).
Genbank™ Accession No. AA764263 for Soares 2NbMT Mus musculus cDNA clone 1225771 5' (Jan. 27, 1998).
Genbank™ Accession No. AA530243 for Stratagene mouse diaphragm (#937303) Mus musculus cDNA clone 931306 5' (Jul. 22, 1997).
Genbank™ Accession No. AA065271 for f08502r Testis 5 *Homo sapiens* cDNA clone f08502 3' (Dec. 31, 1996).
Genbank™ Accession No. R28559 for *Homo sapiens* cDNA clone 1336295' (Apr. 25, 1995).
Genbank™ Accession No. T77368 for *Homo sapiens* cDNA clone 113822 5' (Mar. 15, 1995).
Genbank™ Accession No. AA045419 for Soares pregnant uterus NbHPU *Homo sapiens* cDNA clone 487104 5' May 10, 1997).
Genbank™ Accession No. W84775 for Soares fetal liver spleen 1NFLS S1 *Homo sapiens* cDNA clone 415808 3' (Jun. 27, 1996).
Genbank™ Accession No. AA065269 for Testis 5 *Homo sapiens* cDNA clone d07502 3' (Dec. 31, 1996).
Genbank™ Accession No. AA065270 for Testis 5 *Homo sapiens* cDNA clone e08502 3' (Dec. 31, 1996).
Genbank™ Accession No. R21765 for *Homo sapiens* cDNA clone 130344 5' (Apr. 18, 1995).

(Continued)

*Primary Examiner*—Michael Pak
(74) *Attorney, Agent, or Firm*—Lahive & Cockfield LLP; Debra J. Milasincic, Esq.

(57) ABSTRACT

A new transcriptional co-activator that interacts with steroid/nuclear receptors has been identified. The peptide and its nucleic acid sequences are useful for modulating the activity of steroid/nuclear receptors and biochemical processes in which steroid/nuclear receptors play a role.

12 Claims, 16 Drawing Sheets

OTHER PUBLICATIONS

Genbank™ Accession No. AA065272 for Testis 5 *Homo sapiens* cDNA clone c08500 3' (Dec. 31, 1996).
Genbank™ Accession No. R66357 for *Homo sapiens* cDNA clone 141188 5' (May 30, 1995).
Genbank™ Accession No. AA823647 for Knowles Solter mouse 2 cell *Mus musculus* cDNA clone 1125873 5' (Feb. 17, 1998).
Genbank™ Accession No. H04364 for *Homo sapiens* cDNA clone 149324 5' (Jun. 20, 1995).
Genbank™ Accession No. AA300819 for Testis tumor *Homo sapiens* cDNA 5' (Apr. 18, 1997).
Genbank™ Accession No. T77062 for *Homo sapiens* cDNA clone 113822 3' (Mar. 15, 1995).
Genbank™ Accession No. AA360136 for Fetal lung II *Homo sapiens* cDNA 5' (Apr. 21, 1997).
Genbank™ Accession No. R28355 for *Homo sapiens* cDNA clone 133629 3' (Apr. 25, 1995).
Genbank™ Accession No. R67499 for *Homo sapiens* cDNA clone 141092 3' (May 30, 1995).
Genbank™ Accession No. R21718 for *Homo sapiens* cDNA clone 130344 3' (Apr. 18, 1995).
Genbank™ Accession No. AA163058 for Stratagene mouse skin (#937313) *Mus musculus* cDNA clone 607891 5' (Feb. 12, 1997).
Genbank™ Accession No. R66358 for *Homo sapiens* cDNA clone 141188 3' May 30, 1995).
Genbank™ Accession No. AA422600 for Knowles Solter mouse 2 cell *Mus musculus* cDNA clone 793854 5' (Oct. 16, 1997).
Genbank™ Accession No. AA089946 for chn1953.seq.F Fetal heart, Lambda ZAP Express *Homo sapiens* cDNA 5' (Oct. 24, 1996).
Genbank™ Accession No. AA445710 for Knowles Solter mouse 2 cell *Mus musculus* cDNA clone 779126 5' (Aug. 15, 1997).
Genbank™ Accession No. AA178622 for Soares mouse 3NbMS *Mus musculus* cDNA clone 621369 5' (Feb. 17, 1997).
Takeshita, Akira et al. "TRAM-1, A Novel 160-kDa Thyroid Hormone Receptor Activator Molecule, Exhibits Distinct Properties from Steroid Receptor Coactivator-1" *J. Biol. Chem.* 272:27629-27634.

* cited by examiner

```
     GCTGGATGGTGGACTCAGAGACCAATAAAAATAAACTGCTTGAACATCCTTTGACTGGTT
  1  ---------+---------+---------+---------+---------+---------+  60
     CGACCTACCACCTGAGTCTCTGGTTATTTTTATTTGACGAACTTGTAGGAAACTGACCAA

AGCCAGTTGCTGATGTATATTCAAGATGAGTGGATTAGGAGAAAACTTGGATCCACTGGC
 61  ---------+---------+---------+---------+---------+---------+ 120
     TCGGTCAACGACTACATATAAGTTCTACTCACCTAATCCTCTTTTGAACCTAGGTGACCG

M  S  G  L  G  E  N  L  D  P  L  A  -

CAGTGATTCACGAAAACGCAAATTGCCATGTGATACTCCAGGACAAGGTCTTACCTGCAG
121  ---------+---------+---------+---------+---------+---------+ 180
     GTCACTAAGTGCTTTTGCGTTTAACGGTACACTATGAGGTCCTGTTCCAGAATGGACGTC

S  D  S  R  K  R  K  L  P  C  D  T  P  G  Q  G  L  T  C  S -

TGGTGAAAAACGGAGACGGGAGCAGGAAAGTAAATATATTGAAGAATTGGCTGAGCTGAT
181  ---------+---------+---------+---------+---------+---------+ 240
     ACCACTTTTTGCCTCTGCCCTCGTCCTTTCATTTATATAACTTCTTAACCGACTCGACTA

G  E  K  R  R  R  E  Q  E  S  K  Y  I  E  E  L  A  E  L  I -

ATCTGCCAATCTTAGTGATATTGACAATTTCAATGTCAAACCAGATAAATGTGCGATTTT
241  ---------+---------+---------+---------+---------+---------+ 300
     TAGACGGTTAGAATCACTATAACTGTTAAAGTTACAGTTTGGTCTATTTACACGCTAAAA

S  A  N  L  S  D  I  D  N  F  N  V  K  P  D  K  C  A  I  L -

AAAGGAAACAGTAAGACAGATACGTCAAATAAAAGAGCAAGGAAAAACTATTTCCAATGA
301  ---------+---------+---------+---------+---------+---------+ 360
     TTTCCTTTGTCATTCTGTCTATGCAGTTTATTTTCTCGTTCCTTTTGATAAAGGTTACT

K  E  T  V  R  Q  I  R  Q  I  K  E  Q  G  K  T  I  S  N  D -

TGATGATGTTCAAAAAGCCGATGTATCTTCTACAGGGCAGGGAGTTATTGATAAAGACTC
361  ---------+---------+---------+---------+---------+---------+ 420
     ACTACTACAAGTTTTTCGGCTACATAGAAGATGTCCCGTCCCTCAATAACTATTTCTGAG

D  D  V  Q  K  A  D  V  S  S  T  G  Q  G  V  I  D  K  D  S -

CTTAGGACCGCTTTTACTTCAGGCATTGGATGGTTTCCTATTTGTGGTGAATCGAGAGGC
421  ---------+---------+---------+---------+---------+---------+ 480
     GAATCCTGGCGAAAATGAAGTCCGTAACCTACCAAAGGATAAACACCACTTAGCTCTCCG

L  G  P  L  L  L  Q  A  L  D  G  F  L  F  V  V  N  R  E  A -

AAACATTGTATTTGTATCAGAAAATGTCACACAATACCTGCAATATAAGCAAGAGGACCT
481  ---------+---------+---------+---------+---------+---------+ 540
     TTTGTAACATAAACATAGTCTTTTACAGTGTGTTATGGACGTTATATTCGTTCTCCTGGA

N  I  V  F  V  S  E  N  V  T  Q  Y  L  Q  Y  K  Q  E  D  L -

GGTTAACACAAGTGTTTACAATATCTTACATGAAGAAGACAGAAAGGATTTTCTTAAGAA
541  ---------+---------+---------+---------+---------+---------+ 600
     CCAATTGTGTTCACAAATGTTATAGAATGTACTTCTTCTGTCTTTCCTAAAAGAATTCTT
```

TTTACCAAAATCTACAGTTAATGGAGTTTCCTGGACAAATGAGACCCAAAGACAAAAAAG
601   ---------+---------+---------+---------+---------+---------+  660
      AAATGGTTTTAGATGTCAATTACCTCAAAGGACCTGTTTACTCTGGGTTTCTGTTTTTTC

L  P  K  S  T  V  N  G  V  S  W  T  N  E  T  Q  R  Q  K  S  -

CCATACATTTAATTGCCGTATGTTGATGAAAACACCACATGATATTCTGGAAGACATAAA
661   ---------+---------+---------+---------+---------+---------+  720
      GGTATGTAAATTAACGGCATACAACTACTTTTGTGGTGTACTATAAGACCTTCTGTATTT

H  T  F  N  C  R  M  L  M  K  T  P  H  D  I  L  E  D  I  N  -

CGCCAGTCCTGAAATGCGCCAGAGATATGAAACAATGCAGTGCTTTGCCCTGTCTCAGCC
721   ---------+---------+---------+---------+---------+---------+  780
      GCGGTCAGGACTTTACGCGGTCTCTATACTTTGTTACGTCACGAAACGGGACAGAGTCGG

A  S  P  E  M  R  Q  R  Y  E  T  M  Q  C  F  A  L  S  Q  P  -

ACGAGCTATGATGGAGGAAGGGGAAGATTTGCAATCTTGTATGATCTGTGTGGCACGCCG
781   ---------+---------+---------+---------+---------+---------+  840
      TGCTCGATACTACCTCCTTCCCCTTCTAAACGTTAGAACATACTAGACACACCGTGCGGC

R  A  M  M  E  E  G  E  D  L  Q  S  C  M  I  C  V  A  R  R  -

CATTACTACAGGAGAAAGAACATTTCCATCAAACCCTGAGAGCTTTATTACCAGACATGA
841   ---------+---------+---------+---------+---------+---------+  900
      GTAATGATGTCCTCTTTCTTGTAAAGGTAGTTTGGGACTCTCGAAATAATGGTCTGTACT

I  T  T  G  E  R  T  F  P  S  N  P  E  S  F  I  T  R  H  D  -

TCTTTCAGGAAAGGTTGTCAATATAGATACAAATTCACTGAGATCCTCCATGAGGCCTGG
901   ---------+---------+---------+---------+---------+---------+  960
      AGAAAGTCCTTTCCAACAGTTATATCTATGTTTAAGTGACTCTAGGAGGTACTCCGGACC

L  S  G  K  V  V  N  I  D  T  N  S  L  R  S  S  M  R  P  G  -

CTTTGAAGATATAATCCGAAGGTGTATTCAGAGATTTTTTAGTCTAAATGATGGGCAGTC
961   ---------+---------+---------+---------+---------+---------+  1020
      GAAACTTCTATATTAGGCTTCCACATAAGTCTCTAAAAAATCAGATTTACTACCCGTCAG

F  E  D  I  I  R  R  C  I  Q  R  F  F  S  L  N  D  G  Q  S  -

ATGGTCCCAGAAACGTCACTATCAAGAAGCTTATCTTAATGGCCATGCAGAAACCCCAGT
1021  ---------+---------+---------+---------+---------+---------+  1080
      TACCAGGGTCTTTGCAGTGATAGTTCTTCGAATAGAATTACCGGTACGTCTTTGGGGTCA

W  S  Q  K  R  H  Y  Q  E  A  Y  L  N  G  H  A  E  T  P  V  -

ATATCGATTCTCGTTGGCTGATGGAACTATAGTGACTGCACAGACAAAAAGCAAACTCTT
1081  ---------+---------+---------+---------+---------+---------+  1140
      TATAGCTAAGAGCAACCGACTACCTTGATATCACTGACGTGTCTGTTTTTCGTTTGAGAA

Y  R  F  S  L  D  G  T  I  V  T  A  Q  T  K  S  K  L  F  -

CCGAAATCCTGTAACAAATGATCGACATGGCTTTGTCTCAACCCACTTCCTTCAGAGAGA
1141  ---------+---------+---------+---------+---------+---------+  1200
      GGCTTTAGGACATTGTTTACTAGCTGTACCGAAACAGAGTTGGGTGAAGGAAGTCTCTCT

```
         ACAGAATGGATATAGACCAAACCCAAATCCTGTTGGACAAGGGATTAGACCACCTATGGC
1201     ---------+---------+---------+---------+---------+---------+ 1260
         TGTCTTACCTATATCTGGTTTGGGTTTAGGACAACCTGTTCCCTAATCTGGTGGATACCG

Q  N  G  Y  R  P  N  P  N  P  V  G  Q  G  I  R  P  P  M  A  -

TGGATGCAACAGTTCGGTAGGCGGCATGAGTATGTCGCCAAACCAAGGCTTACAGATGCC
1261     ---------+---------+---------+---------+---------+---------+ 1320
         ACCTACGTTGTCAAGCCATCCGCCGTACTCATACAGCGGTTTGGTTCCGAATGTCTACGG

G  C  N  S  S  V  G  G  M  S  M  S  P  N  Q  G  L  Q  M  P  -

GAGCAGCAGGGCCTATGGCTTGGCAGACCCTAGCACCACAGGGCAGATGAGTGGAGCTAG
1321     ---------+---------+---------+---------+---------+---------+ 1380
         CTCGTCGTCCCGGATACCGAACCGTCTGGGATCGTGGTGTCCCGTCTACTCACCTCGATC

S  S  R  A  Y  G  L  A  D  P  S  T  T  G  Q  M  S  G  A  R  -

GTATGGGGGTTCCAGTAACATAGCTTCATTGACCCCTGGGCCAGGCATGCAATCACCATC
1381     ---------+---------+---------+---------+---------+---------+ 1440
         CATACCCCCAAGGTCATTGTATCGAAGTAACTGGGGACCCGGTCCGTACGTTAGTGGTAG

Y  G  G  S  S  N  I  A  S  L  T  P  G  P  G  M  Q  S  P  S  -

TTCCTACCAGAACAACAACTATGGGCTCAACATGAGTAGCCCCCCACATGGGAGTCCTGG
1441     ---------+---------+---------+---------+---------+---------+ 1500
         AAGGATGGTCTTGTTGTTGATACCCGAGTTGTACTCATCGGGGGGTGTACCCTCAGGACC

S  Y  Q  N  N  N  Y  G  L  N  M  S  S  P  P  H  G  S  P  G  -

TCTTGCCCCAAACCAGCAGAATATCATGATTTCTCCTCGTAATCGTGGGAGTCCAAAGAT
1501     ---------+---------+---------+---------+---------+---------+ 1560
         AGAACGGGGTTTGGTCGTCTTATAGTACTAAAGAGGAGCATTAGCACCCTCAGGTTTCTA

L  A  P  N  Q  Q  N  I  M  I  S  P  R  N  R  G  S  P  K  I  -

AGCCTCACATCAGTTTTCTCCTGTTGCAGGTGTGCACTCTCCCATGGCATCTTCTGGCAA
1561     ---------+---------+---------+---------+---------+---------+ 1620
         TCGGAGTGTAGTCAAAAGAGGACAACGTCCACACGTGAGAGGGTACCGTAGAAGACCGTT

A  S  H  Q  F  S  P  V  A  G  V  H  S  P  M  A  S  S  G  N  -

TACTGGGAACCACAGCTTTTCCAGCAGCTCTCTCAGTGCCCTGCAAGCCATCAGTGAAGG
1621     ---------+---------+---------+---------+---------+---------+ 1680
         ATGACCCTTGGTGTCGAAAAGGTCGTCGAGAGAGTCACGGGACGTTCGGTAGTCACTTCC

T  G  N  H  S  F  S  S  S  S  L  S  A  L  Q  A  I  S  E  G  -

TGTGGGGACTTCCCTTTTATCTACTCTGTCATCACCAGGCCCAAATTGGATAACTCTCC
1681     ---------+---------+---------+---------+---------+---------+ 1740
         ACACCCCTGAAGGGAAAATAGATGAGACAGTAGTGGTCCGGGGTTTAACCTATTGAGAGG

V  G  T  S  L  L  S  T  L  S  S  P  G  P  K  L  D  N  S  P  -

CAATATGAATATTACCCAACCAAGTAAAGTAAGCAATCAGGATTCCAAGAGTCCTCTGGG
1741     ---------+---------+---------+---------+---------+---------+ 1800
         GTTATACTTATAATGGGTTGGTTCATTTCATTCGTTAGTCCTAAGGTTCTCAGGAGACCC

N  M  N  I  T  Q  P  S  K  V  S  N  Q  D  S  K  S  P  L  G  -

CTTTTATTGCGACCAAAATCCAGTGGAGAGTTCAATGTGTCAGTCAAATAGCAGAGATCA
```

FIGURE 1B

```
1801 ---------+---------+---------+---------+---------+---------+ 1860
     GAAAATAACGCTGGTTTTAGGTCACCTCTCAAGTTACACAGTCAGTTTATCGTCTCTAGT

F   Y   C   D   Q   N   P   V   E   S   S   M   C   Q   S   N   S   R   D   H   -

CTCAGTGACAAAGAAAGTAAGGAGAGCAGTGTTGAGGGGGCAGAGAATCAAAGGGGTCC
1861 ---------+---------+---------+---------+---------+---------+ 1920
     GGAGTCACTGTTTCTTTCATTCCTCTCGTCACAACTCCCCCGTCTCTTAGTTTCCCCAGG

L   S   D   K   E   S   K   E   S   S   V   E   G   A   E   N   Q   R   G   P   -

TTTGGAAAGCAAAGGTCATAAAAAATTACTGCAGTTACTTACCTGTTCTTCTGATGACCG
1921 ---------+---------+---------+---------+---------+---------+ 1980
     AAACCTTTCGTTTCCAGTATTTTTTAATGACGTCAATGAATGGACAAGAAGACTACTGGC

L   E   S   K   G   H   K   K   L   L   Q   L   L   T   C   S   S   D   D   R   -

GGGTCATTCCTCCTTGACCAACTCCCCCCTAGATTCAAGTTGTAAAGAATCTTCTGTTAG
1981 ---------+---------+---------+---------+---------+---------+ 2040
     CCCAGTAAGGAGGAACTGGTTGAGGGGGGATCTAAGTTCAACATTTCTTAGAAGACAATC

G   H   S   S   L   T   N   S   P   L   D   S   S   C   K   E   S   S   V   S   -

TGTCACCAGCCCCTCTGGAGTCTCCTCCTCTACATCTGGAGGAGTATCCTCTACATCCAA
2041 ---------+---------+---------+---------+---------+---------+ 2100
     ACAGTGGTCGGGGAGACCTCAGAGGAGGAGATGTAGACCTCCTCATAGGAGATGTAGGTT

V   T   S   P   S   G   V   S   S   S   T   S   G   G   V   S   S   T   S   N   -

TATGCATGGGTCACTGTTACAAGAGAAGCACCGGATTTTGCACAAGTTGCTGCAGAATGG
2101 ---------+---------+---------+---------+---------+---------+ 2160
     ATACGTACCCAGTGACAATGTTCTCTTCGTGGCCTAAAACGTGTTCAACGACGTCTTACC

M   H   G   S   L   L   Q   E   K   H   R   I   L   H   K   L   L   Q   N   G   -

GAATTCACCAGCTGAGGTAGCCAAGATTACTGCAGAAGCCACTGGGAAAGACACCAGCAG
2161 ---------+---------+---------+---------+---------+---------+ 2220
     CTTAAGTGGTCGACTCCATCGGTTCTAATGACGTCTTCGGTGACCCTTTCTGTGGTCGTC

N   S   P   A   E   V   A   K   I   T   A   E   A   T   G   K   D   T   S   S   -

TATAACTTCTTGTGGGGACGGAAATGTTGTCAAGCAGGAGCAGCTAAGTCCTAAGAAGAA
2221 ---------+---------+---------+---------+---------+---------+ 2280
     ATATTGAAGAACACCCCTGCCTTTACAACAGTTCGTCCTCGTCGATTCAGGATTCTTCTT

I   T   S   C   G   D   G   N   V   V   K   Q   E   Q   L   S   P   K   K   K   -

GGAGAATAATGCACTTCTTACATACCTGCTGGACAGGGATGATCCTAGTGATGCACTCTC
2281 ---------+---------+---------+---------+---------+---------+ 2340
     CCTCTTATTACGTGAAGAATCTATGGACGACCTGTCCCTACTAGGATCACTACGTGAGAG

E   N   N   A   L   L   R   Y   L   L   D   R   D   D   P   S   D   A   L   S   -

TAAAGAACTACAGCCCCAAGTGGAAGGAGTGGACAATAAAATGAGTCAGTGCACCAGCTC
2341 ---------+---------+---------+---------+---------+---------- 2400
     ATTTCTTGATGTCGGGGTTCACCTTCCTCACCTGTTATTTTACTCAGTCACGTGGTC 3/ 3

K   E   L   Q   P   Q   V   E   G   V   D   N   K   M   S   Q   C   T   S   S   -

CACCATTCCTAGCTCAAGTCAAGAGAAAGACCCTAAAATTAAGACAGAGACAAGTGAAGA
2401 ---------+---------+---------+---------+---------+---------+ 2460
     GTGGTAAGGATCGAGTTCAGTTCTCTTTCTGGGATTTTAATTCTGTCTCTGTTCACTTCT
```

GGGATCTGGAGACTTGGATAATCTAGATGCTATTCTTGGTGATCTGACTAGTTCTGACTT
2461   ----------+---------+---------+---------+---------+---------+  2520
       CCCTAGACCTCTGAACCTATTAGATCTACGATAAGAACCACTAGACTGATCAAGACTGAA

G  S  G  D  L  D  N  L  D  A  I  L  G  D  L  T  S  S  D  F   -

TTACAATAATTCCATATCCTCAAATGGTAGTCATCTGGGGACTAAGCAACACGTGTTTCA
2521   ----------+---------+---------+---------+---------+---------+  2580
       AATGTTATTAAGGTATAGGAGTTTACCATCAGTAGACCCCTGATTCGTTGTCCACAAAGT

Y  N  N  S  I  S  S  N  G  S  H  L  G  T  K  Q  Q  V  F  Q   -

AGGAACTAATTCTCTGGGTTTGAAAAGTTCACAGTCTGTGCAGTCTATTCGTCCTCCATA
2581   ----------+---------+---------+---------+---------+---------+  2640
       TCCTTGATTAAGAGACCCAAACTTTTCAAGTGTCAGACACGTCAGATAAGCAGGAGGTAT

G  T  N  S  L  G  L  K  S  S  Q  S  V  Q  S  I  R  P  P  Y   -

TAACCGAGCAGTGTCTCTGGATAGCCCTGTTTCTGTTGGCTCAAGTCCTCCAGTAAAAAA
2641   ----------+---------+---------+---------+---------+---------+  2700
       ATTGGCTCGTCACAGAGACCTATCGGGACAAAGACAACCGAGTTCAGGAGGTCATTTTTT

N  R  A  V  S  L  D  S  P  V  S  V  G  S  S  P  P  V  K  N   -

TATCAGTGCTTTCCCCATGTTACCAAAGCAACCCATGTTGGGTGGGAATCCAAGAATGAT
2701   ----------+---------+---------+---------+---------+---------+  2760
       ATAGTCACGAAAGGGGTACAATGGTTTCGTTGGGTACAACCCACCCTTAGGTTCTTACTA

I  S  A  F  P  M  L  P  K  Q  P  M  L  G  G  N  P  R  M  M   -

GGATAGTCAGGAAAATTATGGCTCAAGTATGGGTGGGCCAAACCGAAATGTGACTGTGAC
2761   ----------+---------+---------+---------+---------+---------+  2820
       CCTATCAGTCCTTTTAATACCGAGTTCATACCCACCCGGTTTGGCTTTACACTGACACTG

D  S  Q  E  N  Y  G  S  S  M  G  G  P  N  R  N  V  T  V  T   -

TCAGACTCCTTCCTCAGGAGACTGGGGCTTACCAAACTCAAAGGCCGGCAGAATGGAACC
2821   ----------+---------+---------+---------+---------+---------+  2880
       AGTCTGAGGAAGGAGTCCTCTGACCCCGAATGGTTTGAGTTTCCGGCCGTCTTACCTTGG

Q  T  P  S  S  G  D  W  G  L  P  N  S  K  A  G  R  M  E  P   -

TATGAATTCAAACTCCATGGCAAGACCAGGAGGAGATTATAATACTTCTTTACCCAGACC
2881   ----------+---------+---------+---------+---------+---------+  2940
       ATACTTAAGTTTGAGGTACCGTTCTGGTCCTCCTCTAATATTATGAAGAAATGGGTCTGG

M  N  S  N  S  M  G  R  P  G  G  D  Y  N  T  S  L  P  R  P   -

TGCACTGGGTGGCTCTATTCCCACATTGCCTCTTCGGTCTAATAGCATACCAGGTGCGAG
2941   ----------+---------+---------+---------+---------+---------+  3000
       ACGTGACCCACCGAGATAAGGGTGTAACGGAGAAGCCAGATTATCGTATGGTCCACGCTC

A  L  G  G  S  I  P  T  L  P  L  R  S  N  S  I  P  G  A  R   -

ACCAGTATTGCAACAGCAGCAGCAGATGCTTCAAATGAGGCCTGGTGAAATCCCCATGGG
3001   ----------+---------+---------+---------+---------+---------+  3060
       TGGTCATAACGTTGTCGTCGTCGTCTACGAAGTTTACTCCGGACCACTTTAGGGGTACCC

```
          AATGGGGGCTAATCCCTATGCCCAAGCAGCAGCATCTAACCAACTGGGTTCCTGGCCCGA
3061    ---------+---------+---------+---------+---------+---------+  3120
          TTACCCCCGATTAGGGATACCGGTTCGTCGTCGTAGATTGGTTGACCCAAGGACCGGGCT

M  G  A  N  P  Y  G  Q  A  A  A  S  N  Q  L  G  S  W  P  D  -

TGGCATGTTGTCCATGGAACAAGTTTCTCATGGCACTCAAAATAGGCCTCTTCTTAGGAA
3121    ---------+---------+---------+---------+---------+---------+  3180
          ACCGTACAACAGGTACCTTGTCAAAGAGTACCGTGAGTTTTATCCGGAGAAGAATCCTT

G  M  L  S  M  E  Q  V  S  H  G  T  Q  N  R  P  L  L  R  N  -

TTCCCTGGATGATCTTGTTGGCCCACCTTCCAACCTGGAAGGCCAGAGTGACGAAAGAGC
3181    ---------+---------+---------+---------+---------+---------+  3240
          AAGGGACCTACTAGAACAACCCGGTGGAAGGTTGGACCTTCCGGTCTCACTGCTTTCTCG

S  L  D  D  L  V  G  P  P  S  N  L  E  G  Q  S  D  E  R  A  -

ATTATTGGACCAGCTGCACACTCTTCTCAGCAACACAGATGCGACAGGCCTGGAAGAAAT
3241    ---------+---------+---------+---------+---------+---------+  3300
          TAATAACCTGGTCGACGTGTCAGAAGAGTCGTTGTGTCTACGCTGTCCGGACCTTCTTTA

L  L  D  Q  L  H  T  L  L  S  N  T  D  A  T  G  L  E  E  I  -

TGACAGAGCTTTGGGCATTCCTGAACTTGTCAATCAGGGACAGGCATTAGAGCCCAAACA
3301    ---------+---------+---------+---------+---------+---------+  3360
          ACTGTCTCGAAACCCGTAAGGACTTGAACAGTTAGTCCCTGTCCGTAATCTCGGGTTTGT

D  R  A  L  G  I  P  E  L  V  N  Q  G  Q  A  L  E  P  K  Q  -

GGATGCTTTCCAAGGCCAAGAAGCAGCAGTAATGATGGATCAGAAGGCAGGATTATATGG
3361    ---------+---------+---------+---------+---------+---------+  3420
          CCTACGAAAGGTTCCGGTTCTTCGTCGTCATTACTACCTAGTCTTCCGTCCTAATATACC

D  A  F  Q  G  Q  E  A  A  V  M  M  D  Q  K  A  G  L  Y  G  -

ACAGACATACCCAGCACAGGGCCTCCAATGCAAGGAGGCTTTCATCTTCAGGGACAATC
3421    ---------+---------+---------+---------+---------+---------+  3480
          TGTCTGTATGGGTCGTGTCCCCGGAGGTTACGTTCCTCCGAAAGTAGAAGTCCCTGTTAG

Q  T  Y  P  A  Q  G  P  P  M  Q  G  G  F  H  L  Q  G  Q  S  -

ACCATCTTTTAACTCTATGATGAATCAGATGAACCAGCAAGGCAATTTTCCTCTCCAAGG
3481    ---------+---------+---------+---------+---------+---------+  3540
          TGGTAGAAAATTGAGATACTACTTAGTCTACTTGGTCGTTCCGTTAAAAGGAGAGGTTCC

P  S  F  N  S  M  M  N  Q  M  N  Q  Q  G  N  F  P  L  Q  G  -

AATGCACCCACGAGCCAACATCATGAGACCCCGGACAAACACCCCCAAGCAACTTAGAAT
3541    ---------+---------+---------+---------+---------+---------+  3600
          TTACGTGGGTGCTCGGTTGTAGTACTCTGGGGCCTGTTTGTGGGGGTTCGTTGAATCTTA

M  H  P  R  A  N  I  M  R  P  R  T  N  T  P  K  Q  L  R  M  -

GCAGCTTCAGCAGAGGCTGCAGGGCCAGCAGTTTTTGAATCAGAGCCGACAGGCACTTGA
3601    ---------+---------+---------+---------+---------+---------+  3660
          CGTCGAAGTCGTCTCCGACGTCCCGGTCGTCAAAAACTTAGTCTCGGCTGTCCGTGAACT

Q  L  Q  Q  R  L  Q  G  Q  Q  F  L  N  Q  S  R  Q  A  L  E  -

ATTGAAAATGGAAAACCCTACTGCTGGTGGTGCTGCGGTGATGAGGCCTATGATGCAGCC
```

FIGURE 1E

```
3661 ----------+----------+---------+----------+---------+---------+ 3720
     TAACTTTTACCTTTTGGGATCACGACCACCACGACGCCACTACTCCGGATACTACGTCGG

L  K  M  E  N  P  T  A  G  G  A  A  V  M  R  P  M  M  Q  P  -

CCAGCAGGGTTTTCTTAATGCTCAAATGGTCGCCCAACGCAGCAGAGAGCTGCTAAGTCA
3721 ----------+----------+---------+----------+---------+---------+ 3780
     GGTCGTCCCAAAAGAATTACGAGTTTACCAGCGGGTTGCGTCGTCTCTCGACGATTCAGT

Q  Q  G  F  L  N  A  Q  M  V  A  Q  R  S  R  E  L  L  S  H  -

TCACTTCCGACAACAGAGGGTGGCTATGATGATGCAGCAGCAGCAACAGCAGCAGCAGCA
3781 ----------+----------+---------+----------+---------+---------+ 3840
     AGTGAAGGCTGTTGTCTCCCACCGATACTACTACGTCGTCGTCGTTGTCGTCGTCGTCGT

H  F  R  Q  Q  R  V  A  M  M  M  Q  Q  Q  Q  Q  Q  Q  Q  Q  -

GCAGCAGCAGCAGCAACAGCAACAGCAACAGCAACAGCAGCAACAGCAGCAAACCCAGGC
3841 ----------+----------+---------+----------+---------+---------+ 3900
     CGTCGTCGTCGTCGTTGTCGTTGTCGTTGTCGTTGTCGTCGTTGTCGTCGTTTGGGTCCG

Q  Q  Q  Q  Q  Q  Q  Q  Q  Q  Q  Q  Q  Q  Q  Q  Q  T  Q  A  -

CTTCAGCCCACCTCCTAATGTGACTGCTTCCCCCAGCATGGATGGGCTTTTGGCAGGACC
3901 ----------+----------+---------+----------+---------+---------+ 3960
     GAAGTCGGGTGGAGGATTACACTGACGAAGGGGGTCGTACCTACCCGAAAACCGTCCTGG

F  S  P  P  P  N  V  T  A  S  P  S  M  D  G  L  L  A  G  P  -

CACAATGCCACAAGCTCCTCCGCAACAGTTTCCATATCAACCAAATTATGGAATGGGACA
3961 ----------+----------+---------+----------+---------+---------+ 4020
     GTGTTACGGTGTTCGAGGAGGCGTTGTCAAAGGTATAGTTGGTTTAATACCTTACCCTGT

T  M  P  Q  A  P  P  Q  Q  F  P  Y  Q  P  N  Y  G  M  G  Q  -

ACAACCAGATCCAGCCTTTGGTCGAGTGTCTAGTCCTCCCAATGCAATGATGTCGTCAAG
4021 ----------+----------+---------+----------+---------+---------+ 4080
     TGTTGGTCTAGGTCGGAAACCAGCTCACAGATCAGGAGGGTTACGTTACTACAGCAGTTC

Q  P  D  P  A  F  G  R  V  S  S  P  P  N  A  M  M  S  S  R  -

AATGGGTCCCTCCCAGAATCCCATGATGCAACACCCGCAGGCTGCATCCATCTATCAGTC
4081 ----------+----------+---------+----------+---------+---------+ 4140
     TTACCCAGGGAGGGTCTTAGGGTACTACGTTGTGGGCGTCCGACGTAGGTAGATAGTCAG

M  G  P  S  Q  N  P  M  M  Q  H  P  Q  A  A  S  I  Y  Q  S  -

CTCAGAAATGAAGGGCTGGCCATCAGGAAATTTGGCCAGGAACAGCTCCTTTTCCCAGCA
4141 ----------+----------+---------+----------+---------+---------+ 4200
     GAGTCTTTACTTCCCGACCGGTAGTCCTTTAAACCGGTCCTTGTCGAGGAAAAGGGTCGT

S  E  M  K  G  W  P  S  G  N  L  A  R  N  S  S  F  S  Q  Q  -

GCAGTTTGCCCACCAGGGGAATCCTGCAGTGTATAGTATGGTGCACATGAATGGCAGCAG
4201 ----------+----------+---------+----------+---------+---------+ 4260
     CGTCAAACGGGTGGTCCCCTTAGGACGTCACATATCATACCACGTGTACTTACCGTCGTC

Q  F  A  H  Q  G  N  P  A  V  Y  S  M  V  H  M  N  G  S  S  -

TGGTCACATGGGACAGATGAACATGAACCCCATGCCCATGTCTGGCATGCCTATGGGTCC
4261 ----------+----------+---------+----------+---------+---------+ 4320
     ACCAGTGTACCCTGTCTACTTGTACTTGGGGTACGGGTACAGACCGTACGGATACCCAGG
```

TGATCAGAAATACTGCTGACATCTCTGCACCAGGACCTCTTAAGGAAACCACTGTACAAA
4321   ---------+---------+---------+---------+---------+---------+  4380
       ACTAGTCTTTATGACGACTGTAGAGACGTGGTCCTGGAGAATTCCTTTGGTGACATGTTT

D  Q  K  Y  C  *

TGACACTGCACTAGGATTATTGGGAAGGAATCATTGTTCCAGGCATCCATCTTGGAAGAA
4381   ---------+---------+---------+---------+---------+---------+  4440
       ACTGTGACGTGATCCTAATAACCCTTCCTTAGTAACAAGGTCCGTAGGTAGAACCTTCTT

AGGACCAGCTTTGAGCTCCATCAAGGGTATTTTAAGTGATGTCATTTGAGCAGGA
4441   ---------+---------+---------+---------+---------+-----  4495
       TCCTGGTCGAAACTCGAGGTAGTTCCCATAAAATTCACTACAGTAAACTCGTCCT
```

FIGURE 1G

```
                            bHLH domain
   1  MSGLGENLDP  LASDSRKRKL  PCDTPGQGLT  CSGEKRRREQ  ESKYIEELAE
  51  LISANLSDID  NFNVKPDKCA  ILKETVRQIR  QIKEQGKTIS  NDDDVQKADV
                                PAS "A" domain
 101  SSTGQGVIDK  DSLGPLLLQA  LDGFLFVVNR  EANIVFVSEN  VTQYLQYKQE
 151  DLVNTSVYNI  LHEEDRKDFL  KNLPKSTVNG  VSWTNEPQRQ  KSHTFNCRML
 201  MKTPHDILED  INASPEMRQR  YETMQCFALS  QPRAMMEEGE  DLQSCMICVA
                    PAS "B" domain
 251  RRITTGERTF  PSNPESFITR  HDLSGKVVNI  DTNSLRSSMR  PGFEDIIRRC
 301  IQRFFSLNDG  QSWSQKRHYQ  EAYLNGHAET  PVYRFSLADG  TIVTAQTKSK
 351  LFRNPVTNDR  HGFVSTHFLQ  REQNGYRPNP  NPVGQGIRPP  MAGCNSSVGG
      ┌→RAC3.1
 401  MSMSPNQGLQ  MPSSRAYGLA  DPSTTGQMSG  ARYGGSSNIA  SLTPGPGMQS
 451  PSSYQNNNYG  LNMSSPPHGS  PGLAPNQQNI  MISPRNRGSP  KIASHQFSPV
 501  AGVHSPMASS  GNTGNHSFSS  SSLSALQAIS  EGVGTSLLST  LSSPGPKLDN
 551  SPNMNITQPS  KVSNQDSKSP  LGFYCDQNPV  ESSMCQSNSR  DHLSDKESKE
 601  SSVEGAENQR  GPLESKGHKK  LLQLITCSSD  DRGHSSLTNS  PLDSSCKESS
                                      ii
 651  VSVTSPSGVS  SSTSGGVSST  SNMHGSLLQE  KHRILHKLLQ  NGNSPAEVAK
                                                iii
 701  ITAEATGKDT  SSITSCGDGN  VVKQEQLSPK  KKENNALLRY  LLDRDDPSDA
 751  LSKELQPQVE  GVDNKMSQCT  SSTIPSSSQE  KDPKIKTETS  EEGSGDLDNL
             iv
 801  DAILGDITSS  DFYNNSISSN  GSHLGTKQQV  FQGTNSLGLK  SSQSVQSIRP
 851  PYNRAVSLDS  PVSVGSSPPV  KNISAFPMLP  KQPMLGGNPR  MMDSQENYGS
 901  SMGGPNRNVT  VTQTPSSGDW  GLPNSKAGRM  EPMNSNSMGR  PGGDYNTSLP
 951  RPALGGSIPT  LPLRSNSIPG  ARPVLQQQQQ  MLQMRPGEIP  MGMGANPYGQ
1001  AAASNQLGSW  PDGMLSMEQV  SHGTQNRPLL  RNSLDDLVGP  PSNLEGQSDE
           v                           vi
1051  RALLDQLHTL  LSNTDATGLE  EIDRALGIPE  LVNQGQALEP  KQDAFQGQEA
1101  AVMMDQKAGL  YGQTYPAQGP  PMQGGFHLQG  QSPSFNSMMN  QMNQQGNFPL
                                Q-rich domain
1151  QGMHPRANIM  RPRTNTPKQL  RMQLQQRLQG  QQFLNQSRQA  LELKMENPTA
      ←┐RAC3.1
1201  GGAAVMRPMM  QPQQGFLNAQ  MVAQRSRELL  SHHFRQQRVA  MMMQQQQQQQ
1251  QQQQQQQQQ  QQQQQQQQT  QAFSPPPNVT  ASPSMDGLLA  GPTMPQAPPQ
1301  QFPYQPNYGM  GQQPDPAFGR  VSSPPNAMMS  SRMGPSQNPM  MQHPQAASIY
1351  QSSEMKGWPS  GNLARNSSFS  QQQFAHQGNP  AVYSMVHMNG  SSGHMGQMNM
1401  NPMPMSGMPM  GPDQKYC*
```

FIGURE 2

I.
```
     SKGHKK LLQLL TCSSDD      RAC3   (615-631)
     SKGQTK LLQLL TTKSDD      TIF2   (640-651)
     SQTSHK LVQLL TTTAEE      SRC1   (632-643)
```
II.
```
     LQEKHR ILHKLL QNGNSP     RAC3   (678-695)
     LKEKHK ILHRLL QDSSSP     TIF2   (683-699)
     LTERHK ILHRLL QEG.SP     SRC1   (683-699)
```
III.
```
     KKKE..NNA LLRYLL DRDDPSD   RAC3   (730-749)
     KKKE...NA LLRYLL DKDDTKD   TIF2   (738-753)
     KKKESKDHQ LLRYLL DKDE.KD   SRC1   (739-757)
```
iv.
```
     DLDNLDA ILGDL            RAC3   (796-807)
     ELDNLEE ILDDL            TIF2   (803-814)
     DLDQFDQ LLPTL            SRC1   (810-821)
```
v.
```
     EGQSDERA LLDQL HTLL      RAC3   (1045-1061)
     ESPSDEGA LLDQL YLAL      TIF2   (1071-1087)
     EGRNDEKA LLEQL VSFL      SRC1   (924-940)
```
vi.
```
     LEEIDRALG IPELV NQ       RAC3   (1069-1084)
     LEEIDRALG IPELV SQ       TIF2   (1093-1108)
     LAELDRALG IDKLV .Q       SRC1   (948-962)
```
vii.
```
     QTPQAQQKS LLQQLI TE*     SRC1   (1424-1440)
```

FIGURE 4

NUCLEIC ACID ENCODING VITAMIN D RECEPTOR RELATED POLYPEPTIDE

RELATED APPLICATIONS

This application claims priority to a provisional application, U.S. Ser. No. 60/073,674, entitled A Transcriptional Coactivator of Steroid/Nuclear Receptors and Uses Therefore filed on Feb. 4, 1998. The content of that application is expressly incorporated by reference.

BACKGROUND OF THE INVENTION

The invention relates to a new transcriptional coactivator of steroid/nuclear receptors.

Steroids, thyroid hormones, vitamin D3, and retinoids are lipid-soluble small molecules which play a role in the control of cell differentiation, embryonic development, and homeostasis, as well as adult physiology. These molecules exert the majority of their effects on cells by interacting with specific receptors which, when bound by a specific ligand, affect transcription by interacting directly with chromatin. In addition, in their unliganded state, these receptors inhibit transcription of certain genes. The diverse biological effects of these molecules suggest that hormone actions are mediated by complex signaling. The hormone receptors comprise a large superfamily which displays substantial specificity in regulating gene expression (Beato et al. 1995. *Cell* 83: 851–857; Evans. 1988. *Science* 240: 889–895). These receptors share a common domain structure, including a N-terminal DNA-binding domain (DBD or C domain), which binds to specific DNA sequences, and a C-terminal ligand-binding domain (LBD or E domain), which binds to the cognate hormone. Retinoic acid receptors (RARs), thyroid hormone receptors (TRs), vitamin D3 receptor (VDR), peroxisomal proliferator activated receptors (PPARs), and several other orphan receptors form heterodimeric complexes with retinoid-X receptors (RXRs) (Yu et al., *Cell* 67: 1251–66, 1991; Kliewer et al., *Nature* 355:446–9, 1992; Willy et al., *Genes & Development* 2:1033–45, 1995). Such receptor heterodimers can bind to a broad range of response elements composed of two related half sites and activate target gene expression (Yu et al., *Cell* 67:1251–66, 1991; Kliewer et al., Nature 355:446–9, 1992; Umesono et al., Cell 65:1255–1266, 1991; Forman et al., Cell 81:541–550, 1996 Heyman et al., *Cell* 68:397–406, 1992).

Transcriptional activation by steroid/nuclear receptors is thought to involve at least two separate processes: derepression and activation (Mangelsdorf and Evans, *Cell* 83:841–850, 1995; Wong and Wolffe, *Genes Dev.*9: 2696–711, 1995). Repression is effected in part by association of unliganded receptors with the nuclear receptor corepressors SMRT and N-CoR (Horlein et al., Nature 377: 397–404, 1995; Chen and Evans, Nature 377:454–7, 1995). Ligand-binding triggers dissociation of these corepressors and recruitment of coactivators. Putative steroid/nuclear receptor coactivators have been identified, including: RIP-140 and RIP-160 (Cavailles et al., EMBO J. 14:3741–3751; Cavailles et al., *Proc. Natl. Acad. Sci. USA* 91:10009–13, 1994), ERAP-140 and ERAP-160 (Halachmi et al., *Science* 264:1455–8, 1994), TIF1 (Le Douarin et al., EMBO J. 14:2020–2033, 1995), steroid receptor coactivator-1 (SRC-1) (Kamei et al., *Cell* 85:403–14, 1996; Onate et al., *Science* 270:1354–1357, 1995), TRIP1/SUG1 (Lee et al., *Nature* 374:91–4, 1995), ARA70 (Yeh and Chang, *Proc. Natl. Acad. Sci. USA* 93:5517–21, 1996), transcriptional intermediate factor-2 (TIF2) (Voegel et al., EMBO J. 15:3667–3675, 1996), and CBP/p300 (Kamei et al., *Cell* 85:403–14, 1996; Chakravarti et al., *Nature* 383:99–103, 1996; Smith et al., *Proc. Natl. Acad. Sci. USA* 93:8884–8, 1996). Two of these potential coactivators, SRC-1 and TIF2, are related proteins and enhance transcriptional activation by several hormone receptors (Onate et al., *Science* 270:1354–1357, 1995; Voegel et al., *EMBO J.* 15:3667–3675, 1996; Smith et al., *Proc. Natl. Acad. Sci. USA* 93:8884–8, 1996; McInerney et al., *Proc. Natl. Acad. Sci. USA* 93:10069–73).

Hormone binding is thought to induce a conformational change in the receptor and, in turn, activate the C-terminal ligand-dependent activation function (AF-2) of the receptor (Mangeledorf et al., *Cell* 83:835–839, 1995). At the extreme C-terminus of the AF-2 domain, there are about 20 amino acids that form an amphipathic helix (Bourguet et al., *Nature* 375:377–82, 1995). This helix is referred to as the AF-2 activation domain (AF2-AD) (Renaud et al., *Nature* 378: 681–9, 1995), TC, or T4 domain (Baniahmad et al., *Mol. Cell. Bio.* 15:76–86, 1995; Hollenberg and Evans, *Cell* 55:899–906, 1988). Deletion and several point mutations in this domain abolish the AF-2 function completely (Damm et al., *Proc. Natl. Acad. Sci. USA* 90:2989–2993, 1993; Schulman et al., *Mol. Cell. Biol.* 16:3807–13, 1995; Barettino et al., EMBO J. 13:3039–3049, 1994; Durand et al., EWBO J. 13:5370–5382,1994). The AF-2 domain can act alone as an activation domain (AD) when fused to a heterologous DNA binding domain (DBD) (Barettino et al., EMBO J. 13:3039–3049, 1994; Schulman et al., *Proc. Natl. Acad. Sci. USA* 92:8288–92, 1995). Comparison of the recent ligand binding domain (LBD) crystal structures of unliganded retinoid-X receptor $\alpha$ (RXR$\alpha$; Bourguet et al., *Nature* 375: 377–82, 1995) with liganded retinoic acid receptor $\gamma$ (RAR$\gamma$; Renaud et al., *Nature* 378:681–9, 1995) and liganded thyroid hormone receptor $\alpha$ (TRa; Wagner et al., *Nature* 378: 690–697, 1995) reveals a striking difference in the relative position of the AF2-AD. It is proposed that, upon hormone binding, the AF2-AD rotates 180 degrees and forms part of the hormone binding surface, covering the ligand-binding cavity. The hydrophobic residues of the helix face the cavity, contacting the hydrophobic ligand, while the charged residues extend into the solvent, possibly mediating protein—protein interactions with coactivators (Bourguet et al., *Nature* 375:377–82, 1995; Renaud et al., *Nature* 378:681–9, 1995; Wagner et al., *Nature* 378:690–697, 1995). The AF2-AD domain has also been shown to be required for derepression by inducing dissociation of the corepressors (Chen and Evans, *Nature* 377:454–7, 1995; Baniahmad et al., *Mol. Cell. Bio.* 15:76–86, 1995). The discovery of novel molecules which are involved in hormone binding, transcriptional repression will allow for the modulation of responses to steroid hormones and, ultimately, will facilitate the modulation of cell differentiation, embryonic development, and homeostasis, as well as adult physiology.

SUMMARY OF THE INVENTION

The invention is based, at least in part, on the discovery of a new transcriptional activator of steroid/nuclear receptors which is referred to herein as RAC3. RAC3 encodes a protein of about 1417 amino acids and is capable of interaction (enhanced by the presence of ligand) with hormone receptors that requires the presence of receptor AF-2 domains. RAC3 can also directly activate transcription. In addition, expression of RAC3 is increased in the presence of receptor-ligand complexes.

The RAC3 molecules of the present invention are useful as modulating agents in regulating a variety of cellular processes. Accordingly, in one aspect, this invention provides isolated nucleic acid molecules encoding RAC3 proteins or biologically active portions thereof, as well as nucleic acid fragments suitable as primers or hybridization probes for the detection of RAC3-encoding nucleic acids.

In one embodiment, a RAC3 nucleic acid molecule is 60% homologous to the nucleotide sequence shown in SEQ ID NO:1 or complement thereof. In a preferred embodiment, an isolated RAC3 nucleic acid molecule has the nucleotide sequence at least 70% homologous to the nucleotide sequence shown in SEQ ID NO:1 or the complement thereof. In a more preferred embodiment, an isolated RAC3 nucleic acid molecule has the nucleotide sequence at least 80% or more preferably 85% homologous to the nucleotide sequence shown in SEQ ID NO:1 or the complement thereof. In a further preferred embodiment, an isolated RAC3 nucleic acid molecule has the nucleotide sequence at least 90% or more preferably 95% homologous to the nucleotide sequence shown in SEQ ID NO:1 or the complement thereof. In another preferred embodiment, an isolated RAC3 nucleic acid molecule has the nucleotide sequence shown in SEQ ID NO:1.

Preferred RAC3 nucleic acid molecules encode RAC3 domains. For example, preferred RAC3 nucleic acid molecules inculde a nucleotide sequence encoding an N-terminal region of about 350 amino acids comprising a basic-helix-loop helix (bHLH) domain and two Per-AhR-Sim (PAS) domains (Swanson and Bradfield. 1993., Pharmacogenetics 3:213) as shown in FIGS. 2–4. Other RAC 3 domains include the repeated leucine motifs sharing a consensus sequence of LXLL or LLXXL, where L is leucine and X is any amino acid (e.g. shown in amino acids 621–625, 684–689, 737–742, 803–807, 1053–1057, and 1178–1182 of SEQ ID NO:2). The C-terminal domain of RAC3 also comprises a glutamine-rich (Q-rich) domain. More preferred RAC3 nucleic acid molecules encode N terminal domains that interact with steroid receptors, particularly class II receptors, e.g., about about nucleotides 1609–3136, or more preferably about nucleotides 1922–2341 of SEQ ID NO:1. Preferred RAC3 nucleic acid molecules encode proteins which comprise C terminal transactivating domains, e.g., nucleotides 3031–3767, 3031–3253, or 3136–3622. Other preferred RAC3 nucleic acids comprise all or a portion of the nucleotide sequence shown in about nucleotides 1–3311 of SEQ ID NO:1.

In another embodiment, a RAC3 nucleic acid molecule includes a nucleotide sequence encoding a protein having an amino acid sequence sufficiently homologous to the amino acid sequence of SEQ ID NO:2. In another preferred embodiment, a RAC3 nucleic acid molecule includes a nucleotide sequence encoding a protein having an amino acid sequence at least 60% homologous to the amino acid sequence of SEQ ID NO:2. In yet another preferred embodiment, a RAC3 nucleic acid molecule includes a nucleotide sequence encoding a protein having an amino acid sequence at least 70% homologous to the amino acid sequence of SEQ ID NO:2. In yet another preferred embodiment, a RAC3 nucleic acid molecule includes a nucleotide sequence encoding a protein having an amino acid sequence at least 80% homologous to the amino acid sequence of SEQ ID NO:2. In yet another preferred embodiment, a RAC3 nucleic acid molecule includes a nucleotide sequence encoding a protein having an amino acid sequence at least 90% homologous to the amino acid sequence of SEQ ID NO:2. In a more preferred embodiment, a RAC3 nucleic acid molecule includes a nucleotide sequence encoding a protein having an amino acid sequence shown in SEQ ID NO:2.

In yet another embodiment, a RAC3 nucleic acid molecule encodes a RAC3 protein and is a naturally occurring nucleotide sequence.

Another embodiment of the invention features RAC3 nucleic acid molecules which specifically detect RAC3 nucleic acid molecules relative to nucleic acid molecules encoding non-RAC3 proteins. For example, in one embodiment, a RAC3 nucleic acid molecule is at least about 200, 300, 400, 500, 600, 700, 900 or 1000 nucleotides in length and hybridizes under stringent conditions to a nucleic acid molecule comprising the nucleotide sequence shown in SEQ ID NO:1 or a complement thereof.

Another embodiment of the invention provides an isolated nucleic acid molecule which is antisense to the coding strand of a RAC3 nucleic acid.

Another aspect of the invention provides a vector comprising a RAC3 nucleic acid molecule. In certain embodiments, the vector is a recombinant expression vector. In another embodiment, the invention provides a host cell containing a vector of the invention. The invention also provides a method for producing a RAC3 protein by culturing in a suitable medium, a host cell of the invention containing a recombinant expression vector such that a RAC3 protein is produced.

Another aspect of this invention features isolated or recombinant RAC3 proteins and polypeptides. In one embodiment, an isolated RAC3 protein includes an N-terminal region of about 350 amino acids comprising a basic-helix-loop helix (bHLH) domain and two Per-AhR-Sim (PAS) domains (Swanson and Bradfield. 1993., Pharmacogenetics 3:213) as shown in FIGS. 2–4. Other RAC 3 protein domains include the repeated leucine motifs sharing a consensus sequence of LXLL or LLXXL, where L is leucine and X is any amino acid, e.g. shown in about amino acids 621–625, 684–689, 737–742, 803–807, 1055–1057, 1178–1182 of SEQ ID NO:2. The C-terminal domain of RAC3 also comprises a glutamine-rich (Q-rich) domain e.g. shown in about amino acids 1169–1313 of SEQ ID NO: 2. More preferred RAC3 proteins include N terminal domains which interact with steroid receptors, particularly class II receptors, e.g., shown in about amino acids 507–1017, or more preferably 613–752 of SEQ ID NO:2. Preferred RAC3 proteins also comprise C terminal transactivating domains, e.g., shown in about amino acids 982–1204, 982–1056, or 1017–1179.

In another embodiment, an isolated RAC3 protein has an amino acid sequence sufficiently homologous to the amino acid sequence of SEQ ID NO:2 such that it shares a biological activity with the RAC3 protein of SEQ ID NO:2. In a preferred embodiment, a RAC3 protein has an amino acid sequence at least about 60% homologous to the amino acid sequence of SEQ ID NO:2. In another preferred embodiment, a RAC3 protein has an amino acid sequence at least about 70% homologous to the amino acid sequence of SEQ ID NO:2. In another preferred embodiment, a RAC3 protein has an amino acid sequence at least about 80% homologous to the amino acid sequence of SEQ ID NO:2. In another preferred embodiment, a RAC3 protein has an amino acid sequence at least about 90% homologous to the amino acid sequence of SEQ ID NO:2. In another embodiment, a RAC3 protein has the amino acid sequence of SEQ ID NO:2.

Another embodiment of the invention features an isolated RAC3 protein which is encoded by a nucleic acid molecule having a nucleotide sequence at least about 60% homologous to a nucleotide sequence of SEQ ID NO:1, or a complement thereof. Another embodiment of the invention features an isolated RAC3 protein which is encoded by a nucleic acid molecule having a nucleotide sequence at least about 70% homologous to a nucleotide sequence of SEQ ID NO:1, or a complement thereof. Another embodiment of the invention features an isolated RAC3 protein which is encoded by a nucleic acid molecule having a nucleotide sequence at least about 80% homologous to a nucleotide sequence of SEQ ID NO:1, or a complement thereof. Another embodiment of the invention features an isolated RAC3 protein which is encoded by a nucleic acid molecule having a nucleotide sequence at least about 90% homologous to a nucleotide sequence of SEQ ID NO:1, or a complement thereof. This invention further features an isolated RAC3 protein which is encoded by a nucleic acid molecule having a nucleotide sequence which hybridizes under stringent hybridization conditions to a nucleic acid molecule comprising the nucleotide sequence of SEQ ID NO:1 or a complement thereof.

The RAC3 proteins of the present invention, or biologically active portions thereof, can be operatively linked to a non-RAC3 polypeptide to form RAC3 fusion proteins. The invention further features antibodies that specifically bind RAC3 proteins, such as monoclonal or polyclonal antibodies. In addition, the RAC3 proteins or biologically active portions thereof can be incorporated into pharmaceutical compositions, which optionally include pharmaceutically acceptable carriers.

In another aspect, the present invention provides a method for detecting RAC3 expression in a biological sample by contacting the biological sample with an agent capable of detecting a RAC3 nucleic acid molecule, protein or polypeptide such that the presence of a RAC3 nucleic acid molecule, protein or polypeptide is detected in the biological sample.

In another aspect, the present invention provides a method for detecting the presence of RAC3 activity in a biological sample by contacting the biological sample with an agent capable of detecting an indicator of RAC3 activity such that the presence of RAC3 activity is detected in the biological sample.

In another aspect, the invention provides a method for modulating RAC3 activity comprising contacting the cell with an agent that modulates RAC3 activity such that RAC3 activity in the cell is modulated. In one embodiment, the agent inhibits RAC3 activity. In another embodiment, the agent stimulates RAC3 activity. In one embodiment, the agent is an antibody that specifically binds to a RAC3 protein. In another embodiment, the agent modulates expression of RAC3 by modulating transcription of a RAC3 gene or translation of a RAC3 mRNA. In yet another embodiment, the agent is a nucleic acid molecule having a nucleotide sequence that is antisense to the coding strand of a RAC3 mRNA or a RAC3 gene.

In one embodiment, the methods of the present invention are used to treat a subject having a disorder characterized by aberrant RAC3 protein or nucleic acid expression or activity by administering an agent which is a RAC3 modulator to the subject. In one embodiment, the RAC3 modulator is a RAC3 protein. In another embodiment the RAC3 modulator is a RAC3 nucleic acid molecule. In yet another embodiment, the RAC3 modulator is a peptide, peptidomimetic, or other small molecule. In a preferred embodiment, the disorder characterized by aberrant RAC3 protein or nucleic acid expression is a developmental, differentiative, proliferative disordera.

The present invention also provides a diagnostic assay for identifying the presence or absence of a genetic alteration characterized by at least one of (i) aberrant modification or mutation of a gene encoding a RAC3 protein; (ii) misregulation of said gene; and (iii) aberrant post-translational modification of a RAC3 protein, wherein a wild-type form of said gene encodes an protein with a RAC3 activity.

In another aspect the invention provides a method for identifying a compound that binds to or modulates the activity of a RAC3 protein, by providing a indicator composition comprising a RAC3 protein having RAC3 activity, contacting the indicator composition with a test compound, and determining the effect of the test compound on RAC3 activity in the indicator composition to identify a compound that modulates the activity of a RAC3 protein.

Other features and advantages of the invention will be apparent from the following detailed description and claims.

BRIEF DESCRIPTION OF THE DRAWINGS

FIG. 1 is an illustration of the nucleotide sequence of RAC3 cDNA.

FIG. 2 is an illustration of the deduced amino acid sequence of RAC3

FIG. 4 is an illustration of the sequence alignment of LeuXXLeuLeu (LXXLL) motifs for RAC3, TIF2, and SRC-1

DETAILED DESCRIPTION OF THE INVENTION

The present invention is based on the discovery of novel molecules, referred to herein as RAC3 protein and nucleic acid molecules having certain conserved structural and functional features. RAC3 was identified as a nuclear receptor interacting-protein based on its ability to interact with RAR in the yeast two-hybrid system. Because of its properties, RAC3 is useful for modulating the effects of steroid/nuclear hormones and their receptors. It is also a useful tool for elucidating the mechanisms of steroid/nuclear hormone action. Several lines of evidence support the position that RAC3 is a general transcriptional coactivator for steroid/nuclear hormone receptors. First, RAC3 interacts with ligand activated receptors. Second, the ligand-dependent interaction with RAC3 requires an intact AF-2 activation domain on the receptor. Third, RAC3 itself contains a transcriptional activation domain. Finally, overexpression of RAC3 enhances ligand-stimulated transcriptional activation by steroid/nuclear receptors. In summary, all these biochemical properties of RAC3, and its sequence similarity with SRC-1 and TIF2, identify it as a distinct, third member of a novel receptor-associated coactivator gene family useful for elucidation of mechanisms of nuclear receptor function and for modification of hormone-related cellular functions, including therapeutic uses.

There are at least two distinct activation functional domains (i.e., AF-1 and AF-2) which have been identified in steroid/nuclear hormone receptors (Tasset et al., *Cell* 62:1177–87, 1990). The N-terminal AF-1 domain is active consitutively and its activity is not regulated by hormones. In contrast, the activity of the C-terminal AF2 depends completely on ligand binding. The exact role of the C-terminal AF2-AD helix in recruitment of coactivators is unclear. It is known that the AF2-AD alone is not sufficient for interaction with RAC3 or other coactivators, indicating that other regions of the LBD are required for recruitment of coactivators. Consistent with this hypothesis, several other activation motifs throughout the LBD of thyroid hormone receptor have been reported (Baniahmad et al., *Mol. Cell. Bio.* 15:76–86, 1995). Alternatively, the role of the AF2-AD may simply be to stabilize ligand-binding by forming part of the contacting surface for ligands (Renaud et al., *Nature* 378:681–9, 1995; Wagner et al., *Nature* 378:690–697, 1995), which in turn induces additional conformational change that allows association with coactivators.

Figure 3:
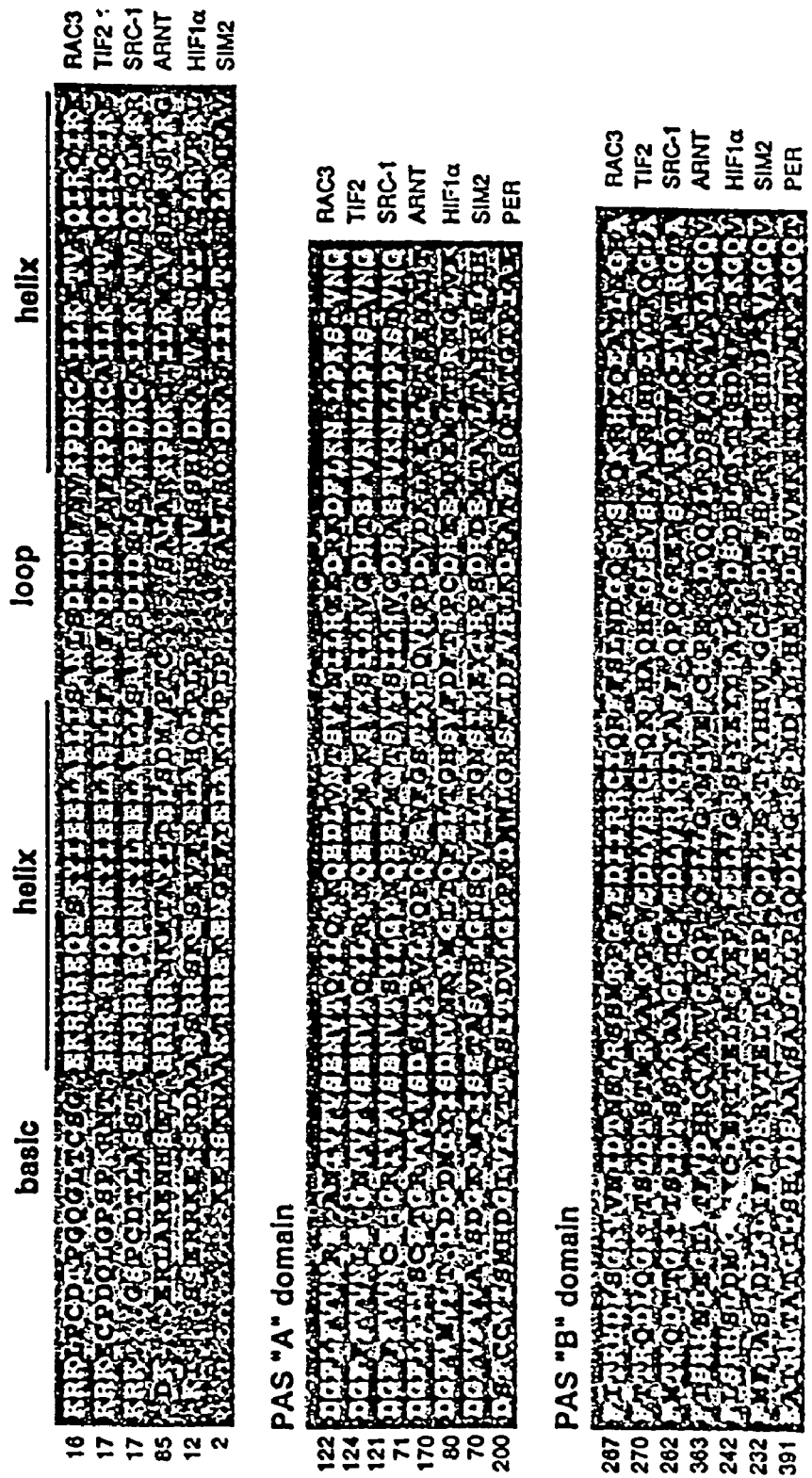
FIG. 3 is an illustration of the comparison of the nucleic acid sequences of basic-helix-loop helix (bHLH) and Per-AhR-Sim (PAS) domains of RAC3, TIF2, SRC-1, ARNT, HIF1α, SIM2, and period (PER)

In one embodiment, the RAC3 proteins of the present invention are proteins having an amino acid sequence of about 100, 250, 500, 750, or 1000 amino acids. Preferred portions of RAC3 comprise RAC3 domains. For example, in one embodiment RAC3 proteins comprise from about 140 or 162 amino acids, e.g., an N terminal nuclear receptor interacting domain shown in amino acids 613–752 of SEQ ID NO:2, or a C-terminal transactivator domain shown in amino acids 1017–1179 of SEQ ID NO:2. In other embodiments, for example, as illustrated in FIGS. 2, 3, and 4 preferred RAC3 proteins inculde an N-terminal region of about 350 amino acids comprising a basic-helix-loop helix (bHLH) domain and two Per-AhR-Sim (PAS) domains (Swanson and Bradfield. 1993., Pharmacogenetics 3:213). Other RAC 3 domains include the repeated leucine motifs sharing a consensus sequence of LXLL or LLXXL, where L is leucine and X is any amino acid for example as shown in amino acids 621–625, 684–689, 737–742, 803–807, 1053–1057, or 1178–1182. The C-terminal domain of RAC3 also comprises a glutamine-rich (Q-rich) domain e.g. from about amino acids 1169–1313. More preferred RAC3 proteins comprise domains that interact with steroid receptors, particularly class II receptors, e.g., amino acids 507–1017, or more preferably 613–752 of SEQ ID NO:2. Preferred RAC3 proteins also comprise transactivating domains, e.g., amino acids 982–1204, 982–1056, or 1017–1179 of SEQ ID NO:2.

Preferred RAC3 molecules of the present invention have an amino acid sequence sufficiently homologous to the amino acid sequence of SEQ ID NO:2. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains and/or a common functional activity. For example, amino acid or nucleotide sequences which share common structural domains have at least about 60% homology, preferably 70% homology, more preferably 80%–85%, and even more preferably 90–95% homology across the amino acid sequences of the domains and contain at least one and preferably two structural domains, are defined herein as sufficiently homologous. Furthermore, amino acid or nucleotide sequences which share at least 60%, preferably 70%, more preferably 80–85, or 90–95% homology and share a common functional activity are defined herein as sufficiently homologous.

Also preferred are "substantially identical" polypeptides. A "substantially identical" polypeptide sequence is an amino acid sequence that differs from a given sequence only by conservative amino acid substitutions, for example, substitution of one amino acid for another of the same class by one or more non-conservative substitutions, deletions, or insertions located at positions of the amino acid sequence which do not destroy the function of the polypeptide (assayed, e.g., as described herein).

As used interchangeably herein, an "RAC3 activity", "biological activity of RAC3" or "functional activity of RAC3", refers to an activity exerted by a RAC3 protein, polypeptide or nucleic acid molecule on a RAC3 responsive cell as determined in vivo, or in vitro, according to standard techniques. In one embodiment, a RAC3 activity is a direct activity, such as an association with a RAC3-target molecule. As used herein, a "target molecule" or "binding partner" is a molecule with which a RAC3 protein binds or interacts in nature, such that RAC3-mediated function is acheived. In an exemplary embodiment, a RAC3 target molecule is a class II steroid receptor e.g., RAR, RXR, VDR, PAR, TR, and PPAR-AD. In another exemplary embodiment, a RAC3 target molecule is an AF2-AD domain. RAC3 has also been shown to interact simultaneously with CβP and nuclear receptors in presence of ligand, or listone acetyltransferase activity. The presence of ligand can enhance the binding of RAC3 to steroid receptors. Exemplary RAC3 activities can be direct or indirect. An exemplary indirect activity includes, e.g., cellular signaling activity mediated by interaction of the RAC3 protein with a second protein (e.g., a steroid receptor).

In a preferred embodiment, a RAC3 activity includes one or more of: the activation of steroid hormone-mediated transcription, and binding to a RAC3 target molecule.

Accordingly, another embodiment of the invention features isolated RAC3 proteins and polypeptides having a RAC3 activity. Preferred RAC3 proteins have at least one RAC3 domain and a RAC3 activity. In still another preferred embodiment, a RAC3 protein has a RAC3 domain, a RAC3 activity, and an amino acid sequence sufficiently homologous to an amino acid sequence of SEQ ID NO:2.

Various aspects of the invention are described in further detail in the following subsections:

I. Isolated Nucleic Acid Molecules

One aspect of the invention pertains to isolated nucleic acid molecules that encode RAC3 proteins or biologically active portions thereof, as well as nucleic acid fragments sufficient for use as hybridization probes to identify RAC3-encoding nucleic acids (e.g., RAC3 mRNA) and fragments for use as PCR primers for the amplification or mutation of RAC3 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated RAC3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or a portion thereof, can be isolated using standard molecular biology techniques and the sequence information provided herein. Using all or portion of the nucleic acid sequence of SEQ ID NO:1 as a hybridization probe, RAC3 nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to RAC3 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human RAC3-1 cDNA. This cDNA comprises sequences encoding the human RAC3-1 protein (i.e., "the coding region", from about nucleotides 86–4330), as well as 5' untranslated sequences (about nucleotides 1–85) and 3' untranslated sequences (about nucleotides 4330–4496).

In certain embodiments the 5' regulatory region of the RAC3 gene, which is important in the tissue specific expression of RAC3, can be used to drive the expression of a heterologous (i.e., non-RAC3 gene) in a tissue-specific manner.

In another preferred embodiment, an isolated nucleic acid molecule of the invention comprises a nucleic acid molecule which is a complement of the nucleotide sequence shown in SEQ ID NO:1 or a portion thereof. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1 thereby forming a stable duplex.

In still another preferred embodiment, an isolated nucleic acid molecule of the present invention comprises a nucleotide sequence which is at least about 60–65%, preferably at least about 70–75%, more preferable at least about 80–85%, and even more preferably at least about 90–95% or more homologous to the nucleotide sequences shown in SEQ ID NO:1 or a portion thereof.

Moreover, the nucleic acid molecule of the invention can comprise only a portion of the nucleic acid sequence of SEQ ID NO:1, for example a fragment which can be used as a probe or primer or a fragment encoding a biologically active portion of a RAC3 protein. Exemplary RAC3 nucleic acids comprise all or a portion of the nucleotide sequence shown in about nucleotides 1–3311 of SEQ ID NO:1. The nucleotide sequence determined from the cloning of the RAC3 genes allows for the generation of probes and primers designed for use in identifying and/or cloning other RAC3 family members, as well as RAC3 homologues from other species. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense sequence of SEQ ID NO:1. In an exemplary embodiment, a nucleic acid molecule of the present invention comprises a nucleotide sequence which is greater than at least about 200, 300, 400, 500, 600, 700, 900, or 1000 nucleotides in length nucleotides in length and hybridizes under stringent hybridization conditions to a nucleic acid molecule of SEQ ID NO:1.

Probes based on the RAC3 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a RAC3 protein, such as by measuring a level of a RAC3-encoding nucleic acid in a sample of cells from a subject e.g., detecting RAC3 mRNA levels or determining whether a genomic RAC3 gene has been mutated or deleted.

A nucleic acid fragment encoding a "biologically active portion of a RAC3 protein" can be prepared by isolating a portion of SEQ ID NO:1 which encodes a polypeptide having a RAC3 biological activity (the biological activities of the RAC3 proteins have previously been described), expressing the encoded portion of the RAC3 protein (e.g., by recombinant expression in vitro) and assessing the activity of the encoded portion of the RAC3 protein.

The invention further encompasses nucleic acid molecules that differ from the nucleotide sequence shown in SEQ ID NO:1 due to degeneracy of the genetic code and thus encode the same RAC3 proteins as that encoded by the nucleotide sequence shown in SEQ ID NO:2. In another embodiment, an isolated nucleic acid molecule of the invention has a nucleotide sequence encoding a protein having an amino acid sequence shown in SEQ ID NO:2.

In addition to the RAC3 nucleotide sequences shown in SEQ ID NO:1, it will be appreciated by those skilled in the art that DNA sequence polymorphisms that lead to changes in the amino acid sequences of the RAC3 proteins may exist within a population (e.g., the human population). Such genetic polymorphism in the RAC3 genes may exist among individuals within a population due to natural allelic variation. As used herein, the terms "gene" and "recombinant gene" refer to nucleic acid molecules comprising an open reading frame encoding a RAC3 protein, preferably a mammalian RAC3 protein. Such natural allelic variations can typically result in 1–5% variance in the nucleotide sequence of a RAC3 gene. Any and all such nucleotide variations and resulting amino acid polymorphisms in RAC3 genes that are the result of natural allelic variation and that do not alter the functional activity of a RAC3 protein are intended to be within the scope of the invention.

Moreover, nucleic acid molecules encoding other RAC3 family members are intended to be within the scope of the invention. For example, cDNAs can be identified based on the nucleotide sequence of human RAC3. Moreover, nucleic acid molecules encoding RAC3 proteins from different species, and thus which have a nucleotide sequence which differs from the RAC3 sequences of SEQ ID NO:1 are intended to be within the scope of the invention. For example, RAC3 cDNAs can be identified from other organisms based on the nucleotide sequence of a human RAC3.

Nucleic acid molecules corresponding to natural allelic variants and homologues of the RAC3 cDNAs of the invention can be isolated based on their homology to the RAC3 nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1. In other embodiment, the nucleic acid is at least about 30, 50, 100, 250, 500, 600, 700, or 1000 nucleotides in length nucleotides in length. As used herein, the term "hybridizes under stringent conditions" is intended to describe conditions for hybridization and washing under which nucleotide sequences at least 70% homologous to each other typically remain hybridized to each other. Preferably, the conditions are such that sequences at least about 80%, more preferably at least about 85%, even more preferably at least about 90% or 95% homologous to each other typically remain hybridized to each other. Such stringent conditions are known to those skilled in the art and can be found in Current Protocols in Molecular Biology, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Additional exemplary high stringency conditions include hybridization at about 42° C. and about 50% formamide, a first wash at about 65° C., in about 2×SSC and 1% SDS, followed by a second wash at about 65° C. in about 1×SSC and 0.1% SDS. Lower stringency conditions for detecting RAC3 genes having about 85% sequence identity to the RAC3 genes described herein include, for example, hybridization at about 42° C. in the absence of formamide, a first wash at about 42° C., in about 6×SSC and about 1% SDS, and a second wash at about 50° C., in about 6×SSC and about 1% SDS. Preferably, an isolated nucleic acid molecule of the invention that hybridizes under stringent conditions to the sequence of SEQ ID NO:1, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the RAC3 sequences that may exist in the population, the skilled artisan will further appreciate that changes can be introduced by mutation into the nucleotide sequences of SEQ ID NO:1, thereby leading to changes in the amino acid sequence of the encoded RAC3 proteins, without altering the functional ability of the RAC3 proteins. For example, nucleotide substitutions leading to amino acid substitutions at "non-essential" amino acid residues can be made in the sequence of SEQ ID NO:1. A "non-essential" amino acid residue is a residue that can be altered from the wild-type sequence of RAC3 (e.g., the sequence of SEQ ID NO:2) without altering the biological activity, whereas an "essential" amino acid residue is required for biological activity. For example, amino acid residues that are conserved among proteins related to RAC3 or comprise a RAC3 domain, are predicted to be particularly unamenable to alteration (e.g., the bHLH domain, the PAS domain, and the Q rich domains, conserved among RAC3, TIF2, and SRC-1). Moreover, amino acid residues that comprise the transcriptional activating domains or the nuclear receptor interacting domains are particularly unamenable to alteration.

Accordingly, another aspect of the invention pertains to nucleic acid molecules encoding RAC3 proteins that contain changes in amino acid residues that are not essential for activity. Such RAC3 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2. Preferably, the protein encoded by the nucleic acid molecule is at least about 65–70% homologous to SEQ ID NO:2, more preferably at least about 75–80% homologous to SEQ ID NO:2, even more preferably at least about 85–90% homologous to SEQ ID NO:2, and most preferably at least about 95% homologous to SEQ ID NO:2.

An isolated nucleic acid molecule encoding a RAC3 protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a RAC3 protein is preferably replaced with another amino acid residue from the same side chain family. Alternatively, in another embodiment, mutations can be introduced randomly along all or part of a RAC3 coding sequence, such as by saturation mutagenesis, and the resultant mutants can be screened for RAC3 biological activity to identify mutants that retain activity. Following mutagenesis of SEQ ID NO:1, the encoded protein can be expressed recombinantly and the activity of the protein can be determined.

In a preferred embodiment, a mutant RAC3 protein can be assayed for binding to RAC3 target molecules, for activation of steroid hormone-mediated transcription, or for listone acetyltransferase activity.

In addition to the nucleic acid molecules encoding RAC3 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire RAC3 coding strand, or to only a portion thereof. In one embodiment, an antisense nucleic acid molecule is antisense to a "coding region" of the coding strand of a nucleotide sequence encoding RAC3. The term "coding region" refers to the region of the nucleotide sequence comprising codons which are translated into amino acid residues (e.g., the coding region of human RAC3 corresponds to amino acids about 1–1417 of SEQ ID NO:2). In another embodiment, the antisense nucleic acid molecule is antisense to a "noncoding region" of the coding strand of a nucleotide sequence encoding RAC3. The term "noncoding region" refers to 5' and 3' sequences which flank the coding region that are not translated into amino acids (i.e., also referred to as 5' and 3' untranslated regions).

Given the coding strand sequences encoding RAC3 disclosed herein, antisense nucleic acids of the invention can be designed according to the rules of Watson and Crick base pairing. The antisense nucleic acid molecule can be complementary to the entire coding region of RAC3 mRNA, but more preferably is an oligonucleotide which is antisense to only a portion of the coding or noncoding region of RAC3 mRNA. For example, the antisense oligonucleotide can be complementary to the region surrounding the translation start site of RAC3 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a RAC3 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave RAC3 mRNA transcripts to thereby inhibit translation of RAC3 mRNA. A ribozyme having specificity for a RAC3-encoding nucleic acid can be designed based upon the nucleotide sequence of a RAC3 cDNA disclosed herein (i.e., SEQ ID NO:1. For example, a derivative of a Tetrahymena L-19 IVS RNA can be constructed in which the nucleotide sequence of the active site is complementary to the nucleotide sequence to be cleaved in a RAC3-encoding mRNA. See, e.g., Cech et al. U.S. Pat. No. 4,987,071; and Cech et al. U.S. Pat. No. 5,116,742. Alternatively, RAC3 mRNA can be used to select a catalytic RNA having a specific ribonuclease activity from a pool of RNA molecules. See, e.g., Bartel, D. and Szostak, J. W. (1993) *Science* 261:1411–1418.

Alternatively, RAC3 gene expression can be inhibited by targeting nucleotide sequences complementary to the regulatory region of the RAC3 (e.g., the RAC3 promoter and/or enhancers) to form triple helical structures that prevent transcription of the RAC3 gene in target cells. See generally, Helene, C. (1991) *Anticancer Drug Des.* 6(6):569–84;

Helene, C. et al. (1992) *Ann. N.Y. Acad. Sci.* 660:27–36; and Maher, L. J. (1992) *Bioassays* 14(12):807–15.

In yet another embodiment, the RAC3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93: 14670–675.

PNAs of RAC3 nucleic acid molecules can be used therapeutic and diagnostic applications. For example, PNAs can be used as antisense or antigene agents for sequence-specific modulation of gene expression by, for example, inducing transcription or translation arrest or inhibiting replication. PNAs of RAC3 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of RAC3 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of RAC3 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl) amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric moleclues can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated RAC3 Proteins and Anti-RAC3 Antibodies

One aspect of the invention pertains to isolated RAC3 proteins, and biologically active portions thereof, as well as polypeptide fragments suitable for use as immunogens to raise anti-RAC3 antibodies. In one embodiment, native RAC3 proteins can be isolated from cells or tissue sources by an appropriate purification scheme using standard protein purification techniques. In another embodiment, RAC3 proteins are produced by recombinant DNA techniques. Alternative to recombinant expression, a RAC3 protein or polypeptide can be synthesized chemically using standard peptide synthesis techniques.

An "isolated" or "purified" protein or biologically active portion thereof is substantially free of cellular material or other contaminating proteins from the cell or tissue source from which the RAC3 protein is derived, or substantially free from chemical precursors or other chemicals when chemically synthesized. The language "substantially free of cellular material" includes preparations of RAC3 protein in which the protein is separated from cellular components of the cells from which it is isolated or recombinantly produced. In one embodiment, the language "substantially free of cellular material" includes preparations of RAC3 protein having less than about 30% (by dry weight) of non-RAC3 protein (also referred to herein as a "contaminating protein"), more preferably less than about 20% of non-RAC3 protein, still more preferably less than about 10% of non-RAC3 protein, and most preferably less than about 5% non-RAC3 protein. When the RAC3 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of RAC3 protein in which the protein is separated from chemical precursors or other chemicals which are involved in the synthesis of the protein. In one embodiment, the language "substantially free of chemical precursors or other chemicals" includes preparations of RAC3 protein having less than about 30% (by dry weight) of chemical precursors or non-RAC3 chemicals, more preferably less than about 20% chemical precursors or non-RAC3 chemicals, still more preferably less than about 10% chemical precursors or non-RAC3 chemicals, and most preferably less than about 5% chemical precursors or non-RAC3 chemicals.

Biologically active portions of a RAC3 protein include peptides comprising amino acid sequences sufficiently homologous to or derived from the amino acid sequence of the RAC3 protein, e.g., the amino acid sequence shown in SEQ ID NO:2, which include less amino acids than the full length RAC3 proteins, and exhibit at least one activity of a RAC3 protein. Typically, biologically active portions comprise a domain or motif with at least one activity of the RAC3 protein. A biologically active portion of a RAC3 protein can be a polypeptide which is, for example, about 10, 25, 50, 100, 140, 160, 250, or 500 or more amino acids in length. Exemplary RAC3 polypeptide fragments include portions of a RAC3 polypeptide that bind to a polypeptide, especially steroid/nuclear receptors (e.g. the AF-2 region of a steroid/nuclear receptor). Fragments, for example, all or part of the RAC3 bHLH, PAS, N-terminal nuclear receptor interacting, or C terminal transcription activating domains are useful as antagonists or agonists, and are also useful as immunogens for producing antibodies that neutralize the activity of RAC3. Fragments of RAC3 not directly involved in binding are also useful. For example, such fragments are used to generate antibodies useful for detecting RAC3 or that change the binding characteristics of RAC3 without directly interacting with the binding site.

Candidate fragments can be tested for interaction with a steroid receptor, or their ability to modulate a RAC3-mediated physiological response, e.g., to serve as RAC3 agonists, by any of the assays described herein. Fragments can also be tested for their ability to antagonize the interaction between a RAC3 polypeptide and a nuclear receptor using the assays described herein. Useful analogs of RAC3 fragments (as described above) can also be produced and tested for efficacy as antagonists or agonists. Assays for analogs are performed by assays, for example, adding candidate components to a test system such as that described in the appended examples. Candidate analogs are also tested in binding assays that are known in the art. For example, a compound can be tested for its ability to displace a labeled RAC3 molecule from binding to a liganded target receptor. Other candidate molecules for modulators of a RAC3-mediated physiological response are also tested in this manner.

It is to be understood that a preferred biologically active portion of a RAC3 protein of the present invention may contain at least one of the above-identified structural domains. A more preferred biologically active portion of a RAC3 protein may contain at least two of the above-identified structural domains. Moreover, other biologically active portions, in which other regions of the protein are deleted, can be prepared by recombinant techniques and evaluated for one or more of the functional activities of a native RAC3 protein. In particularly preferred embodiments a RAC3 protein comprises both a steroid hormone receptor inteacting domain and a transcriptional activator domain.

In a preferred embodiment, the RAC3 protein has an amino acid sequence shown in SEQ ID NO:2. In other embodiments, the RAC3 protein is substantially homologous to SEQ ID NO:2, retains the functional activity of the protein of SEQ ID NO:2, yet differs in amino acid sequence due to natural allelic variation or mutagenesis, as described in detail in subsection I above. Accordingly, in another embodiment, the RAC3 protein is a protein which comprises an amino acid sequence at least about 60% homologous to the amino acid sequence of SEQ ID NO:2, and retains the functional activity of the RAC3 proteins of SEQ ID NO:2. Preferably, the protein is at least about 70% homologous to SEQ ID NO:2, more preferably at least about 80% homologous to SEQ ID NO:2, even more preferably at least about 90% homologous to SEQ ID NO:2, and most preferably at least about 95% or more homologous to SEQ ID NO:2.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the RAC3 amino acid sequence of SEQ ID NO:2 having 99 amino acid residues, at least 30, preferably at least 40, more preferably at least 50, even more preferably at least 59, and even more preferably at least 69, 79, or 89 are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed performed with the NBLAST program, score=100, wordlength=12 to obtain nucleotide sequences homologous to RAC3 nucleic acid molecules of the invention. BLAST protein searches can be performed with the XBLAST program, score=50, wordlength=3 to obtain amino acid sequences homologous to RAC3 protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The invention also provides RAC3 chimeric or fusion proteins. As used herein, a RAC3 "chimeric protein" or "fusion protein" comprises a RAC3 polypeptide operatively linked to a non-RAC3 polypeptide. A "RAC3 polypeptide" refers to a polypeptide having an amino acid sequence corresponding to RAC3, whereas a "non-RAC3 polypeptide" refers to a polypeptide having an amino acid sequence corresponding to a protein which is not substantially homologous to the RAC3 protein, e.g., a protein which is different from the RAC3 protein and which is derived from the same or a different organism. Within a RAC3 fusion protein the RAC3 polypeptide can correspond to all or a portion of a RAC3 protein. In a preferred embodiment, a RAC3 fusion protein comprises at least one biologically active portion of a RAC3 protein. In another preferred embodiment, a RAC3 fusion protein comprises at least two biologically active portions of a RAC3 protein. Within the fusion protein, the term "operatively linked" is intended to indicate that the RAC3 polypeptide and the non-RAC3 polypeptide are fused in-frame to each other. The non-RAC3 polypeptide can be fused to the N-terminus or C-terminus of the RAC3 polypeptide.

For example, in one embodiment, the fusion protein is a GST-RAC3 fusion protein in which all or a portion of a RAC3 sequence is fused to the C-terminus of the GST sequences. Such fusion proteins can facilitate the purification of recombinant RAC3. In another emobidiment all or a portion of a RAC3 sequence can be fused to a heterologous DNA binding domain, e.g., a Gal 4 DNA binding domain.

In yet another embodiment, the fusion protein comprises RAC3 sequences (e.g., a preferred RAC3 structural domain) fused to sequences from a non-RAC3 protein. The RAC3 fusion proteins of the invention can be incorporated into pharmaceutical compositions and administered to a subject to inhibit an interaction between a RAC3 and a RAC3 target molecule, to thereby suppress RAC3-mediated activation of steroid hormone mediated transcription in vivo. The RAC3 fusion proteins can be used to affect the bioavailability of a RAC3 target molecule. The RAC3 fusion proteins of the invention can further be used to inhibit an interaction between a transcriptional coactivator of steroid nuclear receptors other than a RAC3 of the present invention and a steroid hormone receptor, to thereby suppress steroid hormone mediated transcription in vivo. Use of RAC3 fusion proteins may be useful therapeutically for the treatment of disorders involving steroid/nuclear hormones and their receptors e.g., carrier. Moreover, the RAC3-fusion proteins of the invention can be used to purify RAC3 ligands and in screening assays to identify molecules which modulate the interaction of RAC3 with a RAC3 ligand.

Preferably, a RAC3 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A RAC3-encoding nucleic acid can be cloned into such an expression vector such that the fusion moiety is linked in-frame to the RAC3 protein.

The present invention also pertains to variants of the RAC3 proteins which function as either RAC3 agonists (mimetics) or as RAC3 antagonists. Variants of the RAC3 proteins can be generated by mutagenesis, e.g., discrete point mutation or truncation of a RAC3 protein. An agonist of the RAC3 proteins can retain substantially the same, or a subset, of the biological activities of the naturally occurring form of a RAC3 protein. An antagonist of a RAC3 protein can inhibit one or more of the activities of the naturally occurring form of the RAC3 protein by, for example, competitively binding to a RAC3 target molecule. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the RAC3 protein.

In one embodiment, variants of a RAC3 protein which function as either RAC3 agonists (mimetics) or as RAC3 antagonists can be identified by screening combinatorial libraries of mutants, e.g., truncation mutants, of a RAC3 protein for RAC3 protein agonist or antagonist activity. In one embodiment, a variegated library of RAC3 variants is generated by combinatorial mutagenesis at the nucleic acid level and is encoded by a variegated gene library. A variegated library of RAC3 variants can be produced by, for example, enzymatically ligating a mixture of synthetic oligonucleotides into gene sequences such that a degenerate set of potential RAC3 sequences is expressible as individual polypeptides, or alternatively, as a set of larger fusion proteins (e.g., for phage display) containing the set of RAC3 sequences therein. There are a variety of methods which can be used to produce libraries of potential RAC3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential RAC3 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a RAC3 protein coding sequence can be used to generate a variegated population of RAC3 fragments for screening and subsequent selection of variants of a RAC3 protein. In one embodiment, a library of coding sequence fragments can be generated by treating a double stranded PCR fragment of a RAC3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the RAC3 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of RAC3 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify RAC3 variants (Arkin and Yourvan (1992) *PNAS* 89:7811–7815; Delgrave et al. (1993) *Protein Engineering* 6(3):327–331).

In one embodiment, cell based assays can be exploited to analyze a variegated RAC3 library; For example, a library of expression vectors can be transfected into a cell line which ordinarily responds to a particular ligand in a RAC3-dependent manner. The transfected cells are then contacted with the ligand and the effect of expression of the mutant on signaling by the ligand can be detected, e.g., by measuring any of a number of inflammatory or angiogenic responses. Plasmid DNA can then be recovered from the cells which score for inhibition, or alternatively, potentiation of ligand induction, and the individual clones further characterized.

An isolated RAC3 protein, or a portion or fragment thereof, can be used as an immunogen to generate antibodies that bind RAC3 using standard techniques for polyclonal and monoclonal antibody preparation. A full-length RAC3 protein can be used or, alternatively, the invention provides antigenic peptide fragments of RAC3 for use as immunogens. The antigenic peptide of RAC3 comprises at least 8 amino acid residues of the amino acid sequence shown in SEQ ID NO:2, and encompasses an epitope of RAC3 such that an antibody raised against the peptide forms a specific immune complex with RAC3. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of RAC3 that are located on the surface of the protein, e.g., hydrophilic regions.

A RAC3 immunogen typically is used to prepare antibodies by immunizing a suitable subject, (e.g., rabbit, goat, mouse or other mammal) with the immunogen. An appropriate immunogenic preparation can contain, for example, recombinantly expressed RAC3 protein or a chemically synthesized RAC3 polypeptide. The preparation can further include an adjuvant, such as Freund's complete or incomplete adjuvant, or similar immunostimulatory agent. Immunization of a suitable subject with an immunogenic RAC3 preparation induces a polyclonal anti-RAC3 antibody response.

Accordingly, another aspect of the invention pertains to anti-RAC3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as RAC3. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind RAC3. The term "monoclonal antibody" or "monoclonal antibody composition", as used herein, refers to a population of antibody molecules that contain only one species of an antigen binding site capable of immunoreacting with a particular epitope of RAC3. A monoclonal antibody composition thus typically displays a single binding affinity for a particular RAC3 protein with which it immunoreacts.

Polyclonal anti-RAC3 antibodies can be prepared as described above by immunizing a suitable subject with a RAC3 immunogen. The anti-RAC3 antibody titer in the immunized subject can be monitored over time by standard techniques, such as with an enzyme linked immunosorbent assay (ELISA) using immobilized RAC3. If desired, the antibody molecules directed against RAC3 can be isolated from the mammal (e.g., from the blood) and further purified by well known techniques, such as protein A chromatography to obtain the IgG fraction. At an appropriate time after immunization, e.g., when the anti-RAC3 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem* 0.255: 4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a RAC3 immunogen as described above, and the culture supernatants of the resulting hybridoma cells are screened to identify a hybridoma producing a monoclonal antibody that binds RAC3.

Any of the many well known protocols used for fusing lymphocytes and immortalized cell lines can be applied for the purpose of generating an anti-RAC3 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/ 1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind RAC3, e.g., using a standard ELISA assay.

Alternative to preparing monoclonal antibody-secreting hybridomas, a monoclonal anti-RAC3 antibody can be identified and isolated by screening a recombinant combinatorial immunoglobulin library (e.g., an antibody phage display library) with RAC3 to thereby isolate immunoglobulin library members that bind RAC3. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226: 889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348: 552–554.

Additionally, recombinant anti-RAC3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-RAC3 antibody (e.g., monoclonal antibody) can be used to isolate RAC3 by standard techniques, such as affinity chromatography or immunoprecipitation. An anti-RAC3 antibody can facilitate the purification of natural RAC3 from cells and of recombinantly produced RAC3 expressed in host cells. Moreover, an anti-RAC3 antibody can be used to detect RAC3 protein (e.g., in a cellular lysate) in order to evaluate the abundance and pattern of expression of the RAC3 protein. Anti-RAC3 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a RAC3 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., RAC3 proteins, mutant forms of RAC3 proteins, fusion proteins, etc.).

The recombinant expression vectors of the invention can be designed for expression of RAC3 proetins in prokaryotic or eukaryotic cells. For example, RAC3 proteins can be expressed in bacterial cells such as E. coli, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in RAC3 activity assays, in RAC3 ligand binding (e.g., direct assays or competitive assays described in detail below), to generate antibodies specific for RAC3 proteins, as examples. In a preferred embodiment, a RAC3 fusion protein expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion E. coli expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., *Gene Expression Technology. Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

In another embodiment, the RAC3 expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, RAC3 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual.* 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

If desired, recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). A DHFR-deficient CHO cell line (e.g., CHO DHFR⁻ cells, ATCC Accession No. CRL 9096) is among the host cells preferred for DHFR selection of a stably-transfected cell line or DHFR-mediated gene amplification.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to RAC3 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics, Vol.* 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a RAC3 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a RAC3 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a RAC3 protein. Accordingly, the invention further provides methods for producing a RAC3 protein using the host cells of the invention. In one embodiment, the method comprises culturing the host cell of invention (into which a recombinant expression vector encoding a RAC3 protein has been introduced) in a suitable medium such that a RAC3 protein is produced. In another embodiment, the method further comprises isolating a RAC3 protein from the medium or the host cell.

Once a recombinant RAC3 polypeptide is expressed, it is isolated, e.g., using affinity chromatography. In one example, isolation is facilitated by inclusion in the RAC3 polypeptide of a leader sequence or "tag" that allows RAC3 polypeptide capture (for example, the GST sequence described herein). In another example, the RAC3 polypeptide product is isolated using an anti-RAC3 polypeptide antibody (e.g., produced as described herein). This antibody can be attached to a solid support (e.g., to cyanogen bromide-activated Sepharose) or can be used in immunoprecipitation methods to bind and isolate the RAC3 polypeptide of interest (see, e.g., J. E. Coligan et al., *Current Protocols in Immunology,* 1994, John Wiley and Sons, Inc). Lysis and fractionation of RAC3 polypeptide-harboring cells prior to affinity chromatography can be performed by any standard method (see, e.g., Ausubel et al., supra). Once isolated, the recombinant protein can, if desired, be further purified, e.g., by high performance liquid chromatography (HPLC; see, e.g., Fisher, *Laboratory Techniques in Biochemistry and Molecular Biology,* eds., Work and Burdon, Elsevier, 1980). These general techniques of polypeptide expression and purification can also be used to produce and isolate useful RAC3 polypeptide fragments or analogs (as described herein).

The host cells of the invention can also be used to produce nonhuman transgenic animals. For example, in one embodiment, a host cell of the invention is a fertilized oocyte or an embryonic stem cell into which RAC3-coding sequences have been introduced. Such host cells can then be used to create non-human transgenic animals in which exogenous RAC3 sequences have been introduced into their genome or homologous recombinant animals in which endogenous RAC3 sequences have been altered. Such animals are useful for studying the function and/or activity of a RAC3 and for identifying and/or evaluating modulators of RAC3 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous RAC3 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a RAC3-encoding nucleic acid into the male pronuclei of a fertilized oocyte, e.g., by microinjection, retroviral infection, and allowing the oocyte to develop in a pseudopregnant female foster animal. The RAC3 cDNA sequence of SEQ ID NO:1 can be introduced as a transgene into the genome of a non-human animal. Intronic sequences and polyadenylation signals can also be included in the transgene to increase the efficiency of expression of the transgene. A tissue-specific regulatory sequence(s) can be operably linked to a RAC3 transgene to direct expression of a RAC3 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a RAC3 transgene in its genome and/or expression of RAC3 mRNA in tissues or cells of the animals. A transgenic founder animal can then be used to breed additional animals carrying the transgene. Moreover, transgenic animals carrying a transgene encoding a RAC3 protein can further be bred to other transgenic animals carrying other transgenes.

To create a homologous recombinant animal, a vector is prepared which contains at least a portion of a RAC3 gene into which a deletion, addition or substitution has been introduced to thereby alter, e.g., functionally disrupt, the RAC3 gene. The RAC3 gene can be a human gene (e.g., the cDNA of SEQ ID NO:1). In a preferred embodiment, the vector is designed such that, upon homologous recombination, the endogenous RAC3 gene is functionally disrupted (i.e., no longer encodes a functional protein; also referred to as a "knock out" vector). Alternatively, the vector can be designed such that, upon homologous recombination, the endogenous RAC3 gene is mutated or otherwise altered but still encodes functional protein (e.g., the upstream regulatory region can be altered to thereby alter the expression of the endogenous RAC3 protein). In the homologous recombination vector, the altered portion of the RAC3 gene is flanked at its 5' and 3' ends by additional nucleic acid sequene of the RAC3 gene to allow for homologous recombination to occur between the exogenous RAC3 gene carried by the vector and an endogenous RAC3 gene in an embryonic stem cell. The additional flanking RAC3 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced RAC3 gene has homologously recombined with the endogenous RAC3 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The RAC3 nucleic acid molecules, RAC3 proteins, and anti-RAC3 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a RAC3 protein or anti-RAC3 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a RAC3 protein of the invention has one or more of the following activities: binding to a RAC3 target molecule, the activation of steroid hormone-mediated transcription, and listone acetyltransferase activity. For example, modulation of RAC3 can be useful in anti-cancer gene therapy and disorders involving steroid/nuclear hormones. For example, to treat a malignancy involving RAC3. A functional RAC3 gene can be introduced into cells at the site of a tumor. The sensitivity of trumors to hormone-based treatment regimens can be increased by introducing a functional RAC3 gene into tumor cells. In the case of disorders of steroid/nuclear hormone systems, it is desirable to target RAC3 to hormone target tissues. In other embodiments, antisense nucleic acid could be used ot decrease RAC3 expression or a dominant negative mutant of RAC3 could be introduced to block hormonal stimulation, e.g. in a tumor.

The isolated nucleic acid molecules of the invention can be used, for example, to express RAC3 protein (e.g., via a recombinant expression vector in a host cell in gene therapy applications), to detect RAC3 mRNA (e.g., in a biological sample) or a genetic alteration in a RAC3 gene, and to modulate RAC3 activity, as described further below. The RAC3 proteins can be used to treat disorders characterized by insufficient or excessive activation of steroid/nuclear hormone receptors. In addition, the RAC3 proteins can be used to screen drugs or compounds which modulate the RAC3 activity as well as to treat disorders characterized by insufficient or excessive production of RAC3 protein or production of RAC3 protein forms which have decreased or aberrant activity compared to RAC3 wild type protein. Moreover, the anti-RAC3 antibodies of the invention can be used to detect and isolate RAC3 proteins, regulate the bioavailability of RAC3 proteins, and modulate RAC3 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to RAC3 proteins, have a stimulatory or inhibitory effect on, for example, RAC3 expression or RAC3 activity, or have a stimulatory or inhibitory effect on, for example, the expression or activity of a non-RAC3 transcriptional coactivator of steroid nuclear receptors.

In one embodiment, the invention provides assays for screening candidate or test compounds which bind to or modulate the activity of a RAC3 protein or polypeptide or biologically active portion thereof. In another embodiment, the invention provides assays for screening candidate or test compounds which bind to or modulate the activity of a RAC3 target molecule. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection.

Candidate modulators can be purified (or substantially purified) molecules or can be one component of a mixture of compounds (e.g., an extract or supernatant obtained from cells; Ausubel et al., supra). In a mixed compound assay, RAC3 expression is tested against progressively smaller subsets of the candidate compound pool (e.g., produced by standard purification techniques, e.g., HPLC or FPLC) until a single compound or minimal compound mixture is demonstrated to modulate RAC3 expression.

Candidate RAC3 modulators include peptide as well as non-peptide molecules (e.g., peptide or non-peptide molecules found, e.g., in a cell extract, mammalian serum, or growth medium on which mammalian cells have been cultured).

The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al.(1990) *Proc. Natl. Acad. Sci.* 87:6378–6382); (Felici (1991) *J. Mol. Biol.* 222:301–310); (Ladner supra.).

Determining the ability of the RAC3 protein to bind to or interact with a RAC3 target molecule can be accomplished by one of numerous methods, for example, by coupling the test compound with a radioisotope or enzymatic label such that binding of the test compound to the RAC3 can be determined by detecting the labeled compound in a complex. For example, test compounds can be labeled with $^{125}$I, $^{35}$S, 14C, or $^3$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a preferred embodiment, the assay comprises contacting a cell which expresses RAC3 with a RAC3 target molecule or a biologically-active portion thereof, to form an assay mixture, contacting the assay mixture with a test compound, and determining the ability of the test compound to modulate the interaction between RAC3 and the target molecule, wherein determining the ability of the test compound to modulate the interaction comprises determining the ability of the test compound to preferentially bind to RAC3 as compared to the ability of the target molecule to bind RAC3, or a biologically active portion thereof, to bind to the receptor.

In another embodiment, an assay is a cell-based assay comprising contacting a cell expressing a RAC3 target molecule with a test compound and determining the ability of the test compound to modulate (e.g. stimulate or inhibit) the activity of the RAC3 target molecule. Determining the ability of the test compound to modulate the activity of the RAC3 target molecule can be accomplished, for example, by determining the effect of the compound on the ability of RAC3 to bind to or interact with the RAC3 target molecule. As used herein, a "target molecule" is a molecule with which RAC3 protein binds or interacts in nature, for example, a steriod/nuclear hormone receptor.

Determining the ability of the RAC3 protein to bind to or interact with a RAC3 target molecule can be accomplished by one of the methods described above for determining direct binding. In a preferred embodiment, determining the ability of the RAC3 protein to bind to or interact with a RAC3 target molecule can be accomplished by determining the activity of the target molecule. For example, the activity of the target molecule can be determined by detecting changes in steroid hormone receptor-mediated transcription.

In certain embodiments of the above assay methods of the present invention, it may be desirable to immobilize either RAC3 or its target molecule to facilitate separation of complexed from uncomplexed forms of one or both of the proteins, as well as to accommodate automation of the assay. Binding of a test compound to RAC3, or interaction of RAC3 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/RAC3 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or RAC3 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of RAC3 binding or activity determined using standard techniques.

Other techniques for immobilizing proteins on matrices can also be used in the screening assays of the invention. For example, either RAC3 or its target molecule can be immobilized utilizing conjugation of biotin and streptavidin. Biotinylated RAC3 or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with RAC3 or target molecules but which do not interfere with binding of the RAC3 protein to its target molecule can be derivatized to the wells of the plate, and unbound target or RAC3 trapped in the wells by antibody conjugation. Methods for detecting such complexes, in addition to those described above for the GST-immobilized complexes, include immunodetection of complexes using antibodies reactive with the RAC3 or target molecule, as well as enzyme-linked assays which rely on detecting an enzymatic activity associated with the RAC3 or target molecule.

In another embodiment, modulators of RAC3 expression are identified in a method wherein a cell is contacted with a candidate compound and the expression of RAC3 mRNA or protein in the cell is determined. The level of expression of RAC3 mRNA or protein in the presence of the candidate compound is compared to the level of expression of RAC3 mRNA or protein in the absence of the candidate compound. The candidate compound can then be identified as a modulator of RAC3 expression based on this comparison. For example, when expression of RAC3 mRNA or protein is greater (statistically significantly greater) in the presence of the candidate compound than in its absence, the candidate compound is identified as a stimulator of RAC3 mRNA or protein expression. Alternatively, when expression of RAC3 mRNA or protein is less (statistically significantly less) in the presence of the candidate compound than in its absence, the candidate compound is identified as an inhibitor of RAC3 mRNA or protein expression. The level of RAC3 mRNA or protein expression in the cells can be determined by methods described herein for detecting RAC3 mRNA or protein.

In yet another aspect of the invention, the RAC3 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with RAC3 ("RAC3-binding proteins" or "RAC3-bp" or "target molecules) and are involved in RAC3 activity as described in the appended example.

The two-hybrid system is based on the modular nature of most transcription factors, which consist of separable DNA-binding and activation domains. Briefly, the assay utilizes two different DNA constructs. In one construct, the gene that codes for a RAC3 protein or a protion of a RAC3 protein, e.g. a receptor interacting domain is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a RAC3-dependent complex, the DNA-binding and activation domains of the transcription factor are brought into close proximity. This proximity allows transcription of a reporter gene (e.g., LacZ or β gal) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the RAC3 protein. In preferred embodiments a ligand for the steroid/nuclear receptor can be added to the assay to enhance the binding of RAC3 to the steroid/nuclear receptor. In these embodiments compounds that inhibit or downmodulate the interaction among RAC3, the ligand, and the receptor can be identified by reduction in reporter gene readout when compared to the reporter gene readout in the absence of compound.

In other preferred embodiments the ligand-enhanced binding of RAC3 to steroid/nuclear hormone receptors can be exploited to discover novel compounds which can act have a steroid hormone activity. In such embodiments, ligand is omitted from the assay and compounds which enhance the interaction among RAC3 and the receptor can be identified by enhancing the reporter gene readout when compared to the reporter gene readout in the absence of compound.

This invention further pertains to novel agents identified by the above-described screening assays. A molecule that modulates RAC3 expression or activity is considered useful in the invention; such a molecule can be used, for example, as a therapeutic to modulate cellular levels of RAC3 or to modulate a RAC3 activity.

Furthermore, a molecule that promotes an increase in RAC3 expression or activity is useful for increasing the efficacy of steroid/lipid soluble hormone treatments of disorders, for example, inflammatory disorders treated with glucocorticoids. RAC3 agonists should also be helpful for treatment of disorders due to hormone deficiencies including those due to decreased ligand uptake or receptor variants which do not bind ligands efficiently (e.g., certain forms of night blindness).

A molecule that promotes a decrease in RAC3 expression or activity is also considered useful in the invention. Such a molecule can be used, for example, as a therapeutic to decrease cellular levels of RAC3 or to decrease RAC3 binding activity and thereby decrease the activity of certain nuclear/steroid receptors. Since a decrease in RAC3 expression or activity results in lower activity of steroid/nuclear receptors, a molecule that decreases steroid/nuclear receptor activity by modulating RAC3 activity or binding is useful for down regulating steroid/nuclear receptor activity and gene expression. Thus, a molecule that promotes a decrease in RAC3 activity is useful in a variety of situations for treating a variety of hormone-induced and hormone-related disorders, e.g. cancer.

Accordingly, it is within the scope of this invention to further use an agent identified as described herein in an appropriate animal model. For example, an agent identified as described herein (e.g., a RAC3 modulating agent, an antisense RAC3 nucleic acid molecule, a RAC3-specific antibody, a RAC3-binding partner or a novel compound which has steroid activity or inhibits a steroid activity) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

Diagnostic Assays

An exemplary method for detecting the presence or absence of RAC3 protein or nucleic acid in a biological sample involves obtaining a biological sample from a test subject and contacting the biological sample with a compound or an agent capable of detecting RAC3 protein or nucleic acid (e.g., mRNA, genomic DNA) that encodes RAC3 protein such that the presence of RAC3 protein or nucleic acid is detected in the biological sample. A preferred agent for detecting RAC3 mRNA or genomic DNA is a labeled nucleic acid probe capable of hybridizing to RAC3 mRNA or genomic DNA. The nucleic acid probe can be, for example, a full-length RAC3 nucleic acid, such as the nucleic acid of SEQ ID NO:1 or a portion thereof, such as an oligonucleotide of at least 15, 30, 50, 100, 250 or 500 nucleotides in length and sufficient to specifically hybridize under stringent conditions to RAC3 mRNA or genomic DNA. Other suitable probes for use in the diagnostic assays of the invention are described herein.

A preferred agent for detecting RAC3 protein is an antibody capable of binding to RAC3 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect RAC3 mRNA, protein, or genomic DNA in a biological sample in vitro as well as in vivo. For example, in vitro techniques for detection of RAC3 mRNA include Northern hybridizations and in situ hybridizations. In vitro techniques for detection of RAC3 protein include enzyme linked immunosorbent assays (ELISAs), Western blots, immunoprecipitations and immunofluorescence. In vitro techniques for detection of RAC3 genomic DNA include Southern hybridizations. Furthermore, in vivo techniques for detection of RAC3 protein include introducing into a subject a labeled anti-RAC3 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting RAC3 protein, mRNA, or genomic DNA, such that the presence of RAC3 protein, mRNA or genomic DNA is detected in the biological sample, and comparing the presence of RAC3 protein, mRNA or genomic DNA in the control sample with the presence of RAC3 protein, mRNA or genomic DNA in the test sample.

The invention also encompasses kits for detecting the presence of RAC3 in a biological sample. For example, the kit can comprise a labeled compound or agent capable of detecting RAC3 protein or mRNA in a biological sample; means for determining the amount of RAC3 in the sample; and means for comparing the amount of RAC3 in the sample with a standard. The compound or agent can be packaged in a suitable container. The kit can further comprise instructions for using the kit to detect RAC3 protein or nucleic acid.

Prognostic Assays

The diagnostic methods described herein can furthermore be utilized to identify subjects having or at risk of developing a disease or disorder associated with aberrant RAC3 expression or activity. For example, the assays described herein, such as the preceding diagnostic assays or the following assays, can be utilized to identify a subject having or at risk of developing a disorder associated with RAC3 protein, nucleic acid expression or activity. For example, any disorder known to be associated with steroid hormones could be treated (See, e.g., Harrison's Principles of Internal Medicine, 13th Edition. McGraw-Hill 1996). For example, certain types of cancer can be diagnosed. Alternatively, the prognostic assays can be utilized to identify a subject having or at risk for developing cancer. Thus, the present invention provides a method for identifying a disease or disorder associated with aberrant RAC3 expression or activity in which a test sample is obtained from a subject and RAC3 protein or nucleic acid (e.g, mRNA, genomic DNA) is detected, wherein the presence of RAC3 protein or nucleic acid is diagnostic for a subject having or at risk of developing a disease or disorder associated with aberrant RAC3 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant RAC3 expression or activity. For example, such methods can be used to determine whether a subject can be effectively treated with an agent for a disorder, such as an inflammatory disorder (e.g., kidney inflammation). Alternatively, such methods can be used to determine whether a subject can be effectively treated with an agent for an inflammatory disease. Thus, the present invention provides methods for determining whether a subject can be effectively treated with an agent for a disorder associated with aberrant RAC3 expression or activity in which a test sample is obtained and RAC3 protein or nucleic acid expression or activity is detected (e.g., wherein the abundance of RAC3 protein or nucleic acid expression or activity is diagnostic for a subject that can be administered the agent to treat a disorder associated with aberrant RAC3 expression or activity.)

The methods of the invention can also be used to detect genetic alterations in a RAC3 gene, thereby determining if a subject with the altered gene is at risk for a disorder. In preferred embodiments, the methods include detecting, in a sample of cells from the subject, the presence or absence of a genetic alteration characterized by at least one of an alteration affecting the integrity of a gene encoding a RAC3-protein, or the mis-expression of the RAC3 gene. For example, such genetic alterations can be detected by ascertaining the existence of at least one of 1) a deletion of one or more nucleotides from a RAC3 gene; 2) an addition of one or more nucleotides to a RAC3 gene; 3) a substitution of one or more nucleotides of a RAC3 gene, 4) a chromosomal rearrangement of a RAC3 gene; 5) an alteration in the level of a messenger RNA transcript of a RAC3 gene, 6) aberrant modification of a RAC3 gene, such as of the methylation pattern of the genomic DNA, 7) the presence of a non-wild type splicing pattern of a messenger RNA transcript of a RAC3 gene, 8) a non-wild type level of a RAC3-protein, 9) allelic loss of a RAC3 gene, and 10) inappropriate post-translational modification of a RAC3-protein. As described herein, there are a large number of assay techniques known in the art which can be used for detecting alterations in a RAC3 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the RAC3-gene (see Abravaya et al. (1995) *Nucleic Acids Res* 0.23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a RAC3 gene under conditions such that hybridization and amplification of the RAC3-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a RAC3 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in RAC3 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in RAC3 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the RAC3 gene and detect mutations by comparing the sequence of the sample RAC3 with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the RAC3 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type RAC3 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in RAC3 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a RAC3 sequence, e.g., a wild-type RAC3 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in RAC3 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat Res* 285:125–144; and Hayashi (1992) *Genet Anal Tech Appl* 9:73–79). Single-stranded DNA fragments of sample and control RAC3 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a RAC3 gene.

Furthermore, any cell type or tissue in which RAC3 is expressed may be utilized in the prognostic assays described herein.

Methods of Treatment:

The present invention provides for both prophylactic and therapeutic methods of treating a subject at risk of (or susceptible to) a disorder or having a disorder associated with aberrant RAC3 expression or activity. Furthermore, the invention provides for both prophylactic and therapeutic methods of treating a subject at risk of (or susceptible to) a disorder or having a disorder associated with aberrant steroid/nuclear hormone expression or activity.

Therapeutic Methods

Another aspect of the invention pertains to methods of modulating RAC3 expression or activity for therapeutic purposes. It has been determined that RAC3-1 is strongly expressed in the heart, placenta, skeletal muscle, and pancreas.

Accordingly, in an exemplary embodiment, the modulatory method of the invention involves contacting a cell with a RAC3 such that the steroid/nuclear hormone mediated transcription is modulated. Alternatively, the modulatory method of the invention involves contacting a cell with a RAC3 or agent that modulates one or more of the activities of RAC3 protein activity associated with the cell. An agent that modulates RAC3 protein activity can be an agent as described herein, such as a nucleic acid or a protein, a naturally-occurring target molecule of a RAC3 protein (e.g., a carbohydrate), a RAC3 antibody, a RAC3 agonist or antagonist, a peptidomimetic of a RAC3 agonist or antagonist, or other small molecule. In one embodiment, the agent stimulates one or more RAC3 activites. Examples of such stimulatory agents include active RAC3 protein and a nucleic acid molecule encoding RAC3 that has been introduced into the cell. In another embodiment, the agent inhibits one or more RAC3 activites. Examples of such inhibitory agents include antisense RAC3 nucleic acid molecules and anti-RAC3 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a RAC3 protein or nucleic acid molecule. Alternatively, the present invention provides methods of treating an individual afflicted with a disease or disorder characterized by aberrant expression or activity of a relating to steroid/nuclear hormone mediated transcription. In one embodiment, the method involves administering an agent (e.g., an agent identified by a screening assay described herein), or combination of agents that modulates (e.g., upregulates or downregulates) RAC3 expression or activity or the expression or activity of a steroid/nuclear hormone receptor. In another embodiment, the method involves administering a RAC3 protein or nucleic acid molecule as therapy to compensate for reduced or aberrant RAC3 expression or activity. In another embodiment, the method involves administering a RAC3 protein or nucleic acid molecule as therapy to compensate for reduced or aberrant expression or activity.

Stimulation of RAC3 activity is desirable in situations in which RAC3 is abnormally downregulated and/or in which increased RAC3 activity is likely to have a beneficial effect. Likewise, inhibition of RAC3 activity is desirable in situations in which RAC3 is abnormally upregulated and/or in which decreased RAC3 activity is likely to have a beneficial effect.

This invention is further illustrated by the following examples which should not be construed as limiting. The contents of all references, patents and published patent applications cited throughout this application are hereby incorporated by reference.

EXAMPLES

Examples

A new transcriptional activator that interacts with steroid/nuclear hormone receptors was identified by a screening human brain cDNA library using a yeast two-hybrid system (Durfee et al., *Genes Dev.* 7:555–69, 1993) and the retinoic acid receptor. The protein, designated RAC3, is an AF2-dependent co-factor that enhances transcriptional activation by steroid/nuclear receptors. The experiments described below document the isolation and characterization of RAC3 as well as providing examples useful for the invention.

Example 1

Identification of a RAC3 Sequence

To perform a yeast two-hybrid screen, a plasmid vector pGBT-hRARα-expressing Gal4 DBD fusion of full-length human RARα in yeast cells was constructed and used as bait. A human brain cDNA library in pGAD10 vector (Clontech) was screened for RAR-interacting proteins as previously described in Durfee et al. (*Genes Dev.* 7: 555–569, 1993). After primary selection on synthetic dropout plates lacking tryptophan, leucine, and histidine, but supplemented with 0 50 mM of 3-aminotriazole, 20 colonies were isolated that were further tested for expression of β-galactosidase by in a liquid assay (ONPG assay; Chen et al., *Proc. Nat. Acad. Sci.* 93:7567–71, 1996) The positive clones that expressed both HIS3 and LacZ reporter genes were rescued and retransformed into yeast cells together with the original bait and other constructs. These analyses led to the identification of a single specific clone, RAC3.1.

This method is useful for the identification of additional steroid/nuclear receptor binding proteins. The method is also useful for analyzing the ability of RAC3 polypeptides to functionally interact with steroid/nuclear receptors, for example, by changing the receptor sequence used as bait.

Example 2

Isolation of Full-Length RAC3

The cDNA insert of the RAC3.1 clone was labeled with $^{32}$P-dATP using the DECAprime II DNA labeling kit (Ambion). The labeled DNA was used to screen a λgt11 human HeLa cDNA library (Clontech). Three cDNA clones covering full-length RAC3 coding region were identified and their sequences determined by dideoxynucleotide sequencing using the T7 Sequenase sequencing kit (Amersham). The sequence analysis and comparison were carried out with the GCG package from the University of Wisconsin (supra). A full-length RAC3 expression vector (pCMX.F.RAC3) was constructed in the pCMX expression vector (Umesono et al., Cell 65:1255–1266, 1991), containing a FLAG and an HA epitope linked to the N-terminus of RAC3.

This method is useful, for example, for obtaining full-length RAC3 nucleic acid sequences from other organisms.

Example 3

Sequence Analysis of RAC3

Sequence analysis revealed that the yeast two-hybrid clone RAC3.1 encodes a polypeptide of 804 amino acids (see FIG. 2, amino acids 401–1204). A database search revealed a weak similarity of RAC3 and the central domains of two recently identified steroid receptor coactivators, SRC-1 (Takeshita et al., Endocrinology 137:3594–7, 1996) and TIF2/GRIP1 (Voegel et al., EMBO J. 15:3667–75, 1996; Hong et al., Proc. Natl. Acad. Sci. USA 93:4948–52, 1996). Full-length RAC3 cDNA was then cloned and the nucleotide sequence determined (see Example 2; FIG. 1; SEQ ID NO:1). The deduced amino acid sequence indicated that the RAC3 gene encodes a polypeptide of about 1417 residues (FIGS. 1 and 2; SEQ ID NO:2). Sequence alignment of full-length RAC3, TIF2, and human SRC-1 revealed a striking homology in the N-terminal region of about 350 amino acids (about 50% identity among all three proteins). This region contains a potential basic-helix-loop-helix (bHLH) domain similar to many transcriptional regulators (Murre et al., Cell 56:777–83, 1989), and two Per-AhR-Sim (PAS) domains found in several nuclear proteins including Period (Per), aryl hydrocarbon receptor (AhR) and its heterodimeric partner ARNT, the Single Minded (Sim) sequence and the hypoxia inducible factor HIF1α (Swanson and Bradfield, Pharmacogenetics 3:213–30,1993). Sequence comparison among these bHLH/PAS containing proteins revealed that the bHLH and PAS domains in RAC3, TIF2, and SRC-1 share a greater homology among themselves than to the other proteins (FIG. 3). Thus, these three receptor-associated coactivators constitute a unique bHLH/PAS subfamily.

Figure 5:
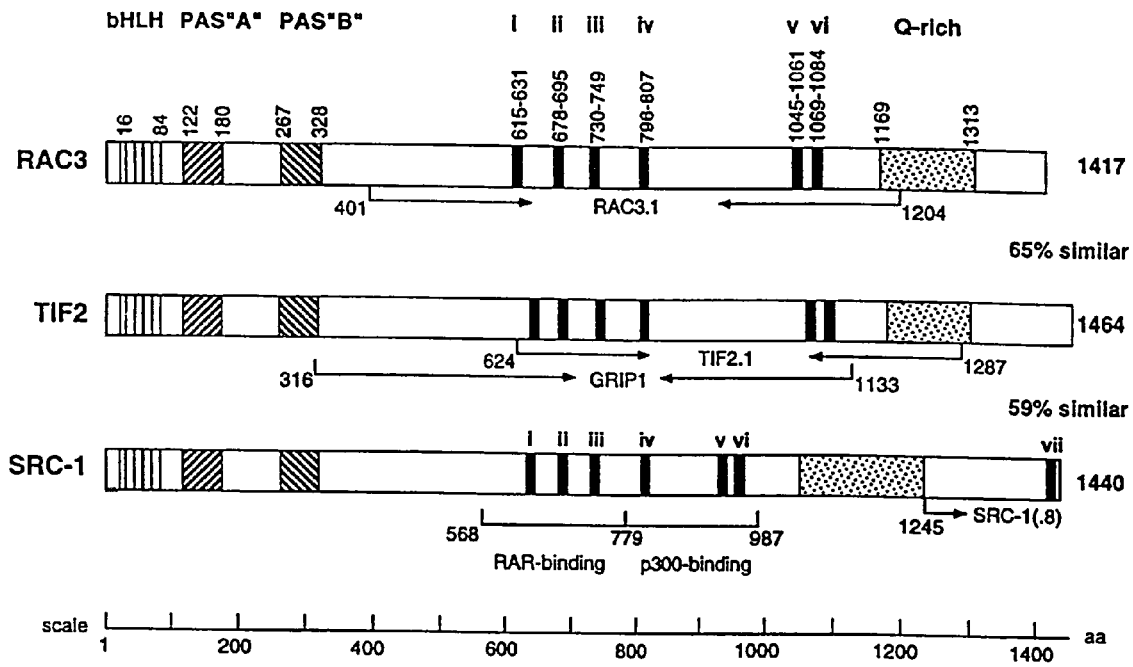
FIG. 5 is a schematic diagram of the domain structures of human RAC3, TIF2, and SRC-1

Within the RAC3.1 there are six repeated motifs sharing a consensus sequence of LXXLL or LLXXL (at about amino acids 621–625, 684–689, 737–742, 803–807, 1053–1057, and 1178–1182; FIG. 4), wherein L is leucine and X is any amino acid. These motifs and their neighboring residues are highly charged and well conserved among RAC3, TIF2, and SRC-1 (FIG. 4, i to vi). Based on predictions of secondary structure, all of the regions containing these motifs have the potential to form helices, especially with motifs iv, v, and vi. Since the region containing motifs iv, v, and vi contains both transcriptional activation and receptor-interaction activities, it is possible that these conserved regions play a role in either function. In addition, a similar motif was found at the C-terminus of SRC-1, located within the originally identified receptor-interacting domain (about amino acids 1424–1440; FIG. 4, vii). At the C-terminal domain of RAC3, a glutamine-rich (Q-rich) domain at about amino acids 1169–1313 was identified (FIG. 2). This Q-rich domain is also conserved among RAC3, TIF2, and SRC-1 and, interestingly, a stretch of 26 consecutive glutamine residues was found only in RAC3. A schematic domain structure comparison among these three proteins is shown in FIG. 5.

Example 4

Expression of RAC3

The expression of RAC3 was examined with Northern blot analysis using standard methods. A single message of about 7.5 kb was detected in human HL60 cells as well as in mouse embryonic tissues. RAC3 was up-regulated in HL60 cells treated with all-trans retinoic acid (atRA). This stimulation by atRA is a direct effect on transcription and does not require protein synthesis, since addition of cycloheximide does not have an effect on stimulation by atRA. This suggests that RAC3 not only functions as an RAR coactivator, its expression level may be directly regulated by RA. Thus, a positive feedback regulatory network may operate in which RAC3 binding to RA-RAR complex activates transcription which, in turn, increases transcription of RAC3.

In addition to providing an example of measurement of RAC3 expression, the above exemplifies a model system for studying mechanisms by which gene expression is controlled by exogenous stimuli, e.g. steroid hormones.

Expression of RAC3 in various tissues was examined by Northern analysis using known methods. RAC3 was expressed in many but not all tissues. The greatest levels of expression were seen in heart, placenta, skeletal muscle, and pancreas.

Example 5

RAC3 Interaction with Nuclear Receptors

Figure 6:
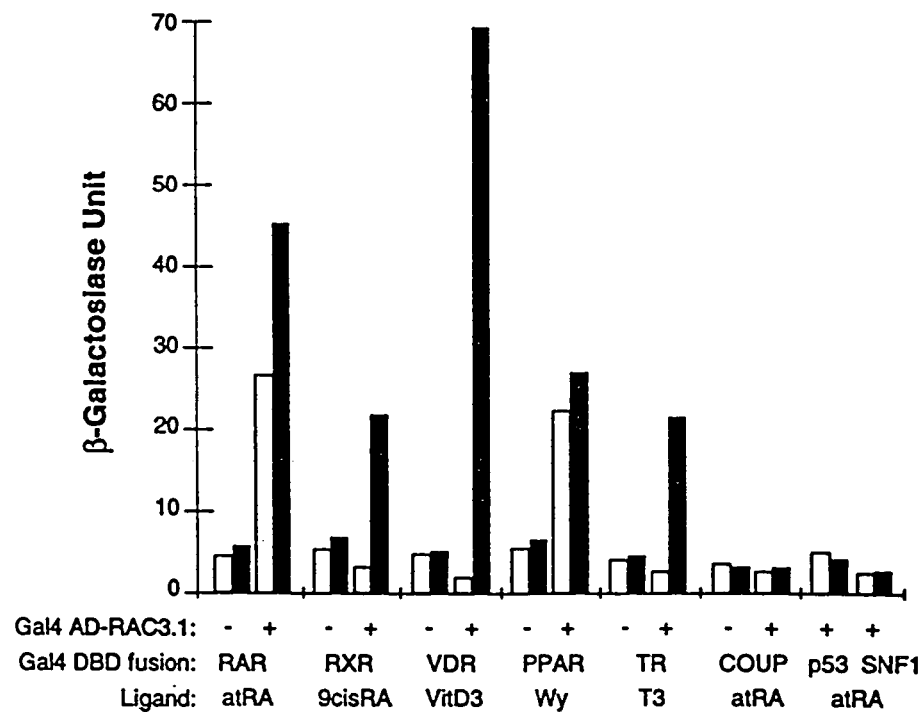
FIG. 6 is a graph of data from an experiment investigating protein—protein interactions between RAC3 and various receptors using the yeast 2-hybrid system.

The protein—protein interactions between RAC3 and several steroid/nuclear receptors were analyzed by the yeast two-hybrid system. The original two-hybrid clone, RAC3.1 in pGAD10 vector, was retransformed together with yeast expression vectors for Gal4 DBD fusion of selected hormone receptor genes into Y190 cells. The receptors used include RAR (full-length hRARα), RXR (full-length hRXRα), VDR (LBD of human Vitamin D receptor), PPAR (LBD of mPPARα), TR (LBD) of hTRβ), COUP (LBD of COUP-TFI). Three independent colonies from each transformation were selected and analyzed for expression of α-galactosidase activities by liquid ONPG assay (FIG. 6) after treatment with 1 μM of corresponding ligands (closed bars), or with equal concentration of vehicle alone (open bars). Under the conditions used in these experiments, ligand treatment did not produce detectable β-galactosidase activity from the Gal4 DBD-receptor fusion alone. The ligands used in these experiments were atRA, VitD3 (1,25-dihydroxyvitamin D$_3$), and Wy (Wy 14,642). In addition to RARα, RAC3 also interacted with RXR, VDR, PPAR, and TR, in a ligand-dependent manner. In the absence of ligand, RAC3 can interact with RAR and PPAR. Ligand treatment enhanced these interactions. RAC3 did not interact with COUP-TFI or other non-receptor proteins such as p53 and SNF1. These results identify RAC3 as a specific receptor-interacting protein which preferentially associates with selected ligand-bound nuclear receptors.

Example 6

RAC3 is an AF-2 Dependent Co-Factor of Nuclear Receptors

The ligand dependency of the interactions of RAC3 with the above selected receptors suggests that a ligand-induced conformational change in the receptors can be important for mediating protein—protein interaction with RAC3. Since the AF2-AD domain of the receptors may undergo a dramatic conformational change upon ligand-binding (Renaud et al., Nature 378:681–9, 1995), and since this domain is absolutely required for ligand-dependent transcriptional activation by nuclear receptors, three AF2-AD deletion mutants were tested for their abilities to interact with RAC3 in the presence or absence of hormones. The three deletion mutatants were the C-terminal AF2-AD domain of RAR truncated at residue 403 (403*), full-length hRXRα truncated at amino acid 443 (RXR443*), and LBD of hVDR truncated at amino acid 364 (VDR364*).

Figure 7:
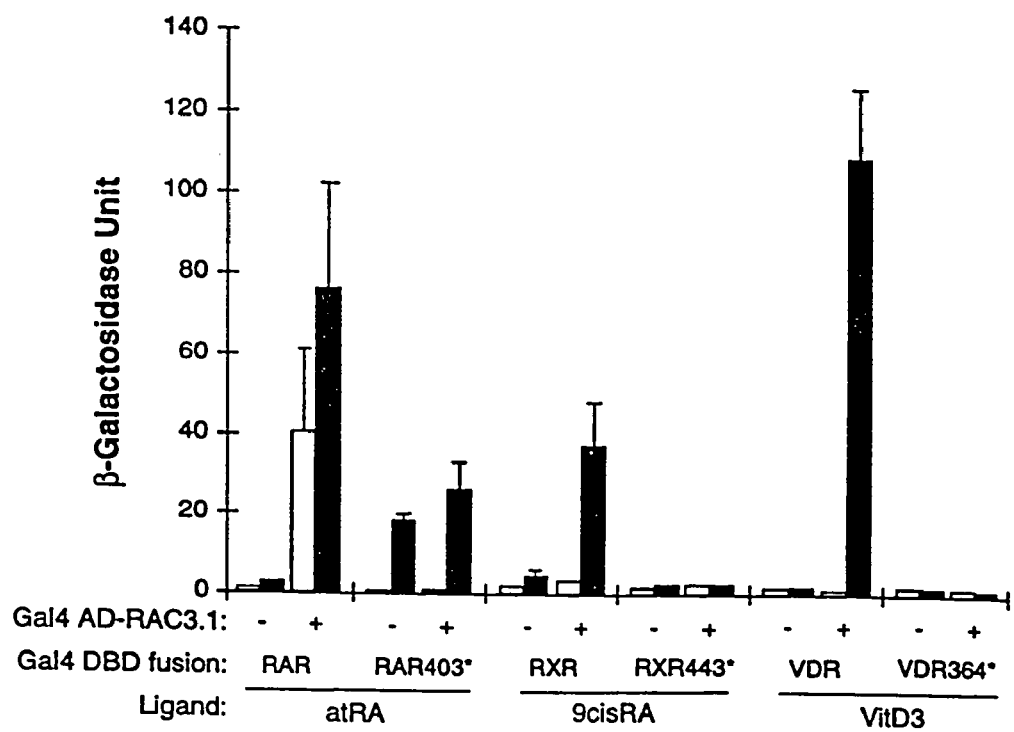
FIG. 7 is a representation of the β-galactosidase activity data from cotransfection experiments of Gal4 DBD fusions (RAC3.1) and Gal4 DBD fusions in the presence of appropriate ligands.

The Gal4 AD fusion (RAC3.1) and Gal4 DBD fusion were cotransformed into yeast Y190 cells, and the β-galactosidase activities from three independent colonies were determined (FIG. 7). The yeast cells were treated with 1 μM of indicated ligands (closed bars), or with an equal concentration of vehicle alone (open bars).

Truncation of the C-terminal AF2-AD domain of RAR at residue 403 created a dominant negative mutant RAR403*, which acted as a constitutive repressor in mammalian cells (Damm et al., Proc. Natl. Acad. Sci. USA 90:2989–93, 1993; Tsai and Collins, Proc. Natl. Acad. Sci. USA 90: 7153–7, 1993), but in yeast cells acted as a strong ligand-dependent transcriptional activator (FIG. 7). The mechanism underlying this difference between yeast and mammalian cells is unclear. However, a similar ligand-dependent transcriptional activation effect in yeast cells was observed with v-erbA (Privalsky et al., Cell 63:1277–86, 1990), a constitutive oncogenic repressor of TR in higher eukaryotic cells. Coexpression of RAR403* fusion with RAC3 did not further stimulate the reporter gene activity in either absence or presence of ligand, indicating that the interaction between intact RAR and RAC3 was abolished by deletion of the AF2-AD domain. A similar conclusion was obtained using mammalian culture cells, in which Gal4 DBD-RAR403* fusion did not activate transcription in response to ligand treatment. Truncation of the AF2-AD domains of RXR and VDR, unlike that of RAR, did not create ligand-dependent transcriptional activators in yeast cells, while the abilities to interact with RAC3 were totally eliminated (FIG. 7). These results demonstrate that the AF2-AD domains of RAR, RXR, and VDR are all absolutely required for interactions with RAC3; thus, RAC3 is an AF-2 dependent cofactor for nuclear receptors.

Example 7

RAC3 Contains a Transcriptionally Active Domain

The above results suggested that RAC3 is one of the components of a transcriptionally active complex of liganded receptors. Whether RAC3 can directly stimulate transcription when recruited to a specific promoter was tested by linking it with a heterologous DBD.

Monkey kidney-derived CV-1 cells and human lung carcinoma A549 cells were grown in phenol-free DMEM medium supplemented with 10% charcoal-stripped fetal bovine serum (Gibco). One day before transfection, cells were seeded in 12-well plates at a density of 50,000 cells per well. A mixture of DNAs was prepared that contained 0.5 μg of expression vector, 0.5 μg of pCMX-βGal used as internal control for transfection efficiency, 1 μg of luciferase reporter, and 1.5 μg of carrier DNA (PGEM) in a final volume of 30 μl. The DNA solution was mixed dropwise with one volume of 0.5 M $CaCl_2$ and two volumes of 2×BBS (50 mM N,N-bis(2-hydroxyethyl)-2-aminoethanesulfonic acid (BES; Calbiochem), 280 mM NaCl, 1.5 mM $Na_2HPO_4$, pH 6.95). DNA precipitates were allowed to form at room temperature for 10 minutes and applied evenly to the cell cultures. Cells were allowed to transfect for 12 hours, then the precipitates were removed by washing transfected cells twice with phosphate buffered saline (PBS). Transfected cells were refed fresh media containing either vehicle alone or vehicle plus ligands, and were harvested 24 hours after treatment.

Luciferase and β-galactosidase assays were used to analyze the cultures. Transfected cells in each well of the 12-well plate were lysed in 120 μl of cell lysis solution, then processed for luciferase and β-galactosidase assays. Fifty μl of lysed cells were transferred into 96-well microlite plates for luciferase assay and 96-well microtiter plates for β-galactosidase assay as described. The luciferase activities were determined with MLX microtiter plate luminometer (Dynex) using 100 μl of assay solution (0.1 M $KPO_4$, 5 mM ATP, 10 mM $MgCl_2$) and 100 μl of luciferin solution (0.01 M D-luciferin in 0.1 M $KPO_4$, pH 7.8). The luciferase activities were normalized to the β-galactosidase activity expressed from the cotransfected pCMX-βGal plasmid.

Figure 8:
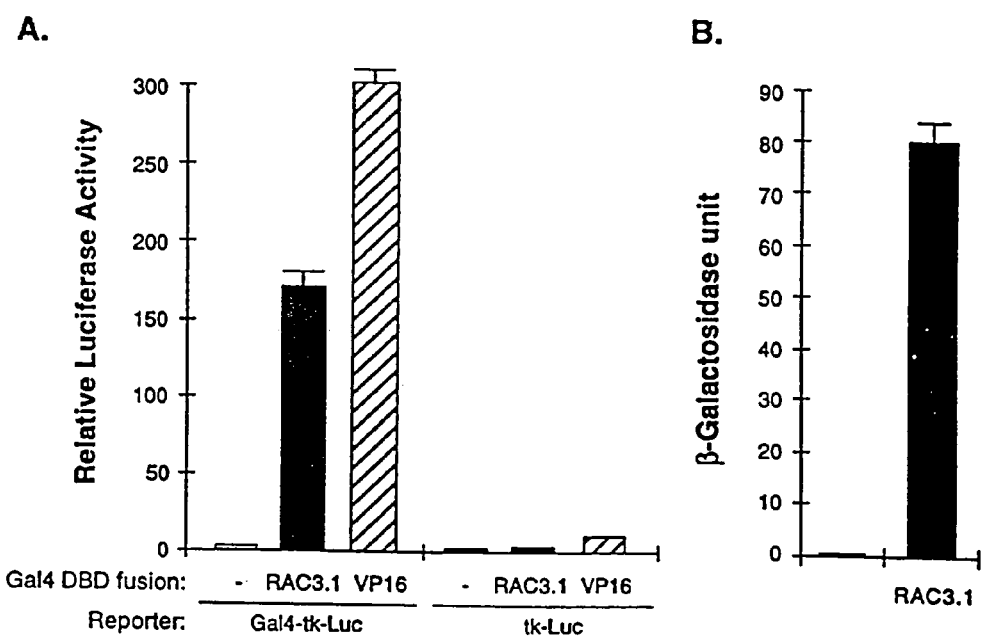
FIG. 8A is a representation of luciferase reporter data from cotransfection experiments in mammalian cells.
FIG. 8B is a representation of β-galactosidase reporter data from cotransfection experiments in yeast cells.

Transient transfection of a Gal4 DBD-RAC3 fusion into mammalian (CV-1) cells revealed strong stimulation of gene expression from a luciferase reporter containing five copies of Gal4-binding sites, but not from a parental reporter without the Gal4-binding sites (FIG. 8A of paper). The Gal4 DBD alone did not activate the reporter, while a Gal4 DBD fusion of VP16 activation domain strongly stimulated reporter gene expression. Similar experiments in yeast cells also demonstrated a RAC3-dependent transcription stimulation from a lacZ reporter in this organism (FIG. 8B). Thus, RAC3 itself contains a transcriptional activation domain that is functional in both mammalian and yeast cells.

Example 8

RAC3 Enhances Transcriptional Activation by Steroid/Nuclear Receptors

The ability of RAC3 to interact with liganded receptors in an AF2-dependent manner, to directly stimulate transcription when linked to a heterologous DBD, and its sequence similarity to two potent receptor coactivators strongly suggests that RAC3 functions as a steroid/nuclear receptor coactivator. To test the effect of overexpression of RAC3 on transcriptional activation by steroid/nuclear receptors a mammalian expression vector for full length RAC3 which was transiently transfected into human lung carcinoma A549 and/or CV-1 cells.

Figure 9:
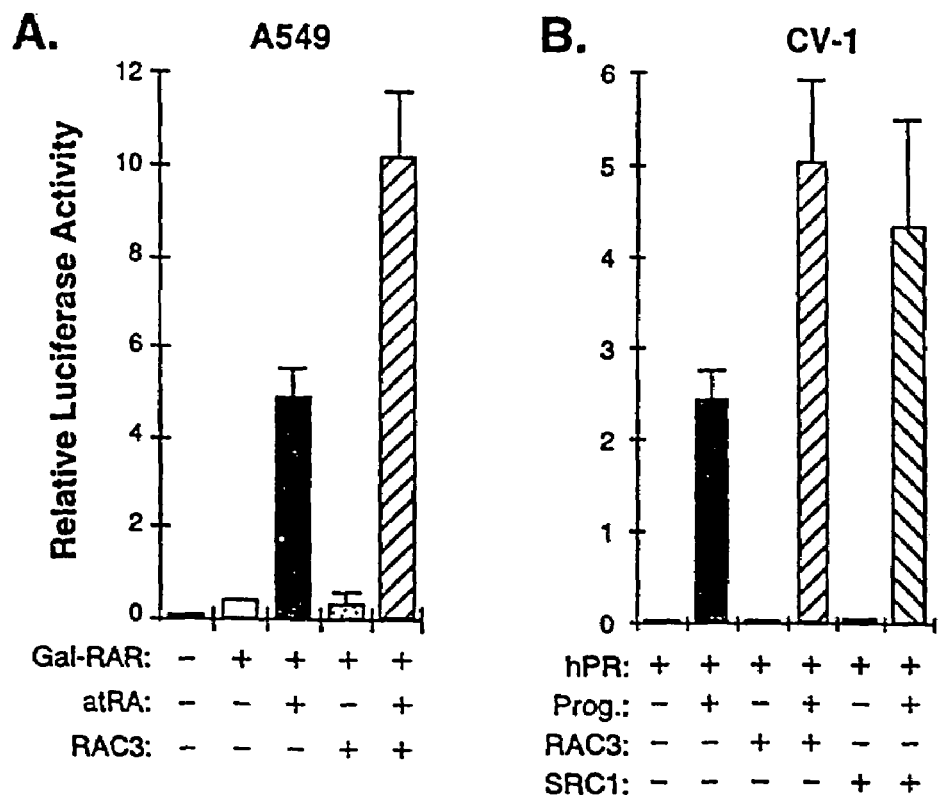
FIGS. 9A and 9B are representations of the data from cotransfection experiments with a Gal 4 DBD fusion of an LBD with and without RAC3 and ligand.

The pCMX-F.RAC3 construct that expresses full-length RAC3 was transfected into A549 cells together with a construct expressing Gal4 DBD fusion of the LBD of hRARα (Gal-RAR) and a Gal4-tk-Luc reporter. The relative luciferase activities (shown in FIG. 9) are averages from three independent experiments after normalization to β-galactosidase activity which was used as an internal control for transfection efficiency. Transfected cells were treated with vehicle alone (-) or with 100 nM of atRA for 24 hours after transfection. Overexpression of RAC3 does not have an effect on the luciferase reporter lacking Gal4-binding sites (not shown). Overexpression of RAC3 enhanced ligand-dependent transcriptional activation by Gal4 DBD fusion of RAR on a Gal4-dependent luciferase reporter about two-fold in A549 cells (FIG. 9). Similar effects were observed in CV-1 cells, but not in HeLa cells (data not shown).

In a similar experiment, RAC3 enhanced transcriptional activation by PR on the MMTV-LTR promoter. In this experiment, transfected cells were treated with or without 100 nM of progesterone at presence or absence of coexpressed RAC3 or SRC-1 in CV-1 cells.

The effect of overexpression of RAC3 on the transcriptional activation of a MMTV-LTR luciferase reporter by the human progesterone receptor (hPR) indicated that RAC3 also enhanced transcriptional activation by wild type hPR on a natural promoter, similar to the effect observed by full length human SRC-1 under the tested conditions. Thus, RAC3 is a bona fide transcriptional coactivator for mammalian steroid/nuclear hormone receptors.

Example 9

Identification of the Fragments of Rac3 which Mediate Interactions

Nuclear receptor coactivators and corepressors are involved in transcriptional regulation by steroid and non-steroid hormone receptors. The nuclear receptor-associated coactivator 3 (RAC3) was recently cloned and found highly related to the steroid receptor coactivator-1 (SRC 1) and the transcriptional intermediate factor 2 (TIF2). These three genes establish a novel family of nuclear receptor cofactors which are directly involved in ligand-dependent transcriptional activation of the receptors. In this study, the receptor interaction and transcriptional activation functions of RAC3 are characterized. A 140-amino acid fragment of RAC3 was found sufficient to mediate interactions with several liganded receptors in vivo and in vitro. Point mutations that disrupt AF2-AD function of RXR inhibited the interaction with RAC3. A 162-amino acid fragment of RAC3 is sufficient to confer transcriptional activation as well as recruitment of the CREB/E1A binding protein (CBP). The nuclear receptor interacting domain of RAC3 contains the N terminal three of the six motifs highly conserved among the central domains of RAC3, TIF2 and SRC 1, while the transcriptional activation domain of RAC3 contains the C terminal conserved motifs. Interestingly, the three C terminal motifs, but not the N terminal ones, are sufficient to activate transcription individually. These results suggest that these six conserved motifs might contribute to the two key but distinct functions of RAC3. In addition, RAC3, TIF2 and SRC-1 are highly expressed in certain tissues and cancer cells, and that the expression of RAC3 is directly upregulated by retinoid treatment. These results demonstrate that RAC3 may contribute to amplified transcriptional responses through both recruitment of additional coactivators and autoregulation by the receptor-coactivator complex.

Introduction

Transcriptional regulation by nuclear receptors for steroids, thyroid hormones (TR), retinoids (RAR) and vitamin D3 (VDR) controls key aspects of animal development, reproduction, homeostasis and adult organ physiology (for reviews see Mangelsdorf, D. J., et al. (1995) *Cell* 83, 835–839; Mangelsdorf, D. J. & Evans, R. M. (1995) *Cell* 83, 841–850; Kastner, P., et al. (1995) *Cell* 83, 859–869; Beato, M., et al. (1995) *Cell* 83, 851–857; Thurnmel, C. S. (1995) *Cell* 83, 871–877). The nuclear receptors are characterized by a common domain structure, including an N terminal A/B region which contains the first activation function (AF-1), a DNA-binding domain (DBD) responsible for recognition of specific DNA response elements, and a C terminal ligand binding domain (LBD) which also mediates dimerization with auxiliary nuclear receptor and transcriptional activation and repression. The TR and RAR form heterodimeric complexes with retinoid-X receptor (RXR) (for review, see (Mangelsdorf, D. J. & Evans, R. M. (1995) *Cell* 83, 841–850.) and such complexes are capable of repressing transcription in the absence of ligand and activating transcription upon ligand treatment (Baniahmad, A., et al. (1992) *Cell* 11, 1015–23.). The mechanisms of such dual repression and activation functions are not fully understood. Recently, nonreceptor proteins that can interact with nuclear receptors continue to be elucidated, and many of which are thought to play important roles in regulating transcriptional repression and activation functions of nuclear receptors (for review see Horwitz, K B., et al. (1996) *Mol. Endocrinology* 10, 1167–1177; Glass, C. K., et al. (1997) *Curr Opin Cell Biol* 9, 222–32. Chen, J. D. & Li, H. L. (1997) *Critical Reviews in Gene Expression* in press).

The involvement of non-receptor cofactors in nuclear receptor signaling was first postulated when members of the nuclear receptor superfamily were found to cross-react with each other functionally (Meyer, M., et al. (1989) *Cell* 57, 433–442.) and with other transcription factors (Schule, R., et al. (1990) *Cell* 61, 497–504.), and currently several such cofactors have been identified biochemically Halachmi, S., et al. (1994) *Science* 264, 1455–8. Cavailles, V., et al. (1994) *Proc Natl Acad Sci USA* 91, 10009–13; Kurokawa, R., et al. (1995) *Nature* 377, 451–4; Eggert, M., et al. (1995) *J. Biol. Chem.* 270, 30755–30759. Fondell, J. D., et al. (1996) *Proceedings of the National Academy of Sciences* 93, 8329–8333) as well as genetically (Seol, W., et al. (1995) *Mol Endocrinol* 9, 72–85; Chen, J. D. & Evans, R. M. (1995) *Nature* 377, 454–7). In particular, two related proteins known as the silencing mediator for RAR and TR (SMRT) and the nuclear receptor corepressor (N-CoR) were identified as both TR and RAR-interacting proteins which can assist trancsriptional repression by the unliganded receptors (Seol, W., et al. (1995) *Mol Endocrinol* 9, 72–85; Chen, J. D. et al. (1995) *Nature* 377, 454–7; Horlein, et al. (1995) *Nature* 377, 397–404; Sande, S. & Privalsky, M. L. (1996) *Molecular Endocrinology* 10, 813–825; Zarnir, I., et al. (1996) *Mol Cell Biol* 16, 5458–65.). Recently, SMRT and N-CoR were found to form complexes with the transcriptional corepressor mSin3 and the histone deacetylases HDAC1 or mRPD3 (Heinzel, T., et al. (1997) *Nature* 387, 43–8; Nagy, L., et al. (1997) *Cell* 89, 373–80; Li, H., et al. (1997) *Molecular Endocrinology* In-press.), suggesting that transcriptional repression by SMRT and N-CoR might involve histone deacetylation (Wolffe, A. P. (1997) *Nature* 387, 16–17; Pazin, M. J. & Kadonaga, J. T. (1997) *Cell* 89, 325–328.

Hormone binding is thought to dissociate the corepressor complex from nuclear receptors, allowing the receptors to recruit coactivators, such as the CREB/E1A-binding proteins (CBP/p300) (for review see (Janknecht, R. & Hunter, T. (1996) *Nature* 383, 22–3.) and references therein), the p300/CBP-associated factor (P/CAF) (28), and the steroid/ nuclear receptor coactivator (SRC) family proteins (for review see (Chen, J. D. & Li, H. L. (1997) *Critical Reviews in Gene Expression* in press,). In contrast to the nuclear receptor corepressor complexes, all these putative nuclear receptor coactivators contain intrinsic histone acetyltransferase activity (HAT) (Bannister, A. J. & Kouzarides, T. (1996) *Nature* 384, 641–3; Ogryzko, V. V., et al. (1996) *Cell* 87, 953–9; Spencer, T. E., et al. (1997) *Nature* 389, 194–98), suggesting that transcriptional activation or repression by nuclear receptors might be determined by the relative level of acetylation of the perhaps common targets of nuclear receptor coactivators and corepressors. Recent finding also suggest that, in addition to histones, CBP/p300 may also acetylate the activator proteins to modulate DNA binding ability (Gu, W. & Roeder, R. G. (1997) *Cell* 90, 595–606), suggesting the involvement of multiple targets and pathways in transcriptional regulation.

The steroid/nuclear receptor coactivator gene family contains the steroid receptor coactivator-1 (SRC-1; also known as NCoA-1) (Onate, S. A., et al. (1995) *Science* 270, 1354–1357; Takeshita, A., et al. (1996) *Endocrinology* 137, 3594–7; Kamei, Y., et al. (1996) *Cell* 85, 403–14; Yao, T. P., et al. (1996) *Proc Natl Acad Sci USA* 93, 10626–31; Zhu, Y., et al. (1996) *Gene Expr* 6, 185–95.), the transcriptional intermediate factor 2 (TIF2; also known as GRIP1) (Voegel, J. J., et al. (1996) *EMBO J.* 15, 3667–3675; Hong, H., et al. (1996) *Proc Natl Acad Sci USA* 93, 4948–52; Hong, H., et al. (1997) *Mol. Cell. Biol.* 17, 2735–2744), and the receptor-associated coactivator 3 (RAC3) (41, 42, 43). Sequence comparison of these proteins reveals that they share an overall identity of about 40% but with striking similarity at the N terminal basic-helix-loop-helix (bHLH) and Period-Aryl hydrocarbon receptor-Single minded (PAS) "A" and "B" domains. The bHLH-PAS domain function in protein—protein interactions, heterodimerization and target gene selection in many members of this family (Swanson, H. I., et al. (1995) *J Biol Chem* 270, 26292–302; Lindebro, M. C., et al. (1995) *EMBO J.* 14, 3528–39; Zelzer, E., et al. (1997) *Genes & Development* 11, 2065–2079), but the role of this domain in the SRC remains unclear. In addition to the bHLH-PAS domain, seven highly conserved regions containing a ØXXØ (Ø indicates hydrophobic residue) core consensus sequence flanked by highly charged and conserved residues are found in a central domain that mediates both nuclear receptor interaction and transcriptional activation functions of all three SRC proteins (Li, H., Gomes, P. J. & Chen, J. D. (1997) *Proc. Natl. Acad. Sci. USA* 94, 8479–8484; Torchia, J., et al. (1997) *Nature* (article) 387, 677–684; Heery, D. M., et al. (1997) *Nature* 387, 733–736.). These motifs are known as the LXXLL motifs or the leucine charged domains (LCD). Three of these motifs in SRC-1 have been shown to mediate direct protein—protein interaction with liganded receptors (Torchia, J., et al. (1997) *Nature* (article) 387, 677–684; Torchia, J., et al. (1997) *Nature* (article) 387, 677–684), suggesting that these conserved motifs might play an important role in the functions of these coactivators.

In this study, the nuclear receptor interaction and transcriptional activation domains of RAC3 have been further characterized and different LCD motifs are differentially have been found to be involved in either nuclear receptor interaction or transcriptional activation, suggesting the importance of the flanking sequences in determining the function of these LCD motifs. RAC3 interacts directly with CBP through its activation domain and that RAC3 can form a bridge for the interaction between CBP and nuclear receptors, suggesting that one mechanism of transcriptional activation by these coactivators is the recruitment of additional coactivators. In addition, the RAC3 transcript is directly upregulated by retinoic acid, demonstrating a new and perhaps independent mechanism of transcriptional coactivation by the nuclear receptor coactivators. Therefore, RAC3 plays an important role in nuclear receptor activation through utilization of multiple mechanisms.

Materials and Methods

Plasmids

The individual RAC3 fragments were obtained by either restriction enzyme digestion of the full-length RAC3 clone or by PCR amplification with synthetic primers harboring suitable cloning sites. The LXXLL motif constructs were generated by subcloning annealed double-stranded oligonucleotides encoding the specified amino acids into the yeast expression vector pAS1 (Durfee, T., et al.(1993) *Genes Dev* 7, 555–69.) The other constructs have been previously published (Chen, J. D. & Evans, R. M. (1995) *Nature* 377, 454–7; Yang, X. J., et al. (1996) *Nature* 382, 319–24. Voegel, J. J., et al. (1996) *EMBO J.* 15, 3667–3675; Li, H., et al. (1997) *Proc. Natl. Acad. Sci. USA* 94, 8479–8484; Umesono, et al. (1991) *Cell* 65, 1255–1266. Schulman, I. G., et al. (1995) *Proc Natl Acad Sci USA* 92, 8288–92.)

Far-Western Analysis

GST fusion proteins were overexpressed and purified from DH5α cells on glutathione agarose beads. The fusion proteins were separated on denaturing protein gels (SDS-PAGE) and electroblotted onto nitrocellulose filters in a transfer buffer (25 mM Tris-HCl, pH 8.3; 192 mM glycine; 0.01% SDS). After denaturation in 6 M guanidine hydrochloride (GnHCl), the proteins were renatured by stepwise dilution of GnHCl to 0.187 M in HB buffer (25 mM Hepes, pH 7.7; 25 mM NaCl; 5 mM MgC12; 1 mM DTT). The filters were then saturated with blocking buffer (5% non-fat milk, then 1% milk in HB buffer plus 0.05% NP40) at 4° C. overnight. In vitro translated 35S-labeled proteins were generated in reticulocyte lysate (Promega) and were diluted into a hybridization buffer (20 mM Hepes, pH 7.7; 75 mM KCl; 0.1 mM EDTA; 2.5 mM MgC12; 0.05% NP40; 1% milk; 1 mM DTT). The filters were allowed to hybridize overnight at 4° C. followed by three washes with hybridization buffer. The bound 35S-labeled proteins were detected by autoradiography.

Yeast Two-Hybrid Assay

The yeast two-hybrid assay was carried out in the yeast Y190 strain (Durfee, T., et al. (1993) *Genes Dev* 7, 555–69.) The GAL4 DBD fusion constructs were generated in the pGBT9 vector, and the GAL4 AD fusion constructs were made in the pGAD424 or pACTII vector (CLONTECH). The β-galactosidase activities were determined with the ONPG liquid assay as previously described (Chen, J. D., et al. (1996) *Proc Natl Acad Sci USA* 93, 7567–71.).

Cell Culture and Transient Transfection

African green monkey kidney CV-1 cells were grown in Dulbecco's Modified Eagle's medium (DMEM) supplemented with 10% resin-charcoal stripped fetal bovine serum, 50 U/ml penicillin G and 50 µg/ml streptomycin sulfate at 37° C. in 5% CO2. One day prior to transfection, cells were plated in 24-well culture dishes at a density of 50,000 cells per well. Transfection was performed by standard calcium phosphate precipitation. All transfection experiments were performed in triplicate, and were replicated at least once. Twelve hours after transfection, cells were washed with PBS and refed fresh medium containing the indicated amounts of ligand. After 30 hours, cells were harvested and β-galactosidase and luciferase activities were assayed as described previously (Chen, J. D., Umesono, K. & Evans, R. M. (1996) *Proc Natl Acad Sci USA* 93, 7567–71.) The relative luciferase activities are normalized to the β-galactosidase activities.

Luciferase and β-Galactosidase Assay

Transfected cells in each well were lysed as described (Chen, J. D., et al. (1996) *Proc Natl Acad Sci USA* 93, 7567–71.), and processed for the luciferase and the α-galactosidase assays. The lysates were transferred into 96-well microlite plates for luciferase assay and 96-well microtiter plates for β-galactosidase assay as described (Chen, J. D., Umesono, K. & Evans, R. M. (1996) *Proc Natl Acad Sci USA* 93, 7567–71.). The luciferase activities were determined with a MLX microtiter plate luminometer (Dynex) using 100 μl of assay solution (0.1 M KPO4, 5 mM ATP, 10 mM MgC12) and 100 μl of luciferin solution (0.01 M D-luciferin in 0.1 M KPO4, pH 7.8). The luciferase activities were normalized to the β-galactosidase activity expressed from the cotransfected pCMX-βGal plasmid.

Northern Blot Analysis

Cells were treated with different concentration of RA (0, 10, 100, 1000 nM) for a period of 12 hours. In the control group, cells were treated with equal volume of solvent (80% EtOH plus 20% DMSO). Total RNAs were isolated using an RNA isolation kit (RNAzol) and separated on a 1% agarose gel with 2.2 M formaldehyde and blotted onto nylon filters. Filters were hybridized with random-primed $^{32}$P-labeled DNA probes specific for RAC3, Tw2, and SRC1 in hybridization buffer (50% formamide, 5X SSPE [1×SSPE is 0.18 M NaCl, 10 mM NaPO4, and 1 mM EDTA at pH 7.7], 2× Denhardt solution, 0.1% SDS, 0.1 mg of sheared herring sperm DNA per ml) at 42° C. overnight. The final wash was in 1×SSC (0.15 M NaCl plus 0.015 M sodium citrate)-0.1% SDS at 65° C. Filters were exposed to X-ray film at −70° C. for about 24 hours.

Results

RAC3-Nuclear Receptor Interaction

The nuclear receptor interaction and transcriptional activation functions of RAC3 have been previously located within a central fragment between amino acids 401 and 1204 (Li, H., et al. (1997) *Proc. Natl. Acad. Sci. USA* 94, 8479–8484.). In these experiments, RAC3 fragments were expressed as GAL4 AD fusions in the yeast pGAD424 vector. Individual pGAD-RAC3 constructs were cotransformed with a pGBT-F.RAR construct which expresses a GAL4 DBD-full-length hRARα fusion. Relative β-galactosidase activities were determined from three independent transformants in the absence or presence of 1 IμM atRA. RAC3 fragments were expressed as GAL4 DBD fusions in the pCMX-Gal vector (Chen, J. D., et al. (1996) *Proc Natl Acad Sci USA* 93, 7567–71.) and cotransfected together with a VP16-RAR fusion contruct which expresses a VP16 AD-full-length hRARα fusion. Relative luciferase activities were determined from three independent transfections in the absence or presence of 1 μM atRA. Interaction of RAC3 with nuclear receptors was tested in vitro. The purified GST module (GST) and GST-RAC3-RID (RID) fusion were separated by SDS-PAGE and analyzed by far-Western analyses for interaction with 35S-labeled hRARα, hTRp and hERa in the absence or presence of 1 μM cognate ligands. The positions of the intact GST-RAC3-RID fusion proteins are marked with asterisks. T3, 3,5,3'-triiodo-L-thyronine; E2, 17β-estradiol; RA, all-trans retinoic acid. Receptor AF2-AD point mutations disrupt RAC3 interaction. The interactions between RAC3 and AF2-AD point mutants were determined in the yeast two-hybrid system. The RAC3.1 fragment was expressed as a GAL4 AD fusion while RXR mutants were expressed as GAL4 DBD fusions and the β-galactosidase activities were determined from three transformants in the absence or presence of 1 μM 9-cis RA. Deletion of amino acids 507 to 1017 eliminates the receptor interaction and that the rest of the N terminal and C terminal sequences can not interact with liganded RAR and other class II receptors, suggesting that amino acids 507–1017 contains the interacting domain. The interaction was then confirmed in mammalian cells, where amino acids 401–800 and 613–752 fragments both interact with RAR in a ligand-enhanced manner, while the 401–695 and 401–624 fragments do not interact with the receptor significantly, suggesting that the 140-amino acids fragment (between 613 and 752) is the nuclear receptor interacting domain (RID). Consistently with previous studies (Torchia, J., et al. (1997) *Nature* 387, 677–684., 47; Torchia, J., et al. (1997) *Nature* (article) 387, 677–684.), this RID domain of RAC3 contains three LCD motifs which have been implicated in mediating direct interaction between SRC-1 and nuclear receptors (Torchia, J., et al. (1997) *Nature* 387, 677–684., 47; Torchia, J., et al. (1997) *Nature* (article) 387, 677–684.). To further confirm the interactions between RAC3-RID and nuclear receptors, a GST-RID fusion and analyzed its interaction with three nuclear receptors in vitro by far-Western blot analyses. Significant interactions were observed with liganded RAR, TR and ER, demonstrating that this RID domain indeed mediates ligand-dependent interactions between RAC3 and nuclear receptors.

Point Mutations of the AF2-AD that Abolish RAC3 Interaction

The interaction between RAC3 and nuclear receptor has been shown to depend on the presence of an intact AF2-AD domain (Li, H., et al. (1997) *Proc. Natl. Acad. Sci. USA* 94, 8479–8484.). Here, whether the AF-2 function per se is required for such interaction was tested. Several point mutations within the AF2-AD helix of the RXR (Schulman, I. G., et al. (1995) *Proc Natl Acad Sci USA* 92, 8288–92.) were analyzed for their effects on RAC3 interaction. Disruption of the AF-2 function by three independent AF2-AD point mutations (F450A, F450P and ML454A) abolishes the interaction between RAC3 and RXR. In contrast, a neutral AF2-AD mutation (M452A) permits a strong ligand dependent interaction. These results suggest that the activation function of the AF2-AD helix correlates with its ability to interact with RAC3, further supporting the hypothesis that RAC3 is an AF-2 dependent nuclear receptor coactivator.

Three Conserved LCD Motifs Activate Transcription

The transcriptional activation domain of RAC3 was previously located within amino acids 401–1204 (Li, H., et al. (1997) *Proc. Natl. Acad. Sci. USA* 94, 8479–8484.). Transcriptional activation by RAC3 was assayed in mammalian cells. RAC3 fragments were expressed as GAL4 DBD fusions in the pCMX-Gal vector. The relative fold induction was determined by comparing with the pCMX-Gal vector. RAC3 fragments or individual motifs were expressed as GAL4 DBD fusions in the Y190 cells, and the β-galactosidase units were determined from three independent transformants. Deletional analyses reveal that the AD of RAC3 is located at the C terminal region of this central fragment, in contrast to the receptor interacting domain found at the N terminal. In particular, amino acids 401 to 800 and its further deletion mutants can not activate reporter gene expression, while the C terminal fragments 982–1204, 982–1056 and 1017–1179 strongly stimulate reporter gene expression. Like the N terminal receptor interacting domain, these C terminal transactivation domains also contain several highly conserved LCD motifs. Since these motifs are not required for nuclear receptor interaction, they might be involved in transcriptional activation. The transcriptional activation function of each of these motifs was analyed. The three C terminal motifs (iv, v and vi) can activate transcription significantly, but not any of the N terminal motifs. These results indicate that the C terminal motifs are directly involved in transcriptional activation function of RAC3.

RAC3 Interacts with CBP and Nuclear Receptor Simultaneously

Since SRC-1 can interact with the general transcriptional coactivator CBP and p300 (Yao, T. P., et al. (1996) *Proc Natl Acad Sci USA* 93, 10626–31.), it was determined whether RAC3 can also interact with CBP by far-Western analyses. Serial GST-CBP fusions covering the SRC-1 interacting domain were analyzed for interactions with $^{35}$S-labeled full-length RAC3, SRC-1 and RAC3-AD (FIGS. 3A, B and C). RAC3 interacts strongly with the CBP fragments C and D, but not with other fragments. Similarly, SRC-1 interacts with CBP fragments C and D, consistent with previous observations (Kamei, Y., et al. (1996) *Cell* 85, 403–14; Yao, T. P., et al. (1996) *Proc Natl Acad Sci USA* 93, 10626–31.). RAC3-AD alone is sufficient for CBP interaction, suggesting that one function of the RAC3-AD might be the recruitment of CBP or the related protein p300.

The ability of RAC3 to interact with both CBP and nuclear receptors prompted us to test whether each pair of interactions are stable enough to mediate the formation of a ternary complex. A trimeric far-Western protocol was developed to test this possibility. Briefly, the CBP fragments C and D were probed first with unlabeled full-length RAC3 and then with $^{35}$S-labeled nuclear receptor. The results demonstrate that RAC3 can bridge the interaction between CBP and RAR in the presence of ligand, but not in the absence of ligand. As controls, the CBP fragments C and D were probed parallely with $^{35}$S-RAC3 and $^{35}$S-RAR individually. These results suggest that the strength of interactions between CBP-RAC3 and RAC3-RAR are sufficient to link together a ternary complex. These results also confirm that RAC3 utilizes distinct domains for interaction with CBP and RAR.

RAC3 is Expressed in a Tissue- and Cancer Cell-Specific Manner

The expression patterns of RAC3 in different human tissues and cancer cells were examined and compared with that of SRC-1 and TIF2. Human multiple tissue (left) and cancer cell Northern blots were first hybridized with a $^{32}$P-RAC3 DNA probe, then rehybridized with $^{32}$P-SRC-1 and then with $^{32}$P-TIF2 probes. Between each rehybridization, the membranes were exposed to X-ray films to ensure appropriate stripping of the earlier probe. SRC-1 transcripts showed different patterns from that of RAC3 and TIF2, indicating the absence of cross-contamination from each hybridization. Total RNA (20 µg) of HL-60 cells treated with indicated concentrations of atRA for 12 hours or with 1 µM tRA plus 10 µM cycloheximide (CHX) were analyzed for RAC3 message by Northern blot analysis. Ethidium bromide staining of the gel confirmed that each lane contained an equal amount of RNA. RAC3 is expressed at high levels in the heart, placenta, skeletal muscle and pancreas, but at vey low levels in the brain, lung, liver and kidney. The SRC-1 message is expressed at high levels in the heart, brain, placenta, skeletal muscle and pancreas, and again at extreme low levels in the lung, liver and kidney. Two distinct SRC-1 messages are clearly detectable and the larger messages appear to be expressed at higher levels than the smaller form. The expression pattern of TIF2 is very similar to that of RAC3 with the highest expression in the heart instead of placenta. In the human cancer cells, highest expression of RAC3 message in the Burkitt's lymphoma Raji cells as well as in the epitheloid carcinoma HeLa cells, the chronic myelogenous leukemia K-562 cells, the colorectal adenocarcinoma SW480 cells, and the melanoma G361 cells. Extreme low levels of RAC3 are found in promyelocytic leukemia HL-60 cells, the lymphoblastic leukemia MOLT4 cells, and the lung carcinoma A549 cells. These results indicate that RAC3 expression variates greatly in different tissues and cancer cells. In contrast, the SRC-1 transcript is highly expressed only in chronic myelogenous leukemia K-562 cells and the colorectal adenocarcinoma SW480 cells, but not in the Burkitt's lymphoma Raji cells. The expression pattern of TIF2 is very similar to that of RAC3 with the highest expression level in the Raji cells. Together, these results suggest that the expression of the SRC family genes are highly variable in different tissues and cell types.

RAC3 Expression is Upregulated by Retinoic Acid

The expression of nuclear receptor genes are frequently regulated by cognate hormones and, in particular, autoregulation of the RAR gene expression by atRA has been thoroughly characterized (de The, H., et al. (1989) *EMBO J.* 8, 429–433.). Since RAC3 is involved in transcriptional activation of RAR, the coactivator gene expression might also be regulated by the receptor-coactivator complex, forming a complete autoregulatory pathway. atRA significantly enhances the expression of RAC3 in a concentration-dependent manner. After ligand binding, the RXR-RAR heterodimer recruits a coactivator complex that contains members of the SRC family proteins, CBP/p300 and P/CAF. This coactivator complex functions as an acetylator machinery that acetylate histones and disrupt nucleosome structure, allowing the access of basal transcriptional machinery to the core promoter. Since both RAR and RAC3 transcripts are elevated by RA treatment, the increased concentration of the two key proteins should further amplify the transcriptional responses, leading highly level of gene induction. The induction of RAC3 transcript is most obvious at a concentration between $10^{-8}$ and $10^{-7}$ M of atRA and that such atRA-induced RAC3 gene expression is not sensitive to inhibition of de novo protein synthesis. Similar upregulation of RAC3 expression is also found in the acute promyelocytic leukemic NB4 cells. Together, these results suggest that RAC3 not only functions as an RAR coactivator, its expression is also autoregulated by the receptor-coactivator complex activated by retinoid treatment.

Discussion

The nuclear receptor coactivator RAC3 utilizes a 14hRAR*amino acid domain to interact with liganded nuclear receptors, a C terminal 162-amino acid domain to activate transcription and interact with CBP, and that three C terminal LCD motifs are sufficient independently for transcriptional activation. RAC3, SRC-1 and TIF2 are all expressed in a tissue-specific manner and the expression of RAC3 can be directly upregulated by retinoic acid. These findings have further extented previous observations (Li, H., et al. (1997) *Proc. Natl. Acad. Sci. USA* 94, 8479–8484; Torchia, J., et al. (1997) *Nature* (article) 387, 677–684; Chen, H., et al. (1997) *Cell* 90, 569–580.), and suggest that different LCD motifs might contribute differently for receptor interaction and transcriptional activation, and that RAC3 may potentiate transcriptional activation of nuclear receptors through a combination of recruitment of additional coactivators and autoregulation of its own gene expression.

Our data suggests that the three N terminal LCD motifs are likely involved in nuclear receptor interaction, consistent with recent studies of the SRC-1 and p/C1P (Torchia, J., et al. (1997) Nature 387, 677–684; Torchia, J., et al. (1997) Nature 387, 677–684.) where the individual motifs were found to be sufficient to medate nuclear receptor interaction. In contrast, the three C terminal LCD motifs are sufficient individually to activate transcription. These results suggest the conserved ØXXØ consensus per se is not enough to determine the function of these motifs and that specific structural constraints of these motifs, perhaps defined by neighboring residues, are also important in determining the function of these motifs.

It was recently shown that ACTR and SRC-1 both possess intrinsic histone acetyltransferase (HAT) activity (Spencer, T. E., et al. (1997) Nature 389, 194–98; Chen, H., et al. (1997) Cell 90, 569–580.). Such HAT activity is also observed in RAC3, albeit very weakly compared with the p/CAF (our unpublished data). ACTR and SRC-1 preferentially acetylate histones H3 and H4, both in the free form and in the mononucleosome (Spencer, T. E., et al. (1997) Nature 389, 194–98.; Chen, H., et al. (1997) Cell 90, 569–580.). Comparison of the diacetyl H3 peptides suggests that Lys 9 and Lys 14 of histone H3 are the preferred sites for SRC-1 acetylation (Spencer, T. E., et al. (1997) Nature 389, 194–98.). Similarly, H3 is also a preferred substrate for ACTR (Chen, H., et al. (1997) Cell 90, 569–580.), but the acetylated lysine residues remain unknown. Since histone acetylation has been correlated with gene activation (Wolffe, A. P. & Pruss, D. (1996) Cell 86, 817–819; Brownell, J. E. & Allis, C. D. (1996) Curr Opin Genet Dev 6, 176–84.), these findings suggest that histone acetylation might be critical for gene activation by nuclear receptors. It remains unclear whether individual acetylases in the putative coactivator complex could modify histones in a redundant manner or whether different HAT enzymes are used for modification of distinct residues. In the latter case, such differential acetylation events might result in synergistic transcriptional activation. Alternatively, it was shown recently that the general coactivator CBP/p300 can also acetylate the sequence-specific tumor suppressor p53, and that such acetylation event promotes DNA binding by pS3 (Gu, W. & Roeder, R. G. (1997) Cell 90, 595–606.).

The expression patterns of RAC3, TIF2 and SRC-1 appear to be tissue and cancer cell-specific, suggesting that the normal function of these coactivators might be limited to certain tissues and cells. The expression patterns of SRC family genes are different from earlier studies using mouse tissues (Yao, T. P., et al. (1996) Proc Natl Acad Sci USA 93, 10626–31, Zhu, Y., et al. (1996) Gene Expr 6, 185–95; Hong, H., et al. (1997) Mol. Cell. Biol. 17, 2735–2744.42; Torchia, J., et al. (1997) Nature (article) 387, 677–684.). These differences might reflect a more selective expression of RAC3 in human than in mouse. The expression of RAC3 and SRC-1 is largely overlapped in normal tissues, while the expression in cancer cells shows high levels of variation. The lung carcinoma A549 cells appear to express none of the three coactivators, which is consistent with the lack of expression of these three genes in the normal lung tissue and correlate with resistant phenotype of lung carcinoma to retinoid treatment (Moghal, N. & Neel, B. G. (1995) Mol Cell Biol 15, 3945–59; Lee, H. Y., et al. (1997) Cell Growth Differ 8, 283–91.). Interestingly, RAC3 and TIF2, but not SRC-1, are highly overexpressed in the Burkitt's lymphoma Raji cells, and all three SRC genes are highly expressed in the colorectal carcinoma SW480 cells. One of these coactivators is amplified in these cells, anologous to the previous observation in the breast cancer cells (Anzick, S. L., et al. (1997) Science 277, 965–968).

Autoregulation has long been established as a mechanism that contributes significantly to the high level of gene induction by retinoids (de The, H., Marchio, A., Tiollais, P. & Dejean, A. (1989) EMBO J. 8, 429–433.). For instance, atRA treatment induces RARβ gene expression, and a RAR response element was subsequently identified in the promoter region of this gene (Sucov, H. M., Murakami, K. K. & Evans, R. M. (1990) Proc Natl Acad Sci USA 87, 5392–6.1.). Therefore, the binding of atRA to endogenous RAR is expected to activate expression of the receptor gene itself, thereby raising the level of the receptor and amplifying the effect of the ligand. This form of autoregulation is expected to play an important role in RA-dependent pattern formation and morphogenesis. It is now known that RAR is not the only factor responsible for such feedback control of gene activation. This study demonstrates that expression of the coactivator RAC3 is also increased by atRA treatment in at least two different RA responsive cancer cells, suggesting that a simultaneously enhancement of the receptor and the coactivator may force the formation an activator complex that stimulate gene expression upon ligand treatment. Transcriptional activation by nuclear receptors might be the result of a combined effect of coactivator recruitment and autoinduction of multiple effector gene expression.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 4496 base pairs

```
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 86..4338

(xi) SEQUENCE DESCRIPTION: SEQ ID NO:1:

GCTGGATGGT GGACTCAGAG ACCAATAAAA ATAAACTGCT TGAACATCCT TTGACTGGTT         60

AGCCAGTTGC TGATGTATAT TCAAG ATG AGT GGA TTA GGA GAA AAC TTG GAT          112
                            Met Ser Gly Leu Gly Glu Asn Leu Asp
                             1               5

CCA CTG GCC AGT GAT TCA CGA AAA CGC AAA TTG CCA TGT GAT ACT CCA          160
Pro Leu Ala Ser Asp Ser Arg Lys Arg Lys Leu Pro Cys Asp Thr Pro
 10              15                  20                  25

GGA CAA GGT CTT ACC TGC AGT GGT GAA AAA CGG AGA CGG GAG CAG GAA          208
Gly Gln Gly Leu Thr Cys Ser Gly Glu Lys Arg Arg Arg Glu Gln Glu
                 30                  35                  40

AGT AAA TAT ATT GAA GAA TTG GCT GAG CTG ATA TCT GCC AAT CTT AGT          256
Ser Lys Tyr Ile Glu Glu Leu Ala Glu Leu Ile Ser Ala Asn Leu Ser
             45                  50                  55

GAT ATT GAC AAT TTC AAT GTC AAA CCA GAT AAA TGT GCG ATT TTA AAG          304
Asp Ile Asp Asn Phe Asn Val Lys Pro Asp Lys Cys Ala Ile Leu Lys
         60                  65                  70

GAA ACA GTA AGA CAG ATA CGT CAA ATA AAA GAG CAA GGA AAA ACT ATT          352
Glu Thr Val Arg Gln Ile Arg Gln Ile Lys Glu Gln Gly Lys Thr Ile
     75                  80                  85

TCC AAT GAT GAT GAT GTT CAA AAA GCC GAT GTA TCT TCT ACA GGG CAG          400
Ser Asn Asp Asp Asp Val Gln Lys Ala Asp Val Ser Ser Thr Gly Gln
 90                  95                 100                 105

GGA GTT ATT GAT AAA GAC TCC TTA GGA CCG CTT TTA CTT CAG GCA TTG          448
Gly Val Ile Asp Lys Asp Ser Leu Gly Pro Leu Leu Leu Gln Ala Leu
                110                 115                 120

GAT GGT TTC CTA TTT GTG GTG AAT CGA GAG GCA AAC ATT GTA TTT GTA          496
Asp Gly Phe Leu Phe Val Val Asn Arg Glu Ala Asn Ile Val Phe Val
            125                 130                 135

TCA GAA AAT GTC ACA CAA TAC CTG CAA TAT AAG CAA GAG GAC CTG GTT          544
Ser Glu Asn Val Thr Gln Tyr Leu Gln Tyr Lys Gln Glu Asp Leu Val
        140                 145                 150

AAC ACA AGT GTT TAC AAT ATC TTA CAT GAA GAA GAC AGA AAG GAT TTT          592
Asn Thr Ser Val Tyr Asn Ile Leu His Glu Glu Asp Arg Lys Asp Phe
    155                 160                 165

CTT AAG AAT TTA CCA AAA TCT ACA GTT AAT GGA GTT TCC TGG ACA AAT          640
Leu Lys Asn Leu Pro Lys Ser Thr Val Asn Gly Val Ser Trp Thr Asn
170                 175                 180                 185

GAG CCC CAA AGA CAA AAA AGC CAT ACA TTT AAT TGC CGT ATG TTG ATG          688
Glu Pro Gln Arg Gln Lys Ser His Thr Phe Asn Cys Arg Met Leu Met
                190                 195                 200

AAA ACA CCA CAT GAT ATT CTG GAA GAC ATA AAC GCC AGT CCT GAA ATG          736
Lys Thr Pro His Asp Ile Leu Glu Asp Ile Asn Ala Ser Pro Glu Met
            205                 210                 215

CGC CAG AGA TAT GAA ACA ATG CAG TGC TTT GCC CTG TCT CAG CCA CGA          784
Arg Gln Arg Tyr Glu Thr Met Gln Cys Phe Ala Leu Ser Gln Pro Arg
        220                 225                 230

GCT ATG ATG GAG GAA GGG GAA GAT TTG CAA TCT TGT ATG ATC TGT GTG          832
Ala Met Met Glu Glu Gly Glu Asp Leu Gln Ser Cys Met Ile Cys Val
    235                 240                 245

GCA CGC CGC ATT ACT ACA GGA GAA AGA ACA TTT CCA TCA AAC CCT GAG          880
```

```
            Ala Arg Arg Ile Thr Thr Gly Glu Arg Thr Phe Pro Ser Asn Pro Glu
            250                 255                 260                 265

AGC TTT ATT ACC AGA CAT GAT CTT TCA GGA AAG GTT GTC AAT ATA GAT              928
Ser Phe Ile Thr Arg His Asp Leu Ser Gly Lys Val Val Asn Ile Asp
                270                 275                 280

ACA AAT TCA CTG AGA TCC TCC ATG AGG CCT GGC TTT GAA GAT ATA ATC              976
Thr Asn Ser Leu Arg Ser Ser Met Arg Pro Gly Phe Glu Asp Ile Ile
            285                 290                 295

CGA AGG TGT ATT CAG AGA TTT TTT AGT CTA AAT GAT GGG CAG TCA TGG             1024
Arg Arg Cys Ile Gln Arg Phe Phe Ser Leu Asn Asp Gly Gln Ser Trp
            300                 305                 310

TCC CAG AAA CGT CAC TAT CAA GAA GCT TAT CTT AAT GGC CAT GCA GAA             1072
Ser Gln Lys Arg His Tyr Gln Glu Ala Tyr Leu Asn Gly His Ala Glu
            315                 320                 325

ACC CCA GTA TAT CGA TTC TCG TTG GCT GAT GGA ACT ATA GTG ACT GCA             1120
Thr Pro Val Tyr Arg Phe Ser Leu Ala Asp Gly Thr Ile Val Thr Ala
330                 335                 340                 345

CAG ACA AAA AGC AAA CTC TTC CGA AAT CCT GTA ACA AAT GAT CGA CAT             1168
Gln Thr Lys Ser Lys Leu Phe Arg Asn Pro Val Thr Asn Asp Arg His
                350                 355                 360

GGC TTT GTC TCA ACC CAC TTC CTT CAG AGA GAA CAG AAT GGA TAT AGA             1216
Gly Phe Val Ser Thr His Phe Leu Gln Arg Glu Gln Asn Gly Tyr Arg
            365                 370                 375

CCA AAC CCA AAT CCT GTT GGA CAA GGG ATT AGA CCA CCT ATG GCT GGA             1264
Pro Asn Pro Asn Pro Val Gly Gln Gly Ile Arg Pro Pro Met Ala Gly
            380                 385                 390

TGC AAC AGT TCG GTA GGC GGC ATG AGT ATG TCG CCA AAC CAA GGC TTA             1312
Cys Asn Ser Ser Val Gly Gly Met Ser Met Ser Pro Asn Gln Gly Leu
395                 400                 405

CAG ATG CCG AGC AGC AGG GCC TAT GGC TTG GCA GAC CCT AGC ACC ACA             1360
Gln Met Pro Ser Ser Arg Ala Tyr Gly Leu Ala Asp Pro Ser Thr Thr
410                 415                 420                 425

GGG CAG ATG AGT GGA GCT AGG TAT GGG GGT TCC AGT AAC ATA GCT TCA             1408
Gly Gln Met Ser Gly Ala Arg Tyr Gly Gly Ser Ser Asn Ile Ala Ser
                430                 435                 440

TTG ACC CCT GGG CCA GGC ATG CAA TCA CCA TCT TCC TAC CAG AAC AAC             1456
Leu Thr Pro Gly Pro Gly Met Gln Ser Pro Ser Ser Tyr Gln Asn Asn
            445                 450                 455

AAC TAT GGG CTC AAC ATG AGT AGC CCC CCA CAT GGG AGT CCT GGT CTT             1504
Asn Tyr Gly Leu Asn Met Ser Ser Pro Pro His Gly Ser Pro Gly Leu
            460                 465                 470

GCC CCA AAC CAG CAG AAT ATC ATG ATT TCT CCT CGT AAT CGT GGG AGT             1552
Ala Pro Asn Gln Gln Asn Ile Met Ile Ser Pro Arg Asn Arg Gly Ser
            475                 480                 485

CCA AAG ATA GCC TCA CAT CAG TTT TCT CCT GTT GCA GGT GTG CAC TCT             1600
Pro Lys Ile Ala Ser His Gln Phe Ser Pro Val Ala Gly Val His Ser
490                 495                 500                 505

CCC ATG GCA TCT TCT GGC AAT ACT GGG AAC CAC AGC TTT TCC AGC AGC             1648
Pro Met Ala Ser Ser Gly Asn Thr Gly Asn His Ser Phe Ser Ser Ser
                510                 515                 520

TCT CTC AGT GCC CTG CAA GCC ATC AGT GAA GGT GTG GGG ACT TCC CTT             1696
Ser Leu Ser Ala Leu Gln Ala Ile Ser Glu Gly Val Gly Thr Ser Leu
            525                 530                 535

TTA TCT ACT CTG TCA TCA CCA GGC CCC AAA TTG GAT AAC TCT CCC AAT             1744
Leu Ser Thr Leu Ser Ser Pro Gly Pro Lys Leu Asp Asn Ser Pro Asn
            540                 545                 550

ATG AAT ATT ACC CAA CCA AGT AAA GTA AGC AAT CAG GAT TCC AAG AGT             1792
Met Asn Ile Thr Gln Pro Ser Lys Val Ser Asn Gln Asp Ser Lys Ser
555                 560                 565
```

```
CCT CTG GGC TTT TAT TGC GAC CAA AAT CCA GTG GAG AGT TCA ATG TGT        1840
Pro Leu Gly Phe Tyr Cys Asp Gln Asn Pro Val Glu Ser Ser Met Cys
570             575                 580                 585

CAG TCA AAT AGC AGA GAT CAC CTC AGT GAC AAA GAA AGT AAG GAG AGC        1888
Gln Ser Asn Ser Arg Asp His Leu Ser Asp Lys Glu Ser Lys Glu Ser
                590                 595                 600

AGT GTT GAG GGG GCA GAG AAT CAA AGG GGT CCT TTG GAA AGC AAA GGT        1936
Ser Val Glu Gly Ala Glu Asn Gln Arg Gly Pro Leu Glu Ser Lys Gly
                    605                 610                 615

CAT AAA AAA TTA CTG CAG TTA CTT ACC TGT TCT TCT GAT GAC CGG GGT        1984
His Lys Lys Leu Leu Gln Leu Leu Thr Cys Ser Ser Asp Asp Arg Gly
                620                 625                 630

CAT TCC TCC TTG ACC AAC TCC CCC CTA GAT TCA AGT TGT AAA GAA TCT        2032
His Ser Ser Leu Thr Asn Ser Pro Leu Asp Ser Ser Cys Lys Glu Ser
635                 640                 645

TCT GTT AGT GTC ACC AGC CCC TCT GGA GTC TCC TCC TCT ACA TCT GGA        2080
Ser Val Ser Val Thr Ser Pro Ser Gly Val Ser Ser Ser Thr Ser Gly
650                 655                 660                 665

GGA GTA TCC TCT ACA TCC AAT ATG CAT GGG TCA CTG TTA CAA GAG AAG        2128
Gly Val Ser Ser Thr Ser Asn Met His Gly Ser Leu Leu Gln Glu Lys
                    670                 675                 680

CAC CGG ATT TTG CAC AAG TTG CTG CAG AAT GGG AAT TCA CCA GCT GAG        2176
His Arg Ile Leu His Lys Leu Leu Gln Asn Gly Asn Ser Pro Ala Glu
                685                 690                 695

GTA GCC AAG ATT ACT GCA CAA GCC ACT GGG AAA GAC ACC AGC AGT ATA        2224
Val Ala Lys Ile Thr Ala Gln Ala Thr Gly Lys Asp Thr Ser Ser Ile
            700                 705                 710

ACT TCT TGT GGG GAC GGA AAT GTT GTC AAG CAG GAG CAG CTA AGT CCT        2272
Thr Ser Cys Gly Asp Gly Asn Val Val Lys Gln Glu Gln Leu Ser Pro
715                 720                 725

AAG AAG AAG GAG AAT AAT GCA CTT CTT AGA TAC CTG CTG GAC AGG GAT        2320
Lys Lys Lys Glu Asn Asn Ala Leu Leu Arg Tyr Leu Leu Asp Arg Asp
730                 735                 740                 745

GAT CCT AGT GAT GCA CTC TCT AAA GAA CTA CAG CCC CAA GTG GAA GGA        2368
Asp Pro Ser Asp Ala Leu Ser Lys Glu Leu Gln Pro Gln Val Glu Gly
                750                 755                 760

GTG GAC AAT AAA ATG AGT CAG TGC ACC AGC TCC ACC ATT CCT AGC TCA        2416
Val Asp Asn Lys Met Ser Gln Cys Thr Ser Ser Thr Ile Pro Ser Ser
                765                 770                 775

AGT CAA GAG AAA GAC CCT AAA ATT AAG ACA GAG ACA AGT GAA GAG GGA        2464
Ser Gln Glu Lys Asp Pro Lys Ile Lys Thr Glu Thr Ser Glu Glu Gly
            780                 785                 790

TCT GGA GAC TTG GAT AAT CTA GAT GCT ATT CTT GGT GAT CTG ACT AGT        2512
Ser Gly Asp Leu Asp Asn Leu Asp Ala Ile Leu Gly Asp Leu Thr Ser
795                 800                 805

TCT GAC TTT TAC AAT AAT TCC ATA TCC TCA AAT GGT AGT CAT CTG GGG        2560
Ser Asp Phe Tyr Asn Asn Ser Ile Ser Ser Asn Gly Ser His Leu Gly
810                 815                 820                 825

ACT AAG CAA CAG GTG TTT CAA GGA ACT AAT TCT CTG GGT TTG AAA AGT        2608
Thr Lys Gln Gln Val Phe Gln Gly Thr Asn Ser Leu Gly Leu Lys Ser
                830                 835                 840

TCA CAG TCT GTG CAG TCT ATT CGT CCT CCA TAT AAC CGA GCA GTG TCT        2656
Ser Gln Ser Val Gln Ser Ile Arg Pro Pro Tyr Asn Arg Ala Val Ser
            845                 850                 855

CTG GAT AGC CCT GTT TCT GTT GGC TCA AGT CCT CCA GTA AAA AAT ATC        2704
Leu Asp Ser Pro Val Ser Val Gly Ser Ser Pro Pro Val Lys Asn Ile
                860                 865                 870

AGT GCT TTC CCC ATG TTA CCA AAG CAA CCC ATG TTG GGT GGG AAT CCA        2752
Ser Ala Phe Pro Met Leu Pro Lys Gln Pro Met Leu Gly Gly Asn Pro
875                 880                 885
```

```
AGA ATG ATG GAT AGT CAG GAA AAT TAT GGC TCA AGT ATG GGT GGG CCA          2800
Arg Met Met Asp Ser Gln Glu Asn Tyr Gly Ser Ser Met Gly Gly Pro
890             895                 900                 905

AAC CGA AAT GTG ACT GTG ACT CAG ACT CCT TCC TCA GGA GAC TGG GGC          2848
Asn Arg Asn Val Thr Val Thr Gln Thr Pro Ser Ser Gly Asp Trp Gly
                910                 915                 920

TTA CCA AAC TCA AAG GCC GGC AGA ATG GAA CCT ATG AAT TCA AAC TCC          2896
Leu Pro Asn Ser Lys Ala Gly Arg Met Glu Pro Met Asn Ser Asn Ser
            925                 930                 935

ATG GGA AGA CCA GGA GGA GAT TAT AAT ACT TCT TTA CCC AGA CCT GCA          2944
Met Gly Arg Pro Gly Gly Asp Tyr Asn Thr Ser Leu Pro Arg Pro Ala
        940                 945                 950

CTG GGT GGC TCT ATT CCC ACA TTG CCT CTT CGG TCT AAT AGC ATA CCA          2992
Leu Gly Gly Ser Ile Pro Thr Leu Pro Leu Arg Ser Asn Ser Ile Pro
    955                 960                 965

GGT GCG AGA CCA GTA TTG CAA CAG CAG CAG CAG ATG CTT CAA ATG AGG          3040
Gly Ala Arg Pro Val Leu Gln Gln Gln Gln Gln Met Leu Gln Met Arg
970                 975                 980                 985

CCT GGT GAA ATC CCC ATG GGA ATG GGG GCT AAT CCC TAT GGC CAA GCA          3088
Pro Gly Glu Ile Pro Met Gly Met Gly Ala Asn Pro Tyr Gly Gln Ala
                990                 995                 1000

GCA GCA TCT AAC CAA CTG GGT TCC TGG CCC GAT GGC ATG TTG TCC ATG          3136
Ala Ala Ser Asn Gln Leu Gly Ser Trp Pro Asp Gly Met Leu Ser Met
            1005                1010                1015

GAA CAA GTT TCT CAT GGC ACT CAA AAT AGG CCT CTT CTT AGG AAT TCC          3184
Glu Gln Val Ser His Gly Thr Gln Asn Arg Pro Leu Leu Arg Asn Ser
        1020                1025                1030

CTG GAT GAT CTT GTT GGG CCA CCT TCC AAC CTG GAA GGC CAG AGT GAC          3232
Leu Asp Asp Leu Val Gly Pro Pro Ser Asn Leu Glu Gly Gln Ser Asp
    1035                1040                1045

GAA AGA GCA TTA TTG GAC CAG CTG CAC ACT CTT CTC AGC AAC ACA GAT          3280
Glu Arg Ala Leu Leu Asp Gln Leu His Thr Leu Leu Ser Asn Thr Asp
1050                1055                1060                1065

GCG ACA GGC CTG GAA GAA ATT GAC AGA GCT TTG GGC ATT CCT GAA CTT          3328
Ala Thr Gly Leu Glu Glu Ile Asp Arg Ala Leu Gly Ile Pro Glu Leu
                1070                1075                1080

GTC AAT CAG GGA CAG GCA TTA GAG CCC AAA CAG GAT GCT TTC CAA GGC          3376
Val Asn Gln Gly Gln Ala Leu Glu Pro Lys Gln Asp Ala Phe Gln Gly
            1085                1090                1095

CAA GAA GCA GCA GTA ATG ATG GAT CAG AAG GCA GGA TTA TAT GGA CAG          3424
Gln Glu Ala Ala Val Met Met Asp Gln Lys Ala Gly Leu Tyr Gly Gln
        1100                1105                1110

ACA TAC CCA GCA CAG GGG CCT CCA ATG CAA GGA GGC TTT CAT CTT CAG          3472
Thr Tyr Pro Ala Gln Gly Pro Pro Met Gln Gly Gly Phe His Leu Gln
    1115                1120                1125

GGA CAA TCA CCA TCT TTT AAC TCT ATG ATG AAT CAG ATG AAC CAG CAA          3520
Gly Gln Ser Pro Ser Phe Asn Ser Met Met Asn Gln Met Asn Gln Gln
1130                1135                1140                1145

GGC AAT TTT CCT CTC CAA GGA ATG CAC CCA CGA GCC AAC ATC ATG AGA          3568
Gly Asn Phe Pro Leu Gln Gly Met His Pro Arg Ala Asn Ile Met Arg
                1150                1155                1160

CCC CGG ACA AAC ACC CCC AAG CAA CTT AGA ATG CAG CTT CAG CAG AGG          3616
Pro Arg Thr Asn Thr Pro Lys Gln Leu Arg Met Gln Leu Gln Gln Arg
            1165                1170                1175

CTG CAG GGC CAG CAG TTT TTG AAT CAG AGC CGA CAG GCA CTT GAA TTG          3664
Leu Gln Gly Gln Gln Phe Leu Asn Gln Ser Arg Gln Ala Leu Glu Leu
        1180                1185                1190

AAA ATG GAA AAC CCT ACT GCT GGT GGT GCT GCG GTG ATG AGG CCT ATG          3712
Lys Met Glu Asn Pro Thr Ala Gly Gly Ala Ala Val Met Arg Pro Met
```

-continued

```
                  1195                1200                1205
   ATG CAG CCC CAG CAG GGT TTT CTT AAT GCT CAA ATG GTC GCC CAA CGC    3760
   Met Gln Pro Gln Gln Gly Phe Leu Asn Ala Gln Met Val Ala Gln Arg
   1210                1215                1220                1225

AGC AGA GAG CTG CTA AGT CAT CAC TTC CGA CAA CAG AGG GTG GCT ATG    3808
   Ser Arg Glu Leu Leu Ser His His Phe Arg Gln Gln Arg Val Ala Met
                       1230                1235                1240

ATG ATG CAG CAG CAG CAA CAG CAG CAG CAG CAG CAG CAG CAG CAG CAA    3856
   Met Met Gln Gln Gln Gln Gln Gln Gln Gln Gln Gln Gln Gln Gln Gln
               1245                1250                1255

CAG CAA CAG CAA CAG CAG CAA CAG CAG CAA ACC CAG GCC TTC AGC CCA    3904
   Gln Gln Gln Gln Gln Gln Gln Gln Gln Thr Gln Ala Phe Ser Pro
           1260                1265                1270

CCT CCT AAT GTG ACT GCT TCC CCC AGC ATG GAT GGG CTT TTG GCA GGA    3952
   Pro Pro Asn Val Thr Ala Ser Pro Ser Met Asp Gly Leu Leu Ala Gly
       1275                1280                1285

CCC ACA ATG CCA CAA GCT CCT CCG CAA CAG TTT CCA TAT CAA CCA AAT    4000
   Pro Thr Met Pro Gln Ala Pro Pro Gln Gln Phe Pro Tyr Gln Pro Asn
   1290                1295                1300                1305

TAT GGA ATG GGA CAA CAA CCA GAT CCA GCC TTT GGT CGA GTG TCT AGT    4048
   Tyr Gly Met Gly Gln Gln Pro Asp Pro Ala Phe Gly Arg Val Ser Ser
                       1310                1315                1320

CCT CCC AAT GCA ATG ATG TCG TCA AGA ATG GGT CCC TCC CAG AAT CCC    4096
   Pro Pro Asn Ala Met Met Ser Ser Arg Met Gly Pro Ser Gln Asn Pro
               1325                1330                1335

ATG ATG CAA CAC CCG CAG GCT GCA TCC ATC TAT CAG TCC TCA GAA ATG    4144
   Met Met Gln His Pro Gln Ala Ala Ser Ile Tyr Gln Ser Ser Glu Met
           1340                1345                1350

AAG GGC TGG CCA TCA GGA AAT TTG GCC AGG AAC AGC TCC TTT TCC CAG    4192
   Lys Gly Trp Pro Ser Gly Asn Leu Ala Arg Asn Ser Ser Phe Ser Gln
       1355                1360                1365

CAG CAG TTT GCC CAC CAG GGG AAT CCT GCA GTG TAT AGT ATG GTG CAC    4240
   Gln Gln Phe Ala His Gln Gly Asn Pro Ala Val Tyr Ser Met Val His
   1370                1375                1380                1385

ATG AAT GGC AGC AGT GGT CAC ATG GGA CAG ATG AAC ATG AAC CCC ATG    4288
   Met Asn Gly Ser Ser Gly His Met Gly Gln Met Asn Met Asn Pro Met
                       1390                1395                1400

CCC ATG TCT GGC ATG CCT ATG GGT CCT GAT CAG AAA TAC TGC TGA CAT CT 4338
   Pro Met Ser Gly Met Pro Met Gly Pro Asp Gln Lys Tyr Cys *
               1405                1410                1415

CTGCACCAGG ACCTCTTAAG GAAACCACTG TACAAATGAC ACTGCACTAG GATTATTGGG   4398

AAGGAATCAT TGTTCCAGGC ATCCATCTTG AAGAAAGGA CCAGCTTTGA GCTCCATCAA    4458

GGGTATTTTA AGTGATGTCA TTTGAGCAGG AATTCTAG                           4496

(2) INFORMATION FOR SEQ ID NO:2:

(i) SEQUENCE CHARACTERISTICS:
        (A) LENGTH: 1415 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gly Leu Gly Glu Asn Leu Asp Pro Leu Ala Ser Asp Ser Arg
 1               5                  10                  15

Lys Arg Lys Leu Pro Cys Asp Thr Pro Gly Gln Gly Leu Thr Cys Ser
            20                  25                  30

Gly Glu Lys Arg Arg Arg Glu Gln Glu Ser Lys Tyr Ile Glu Glu Leu
```

```
              35                  40                  45
Ala Glu Leu Ile Ser Ala Asn Leu Ser Asp Ile Asp Asn Phe Asn Val
 50                  55                  60

Lys Pro Asp Lys Cys Ala Ile Leu Lys Glu Thr Val Arg Gln Ile Arg
 65                  70                  75                  80

Gln Ile Lys Glu Gln Gly Lys Thr Ile Ser Asn Asp Asp Val Gln
                     85                  90                  95

Lys Ala Asp Val Ser Ser Thr Gly Gln Gly Val Ile Asp Lys Asp Ser
                    100                 105                 110

Leu Gly Pro Leu Leu Gln Ala Leu Asp Gly Phe Leu Phe Val Val
                    115                 120                 125

Asn Arg Glu Ala Asn Ile Val Phe Val Ser Glu Asn Val Thr Gln Tyr
                    130                 135                 140

Leu Gln Tyr Lys Gln Glu Asp Leu Val Asn Thr Ser Val Tyr Asn Ile
145                 150                 155                 160

Leu His Glu Glu Asp Arg Lys Asp Phe Leu Lys Asn Leu Pro Lys Ser
                    165                 170                 175

Thr Val Asn Gly Val Ser Trp Thr Asn Glu Pro Gln Arg Gln Lys Ser
                    180                 185                 190

His Thr Phe Asn Cys Arg Met Leu Met Lys Thr Pro His Asp Ile Leu
                    195                 200                 205

Glu Asp Ile Asn Ala Ser Pro Glu Met Arg Gln Arg Tyr Glu Thr Met
                    210                 215                 220

Gln Cys Phe Ala Leu Ser Gln Pro Arg Ala Met Met Glu Glu Gly Glu
225                 230                 235                 240

Asp Leu Gln Ser Cys Met Ile Cys Val Ala Arg Arg Ile Thr Thr Gly
                    245                 250                 255

Glu Arg Thr Phe Pro Ser Asn Pro Glu Ser Phe Ile Thr Arg His Asp
                    260                 265                 270

Leu Ser Gly Lys Val Val Asn Ile Asp Thr Asn Ser Leu Arg Ser Ser
                    275                 280                 285

Met Arg Pro Gly Phe Glu Asp Ile Ile Arg Arg Cys Ile Gln Arg Phe
                    290                 295                 300

Phe Ser Leu Asn Asp Gly Gln Ser Trp Ser Gln Lys Arg His Tyr Gln
305                 310                 315                 320

Glu Ala Tyr Leu Asn Gly His Ala Glu Thr Pro Val Tyr Arg Phe Ser
                    325                 330                 335

Leu Ala Asp Gly Thr Ile Val Thr Ala Gln Thr Lys Ser Lys Leu Phe
                    340                 345                 350

Arg Asn Pro Val Thr Asn Asp Arg His Gly Phe Val Ser Thr His Phe
                    355                 360                 365

Leu Gln Arg Glu Gln Asn Gly Tyr Arg Pro Asn Pro Asn Pro Val Gly
                    370                 375                 380

Gln Gly Ile Arg Pro Pro Met Ala Gly Cys Asn Ser Ser Val Gly Gly
385                 390                 395                 400

Met Ser Met Ser Pro Asn Gln Gly Leu Gln Met Pro Ser Ser Arg Ala
                    405                 410                 415

Tyr Gly Leu Ala Asp Pro Ser Thr Thr Gly Gln Met Ser Gly Ala Arg
                    420                 425                 430

Tyr Gly Gly Ser Ser Asn Ile Ala Ser Leu Thr Pro Gly Pro Gly Met
                    435                 440                 445

Gln Ser Pro Ser Ser Tyr Gln Asn Asn Asn Tyr Gly Leu Asn Met Ser
450                 455                 460
```

-continued

```
Ser Pro Pro His Gly Ser Pro Gly Leu Ala Pro Asn Gln Gln Asn Ile
465                 470                 475                 480

Met Ile Ser Pro Arg Asn Arg Gly Ser Pro Lys Ile Ala Ser His Gln
                485                 490                 495

Phe Ser Pro Val Ala Gly Val His Ser Pro Met Ala Ser Ser Gly Asn
            500                 505                 510

Thr Gly Asn His Ser Phe Ser Ser Ser Leu Ser Ala Leu Gln Ala
        515                 520                 525

Ile Ser Glu Gly Val Gly Thr Ser Leu Leu Ser Thr Leu Ser Ser Pro
530                 535                 540

Gly Pro Lys Leu Asp Asn Ser Pro Asn Met Asn Ile Thr Gln Pro Ser
545                 550                 555                 560

Lys Val Ser Asn Gln Asp Ser Lys Ser Pro Leu Gly Phe Tyr Cys Asp
                565                 570                 575

Gln Asn Pro Val Glu Ser Ser Met Cys Gln Ser Asn Ser Arg Asp His
            580                 585                 590

Leu Ser Asp Lys Glu Ser Lys Glu Ser Ser Val Glu Gly Ala Glu Asn
        595                 600                 605

Gln Arg Gly Pro Leu Glu Ser Lys Gly His Lys Lys Leu Leu Gln Leu
610                 615                 620

Leu Thr Cys Ser Ser Asp Asp Arg Gly His Ser Ser Leu Thr Asn Ser
625                 630                 635                 640

Pro Leu Asp Ser Ser Cys Lys Glu Ser Ser Val Ser Val Thr Ser Pro
                645                 650                 655

Ser Gly Val Ser Ser Ser Thr Ser Gly Gly Val Ser Ser Thr Ser Asn
            660                 665                 670

Met His Gly Ser Leu Leu Gln Glu Lys His Arg Ile Leu His Lys Leu
        675                 680                 685

Leu Gln Asn Gly Asn Ser Pro Ala Glu Val Ala Lys Ile Thr Ala Gln
690                 695                 700

Ala Thr Gly Lys Asp Thr Ser Ser Ile Thr Ser Cys Gly Asp Gly Asn
705                 710                 715                 720

Val Val Lys Gln Glu Gln Leu Ser Pro Lys Lys Glu Asn Asn Ala
                725                 730                 735

Leu Leu Arg Tyr Leu Leu Asp Arg Asp Asp Pro Ser Asp Ala Leu Ser
            740                 745                 750

Lys Glu Leu Gln Pro Gln Val Glu Gly Val Asp Asn Lys Met Ser Gln
        755                 760                 765

Cys Thr Ser Ser Thr Ile Pro Ser Ser Gln Glu Lys Asp Pro Lys
770                 775                 780

Ile Lys Thr Glu Thr Ser Glu Glu Gly Ser Gly Asp Leu Asp Asn Leu
785                 790                 795                 800

Asp Ala Ile Leu Gly Asp Leu Thr Ser Ser Asp Phe Tyr Asn Asn Ser
                805                 810                 815

Ile Ser Ser Asn Gly Ser His Leu Gly Thr Lys Gln Gln Val Phe Gln
            820                 825                 830

Gly Thr Asn Ser Leu Gly Leu Lys Ser Ser Gln Ser Val Gln Ser Ile
        835                 840                 845

Arg Pro Pro Tyr Asn Arg Ala Val Ser Leu Asp Ser Pro Val Ser Val
850                 855                 860

Gly Ser Ser Pro Pro Val Lys Asn Ile Ser Ala Phe Pro Met Leu Pro
865                 870                 875                 880
```

-continued

```
Lys Gln Pro Met Leu Gly Gly Asn Pro Arg Met Met Asp Ser Gln Glu
            885                 890                 895
Asn Tyr Gly Ser Ser Met Gly Gly Pro Asn Arg Asn Val Thr Val Thr
        900                 905                 910
Gln Thr Pro Ser Ser Gly Asp Trp Gly Leu Pro Asn Ser Lys Ala Gly
            915                 920                 925
Arg Met Glu Pro Met Asn Ser Asn Ser Met Gly Arg Pro Gly Gly Asp
    930                 935                 940
Tyr Asn Thr Ser Leu Pro Arg Pro Ala Leu Gly Ser Ile Pro Thr
945                 950                 955                 960
Leu Pro Leu Arg Ser Asn Ser Ile Pro Gly Ala Arg Pro Val Leu Gln
                965                 970                 975
Gln Gln Gln Gln Met Leu Gln Met Arg Pro Gly Glu Ile Pro Met Gly
            980                 985                 990
Met Gly Ala Asn Pro Tyr Gly Gln Ala Ala Ser Asn Gln Leu Gly
            995                 1000                1005
Ser Trp Pro Asp Gly Met Leu Ser Met Glu Gln Val Ser His Gly Thr
        1010                1015                1020
Gln Asn Arg Pro Leu Leu Arg Asn Ser Leu Asp Asp Leu Val Gly Pro
1025                1030                1035                1040
Pro Ser Asn Leu Glu Gly Gln Ser Asp Glu Arg Ala Leu Leu Asp Gln
            1045                1050                1055
Leu His Thr Leu Leu Ser Asn Thr Asp Ala Thr Gly Leu Glu Glu Ile
            1060                1065                1070
Asp Arg Ala Leu Gly Ile Pro Glu Leu Val Asn Gln Gly Gln Ala Leu
        1075                1080                1085
Glu Pro Lys Gln Asp Ala Phe Gln Gly Gln Glu Ala Ala Val Met Met
    1090                1095                1100
Asp Gln Lys Ala Gly Leu Tyr Gly Gln Thr Tyr Pro Ala Gln Gly Pro
1105                1110                1115                1120
Pro Met Gln Gly Gly Phe His Leu Gly Gln Ser Pro Ser Phe Asn
            1125                1130                1135
Ser Met Met Asn Gln Met Asn Gln Gln Gly Asn Phe Pro Leu Gln Gly
        1140                1145                1150
Met His Pro Arg Ala Asn Ile Met Arg Pro Arg Thr Asn Thr Pro Lys
        1155                1160                1165
Gln Leu Arg Met Gln Leu Gln Gln Arg Leu Gln Gly Gln Gln Phe Leu
    1170                1175                1180
Asn Gln Ser Arg Gln Ala Leu Glu Leu Lys Met Glu Asn Pro Thr Ala
1185                1190                1195                1200
Gly Gly Ala Ala Val Met Arg Pro Met Met Gln Pro Gln Gln Gly Phe
            1205                1210                1215
Leu Asn Ala Gln Met Val Ala Gln Arg Ser Arg Glu Leu Leu Ser His
        1220                1225                1230
His Phe Arg Gln Gln Arg Val Ala Met Met Met Gln Gln Gln Gln Gln
        1235                1240                1245
Gln Gln Gln Gln Gln Gln Gln Gln Gln Gln Gln Gln Gln Gln Gln Gln
    1250                1255                1260
Gln Gln Gln Thr Gln Ala Phe Ser Pro Pro Asn Val Thr Ala Ser
1265                1270                1275                1280
Pro Ser Met Asp Gly Leu Leu Ala Gly Pro Thr Met Pro Gln Ala Pro
            1285                1290                1295
Pro Gln Gln Phe Pro Tyr Gln Pro Asn Tyr Gly Met Gly Gln Gln Pro
```

-continued

```
                     1300                1305                1310
     Asp Pro Ala Phe Gly Arg Val Ser Ser Pro Pro Asn Ala Met Met Ser
             1315                1320                1325

Ser Arg Met Gly Pro Ser Gln Asn Pro Met Met Gln His Pro Gln Ala
             1330                1335                1340

Ala Ser Ile Tyr Gln Ser Ser Glu Met Lys Gly Trp Pro Ser Gly Asn
     1345                1350                1355                1360

Leu Ala Arg Asn Ser Ser Phe Ser Gln Gln Gln Phe Ala His Gln Gly
                     1365                1370                1375

Asn Pro Ala Val Tyr Ser Met Val His Met Asn Gly Ser Ser Gly His
                     1380                1385                1390

Met Gly Gln Met Asn Met Asn Pro Met Pro Met Ser Gly Met Pro Met
             1395                1400                1405

Gly Pro Asp Gln Lys Tyr Cys
             1410                1415
```

What is claimed is:

1. An isolated nucleic acid molecule which encodes a RAC3 protein, comprising a nucleotide sequence at least 90% identical to the nucleotide sequence of SEQ ID NO:1, wherein said RAC3 protein interacts with and activates an AF-2 domain-containing steroid/nuclear receptor.

2. The isolated nucleic acid molecule of claim 1 comprising the coding sequence of SEQ ID NO:1.

3. The isolated nucleic acid molecule of claim 1 comprising the nucleotide sequence of SEQ ID NO:1.

4. An isolated nucleic acid molecule comprising a nucleotide sequence encoding a protein which comprises the amino acid sequence of SEQ ID NO:2.

5. An isolated nucleic acid molecule encoding a RAC3 protein comprising a nucleotide sequence which hybridizes under hybridization conditions of hybridization in 50% formamide at 42° C. followed by washing in 1×SSC/0.1% SDS at 65° C. to a nucleic acid molecule which is the complementary sequence of SEQ ID NO:1, wherein said RAC3 protein interacts with and activates an AF-2 domain-containing steroid/nuclear receptor.

6. A vector comprising the nucleic acid molecule of claim 1.

7. The vector of claim 6, which is a recombinant expression vector.

8. A host cell containing the vector of claim 7.

9. A method for producing RAC3 protein comprising culturing the host cell of claim 8 in a suitable medium until RAC3 protein is produced.

10. The method of claim 9, further comprising isolating RAC3 protein from the medium or the host cell.

11. An isolated nucleic acid molecule at least 200 nucleotides in length which encodes a RAC3 N-terminal steroid receptor interacting domain comprising amino acids 613 to 752 of SEQ ID NO:2.

12. An isolated nucleic acid molecule at least 200 nucleotides in length which encodes a RAC3 C-terminal trans-activating domain comprising amino acids 1017 to 1179 of SEQ ID NO:2.

* * * * *